(12) United States Patent
Dyatkin et al.

(10) Patent No.: US 9,755,159 B2
(45) Date of Patent: Sep. 5, 2017

(54) ORGANIC MATERIALS FOR OLEDS

(71) Applicant: Universal Display Corporation, Ewing, NJ (US)

(72) Inventors: Alexey Borisovich Dyatkin, Ambler, PA (US); Chuanjun Xia, Lawrenceville, NJ (US); David Zenan Li, Princeton, NJ (US); Lichang Zeng, Lawrenceville, NJ (US); Vadim Adamovich, Yardley, PA (US)

(73) Assignee: Universal Display Corporation, Ewing, NJ (US)

( * ) Notice: Subject to any disclaimer, the term of this patent is extended or adjusted under 35 U.S.C. 154(b) by 284 days.

(21) Appl. No.: 14/551,164

(22) Filed: Nov. 24, 2014

(65) Prior Publication Data

US 2015/0207082 A1 Jul. 23, 2015

Related U.S. Application Data

(60) Provisional application No. 61/930,723, filed on Jan. 23, 2014.

(51) Int. Cl.
*H01L 51/50* (2006.01)
*H01L 51/00* (2006.01)
(Continued)

(52) U.S. Cl.
CPC ...... *H01L 51/0071* (2013.01); *C07D 491/048* (2013.01); *C07D 491/147* (2013.01); *C07D 495/04* (2013.01); *C07D 495/14* (2013.01); *C07D 517/04* (2013.01); *C07D 517/14* (2013.01); *H01L 51/0067* (2013.01); *H01L 51/0054* (2013.01); *H01L 51/0059* (2013.01); *H01L 51/0074* (2013.01); *H01L 51/0085* (2013.01); *H01L 51/5072* (2013.01)

(58) Field of Classification Search
None
See application file for complete search history.

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

EP 0650955 5/1995
EP 1725079 11/2006
(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
(Continued)

*Primary Examiner* — Gregory Clark
(74) *Attorney, Agent, or Firm* — Duane Morris LLP

(57) ABSTRACT

A novel compound based on aza- and diazodibenzofurans; aza- and diaza dibenzothiophenes, such as benzothieno- and benzofuropyrimidines as well as benzothieno- and benzofuropyrazines useful for electron-transporting host material in green, red, yellow, and white phosphorescent emitting devices is disclosed.

19 Claims, 2 Drawing Sheets

(51) Int. Cl.
*C07D 495/04* (2006.01)
*C07D 491/048* (2006.01)
*C07D 517/04* (2006.01)
*C07D 491/147* (2006.01)
*C07D 517/14* (2006.01)
*C07D 495/14* (2006.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0187984 A1 | 7/2010 | Lin et al. |
| 2010/0289406 A1* | 11/2010 | Ma ............... C07D 221/18 313/504 |
| 2011/0260138 A1 | 10/2011 | Xia et al. |
| 2012/0217485 A1 | 8/2012 | Lee et al. |
| 2014/0367667 A1† | 12/2014 | Iwakuma |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2011-084531 A † | 4/2011 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2013102992 | 7/2013 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

(56) References Cited

OTHER PUBLICATIONS

Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett, vol. 75, No. 3, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett, 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylbory1)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Ostergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett, 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner
† cited by third party

ORGANIC MATERIALS FOR OLEDS

CROSS-REFERENCE TO RELATED APPLICATIONS

This application claims priority to U.S. Provisional Application Ser. No. 61/930,723, filed Jan. 23, 2014, the content of which is incorporated herein by reference in its entirety.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and organic materials used in such devices. More specifically, the present invention relates to host compounds for phosphorescent OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

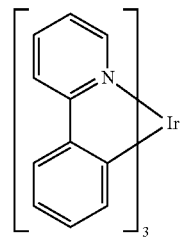

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound having the formula $G^1$-L-$G^2$, Formula I, is disclosed. In Formula I, $G^1$ has the structure:

wherein X is selected from the group consisting of O, S, and Se;
wherein each of $X^1$, $X^2$, $X^3$, $X^4$, $X^5$, $X^6$, $X^7$, and $X^8$ is carbon or nitrogen;
wherein at least one of $X^1$, $X^2$, $X^3$, $X^4$, $X^5$, $X^6$, $X^7$, and $X^8$ is nitrogen;
wherein at least one of $X^1$, $X^2$, $X^3$, and $X^4$ is a carbon and bonded to L;
wherein $R^2$ represents mono, di, tri, tetra substitutions or no substitution;
wherein $R^1$ represents mono, di, tri substitutions or no substitution;
wherein $R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein any adjacent $R^1$ and $R^2$ substitutions are optionally joined to form a fused ring;
$G^2$ is a heteroaryl group having from 3-60 carbon atoms and from 1-6 heteroatoms;
wherein when the heteroatoms are nitrogen atoms the nitrogen atoms can only be on one or more six-membered aromatic rings;
wherein $G^2$ bonds to L at a carbon atom of $G^2$; and
wherein L is selected from the group consisting of a direct bond, benzene, biphenyl, terphenyl, naphthalene, triphenylene, dibenzofuran, dibenzothiophene, dibenzoselenophene, fluorene, pyridine, pyrimidine, pyridazine, pyrazine, quinoline, quinoxaline, naphthyridine, and combinations thereof; wherein L is optionally further unfused substituted with one or more groups selected from hydrogen, deuterium, alkyl, cycloalkyl, aralkyl, alkoxy, aryloxy, amino, silyl, aryl, heteroaryl, and combinations thereof. The new compound can be used as electron-transporting host material in OLEDs and can be used in green, red, yellow, and white emitting devices.

According to another embodiment, a device comprising one or more organic light emitting devices is also disclosed. At least one of the organic light emitting devices includes an anode, a cathode, and an organic layer, disposed between the anode and the cathode, wherein the organic layer can include a compound of Formula I. The device can be a consumer product, an organic light-emitting device, and/or a lighting panel.

A formulation comprising the compound of Formula I is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
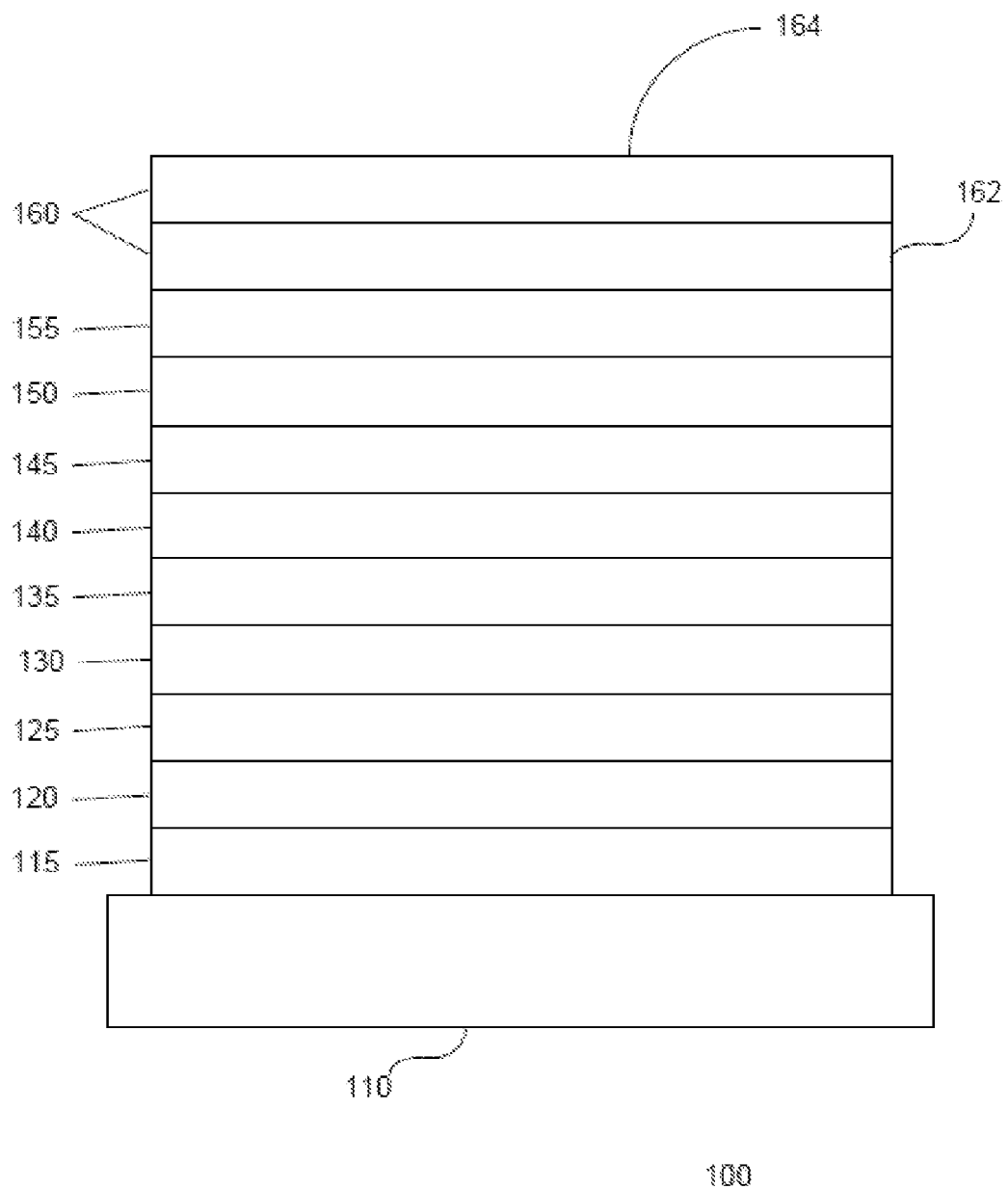
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
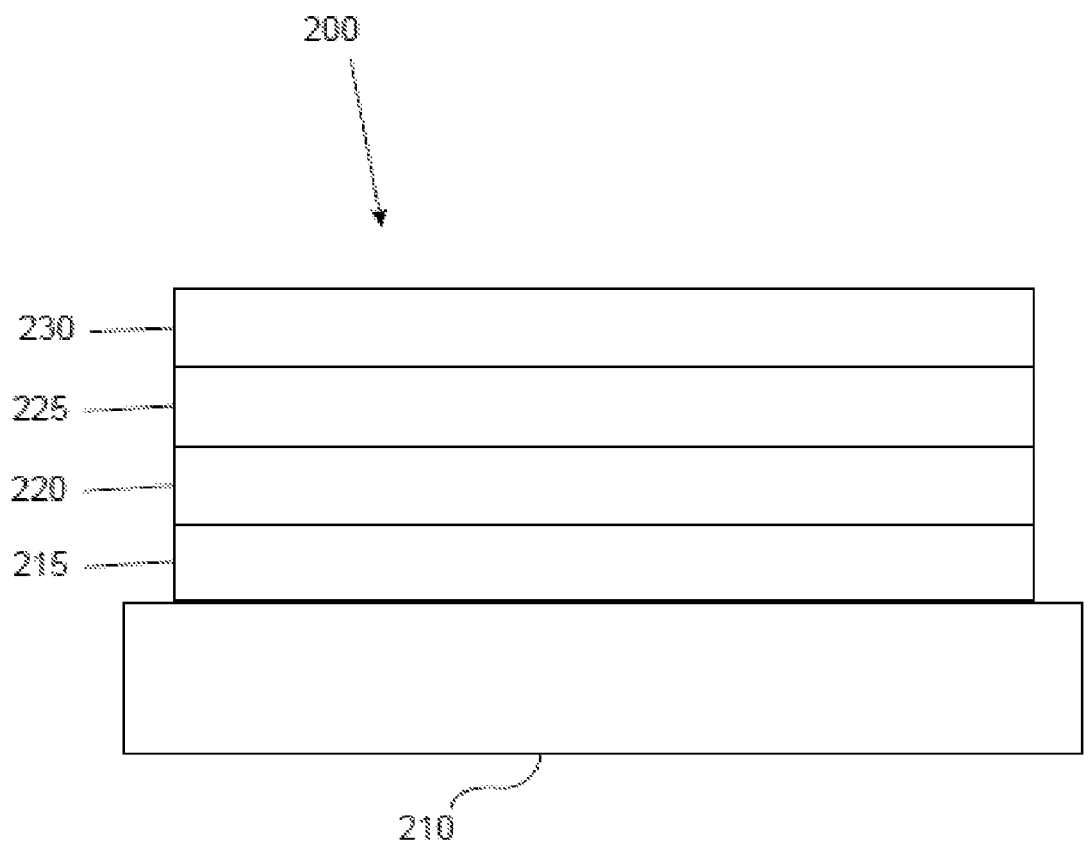
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al. which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, microdisplays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Hetero-aromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

The present disclosure provides a novel electron-transporting host compounds based on aza-dibenzofurans; aza-dibenzothiophenes, such as benzothieno- and benzofuropyrimidines; as well as benzothieno- and benzofuropyrazines. The new compounds can be used in green, red, yellow and white emitting devices.

According to an embodiment, a compound having the formula $G^1$-L-$G^2$, Formula I, is disclosed. In Formula I, $G^1$ has the structure:

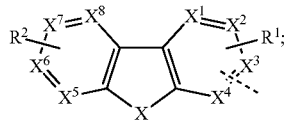

wherein X is selected from the group consisting of O, S, and Se;

wherein each of $X^1$, $X^2$, $X^3$, $X^4$, $X^5$, $X^6$, $X^7$, and $X^8$ is carbon or nitrogen;

wherein at least one of $X^1$, $X^2$, $X^3$, $X^4$, $X^5$, $X^6$, $X^7$, and $X^8$ is nitrogen;

wherein at least one of $X^1$, $X^2$, $X^3$, and $X^4$ is a carbon and bonded to L;

wherein $R^2$ represents mono, di, tri, tetra substitutions or no substitution;

wherein $R^1$ represents mono, di, tri substitutions or no substitution;

wherein $R^1$ and $R^2$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any adjacent $R^1$ and $R^2$ substitutions are optionally joined to form a fused ring;

$G^2$ is a heteroaryl group having from 3-60 carbon atoms and from 1-6 heteroatoms;

wherein when the heteroatoms are nitrogen atoms the nitrogen atoms can only be on one or more six-membered aromatic rings;

wherein $G^2$ bonds to L at a carbon atom of $G^2$; and

L is selected from the group consisting of a direct bond, benzene, biphenyl, terphenyl, naphthalene, triphenylene, dibenzofuran, dibenzothiophene, dibenzoselenophene, fluorene, pyridine, pyrimidine, pyridazine, pyrazine, quinoline, quinoxaline, naphthyridine, and combinations thereof; wherein L is optionally further unfused substituted with one or more groups selected from hydrogen, deuterium, alkyl, cycloalkyl, aralkyl, alkoxy, aryloxy, amino, silyl, aryl, heteroaryl, and combinations thereof.

In one embodiment of the compound, X is O or S.

In one embodiment of the compound, only one of $X^1$, $X^2$, X, $X^3$, $X^4$, $X^5$, X, $X^7$, and $X^8$ is nitrogen. In one embodiment of the compound, only two of $X^1$, $X^2$, $X^3$, $X^4$, $X^5$, $X^6$, $X^7$, and $X^8$ are nitrogen. In another embodiment of the compound, only two of $X^1$, $X^2$, $X^3$, $X^4$, $X^5$, $X^6$, $X^7$, and $X^8$ are nitrogen and the two nitrogen atoms are on the same ring.

In other embodiments of the compound, only two of $X^1$, $X^2$, $X^3$, and $X^4$ are nitrogen and $X^5$, $X^6$, $X^7$, and $X^8$ are carbon items.

In one embodiment of the compound. $R^1$, and $R^2$ are each independently selected from the group consisting of hydrogen, deuterium, halide, alkyl, phenyl, pyridyl, carbazolyl, and combinations thereof.

In one embodiment of the compound, the heteroatoms in $G^2$ are selected from the group consisting of N, O, S, Se, and combinations thereof.

In one embodiment of the compound, $G^1$ is selected from the group consisting of:

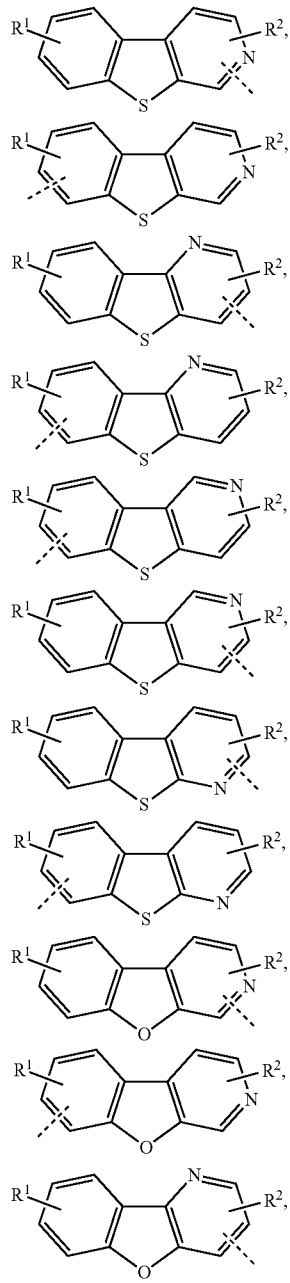

-continued
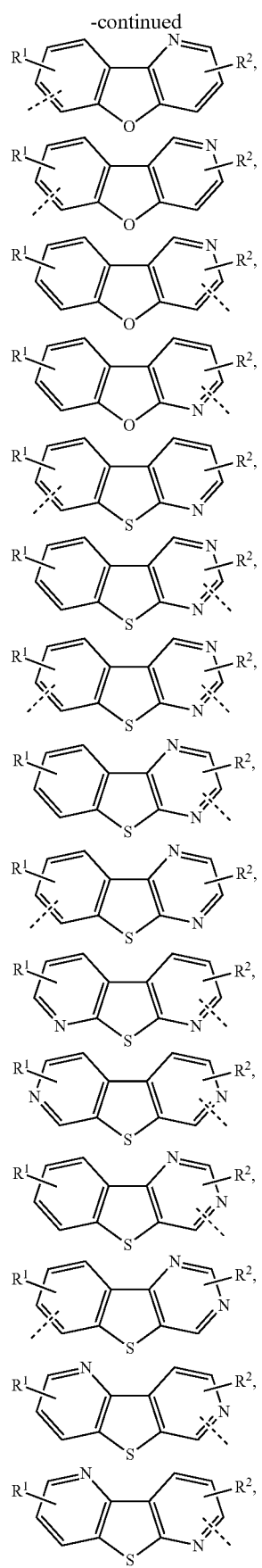
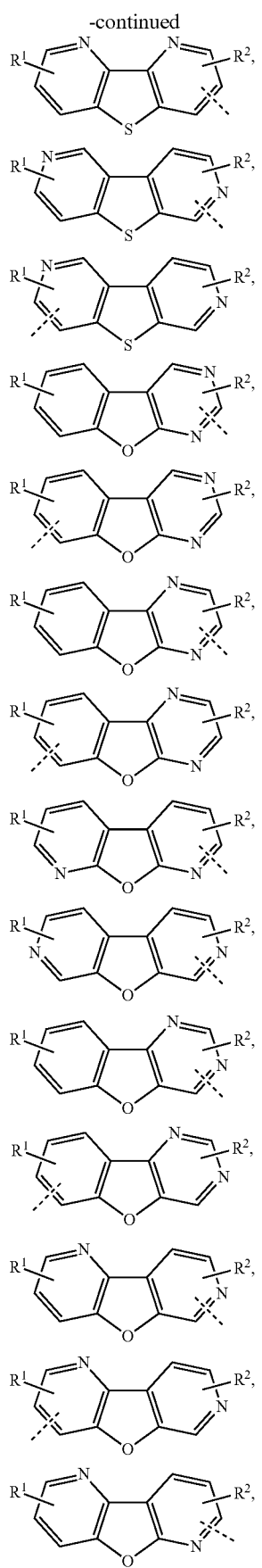

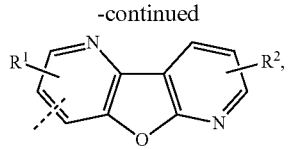
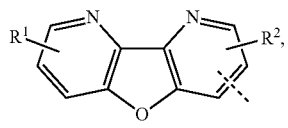
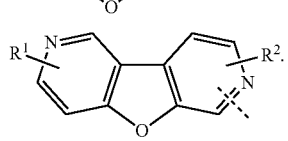
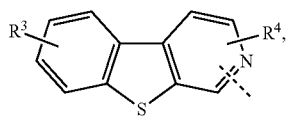
In another embodiment of the compound, G² is selected from the group consisting of:
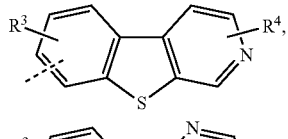
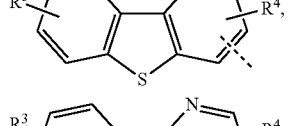
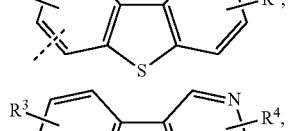
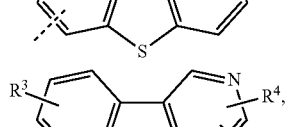
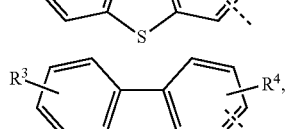
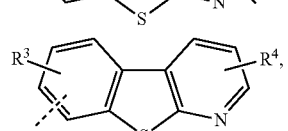
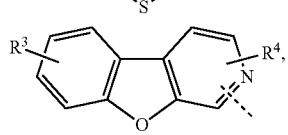
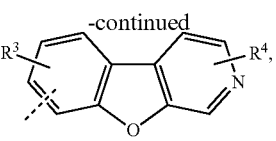
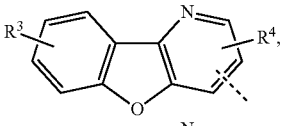
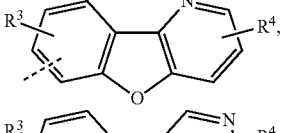
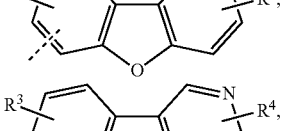
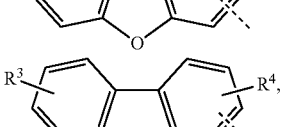
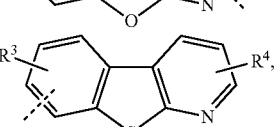
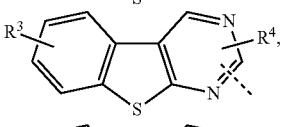
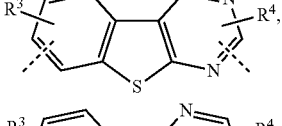
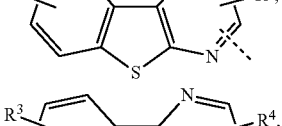
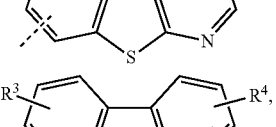
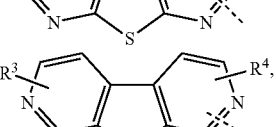
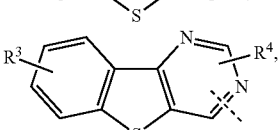
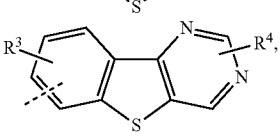

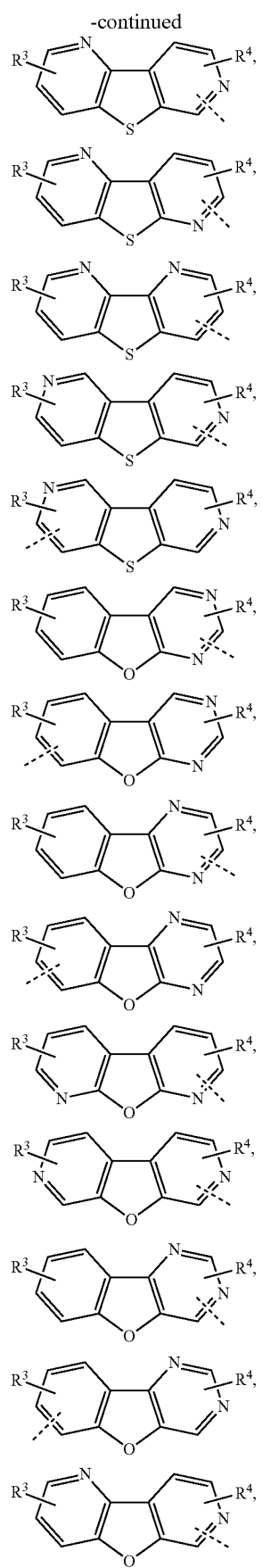
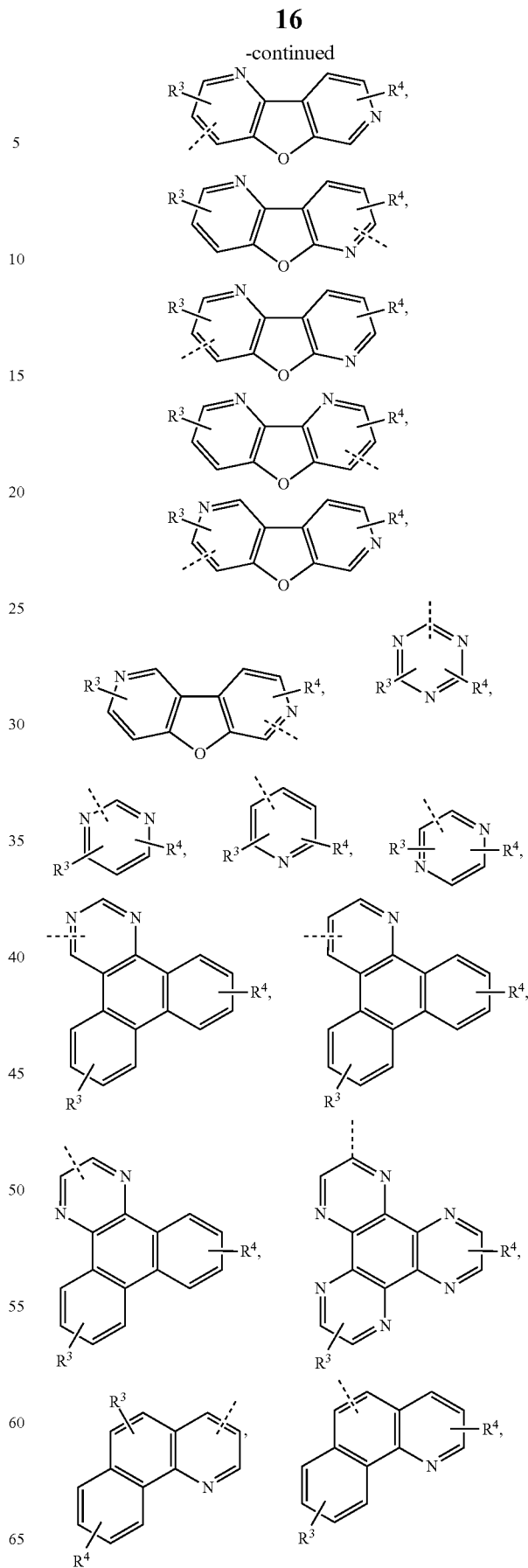

-continued

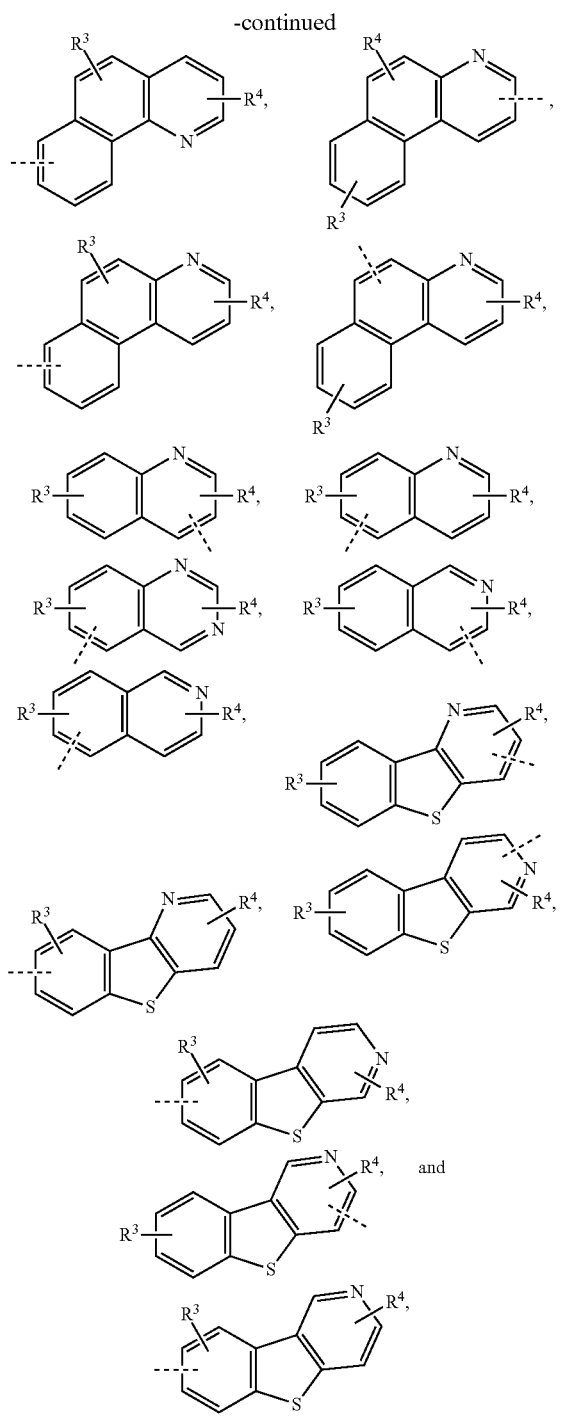

wherein each R³ and R⁴ represents mono, di, tri, tetra substitutions or no substitution;
wherein R³ and R⁴ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any adjacent R¹ and R⁴ substitutions are optionally joined to form a fused ring.
In another embodiment of the compound, L is selected from the group consisting of:

a direct bond

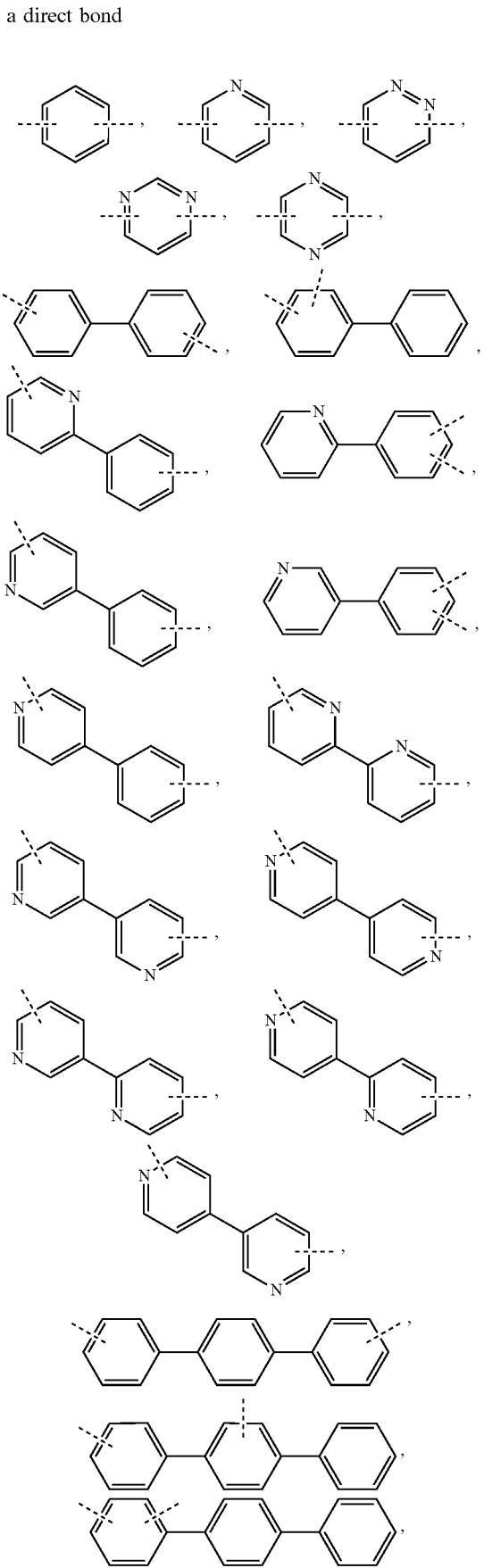

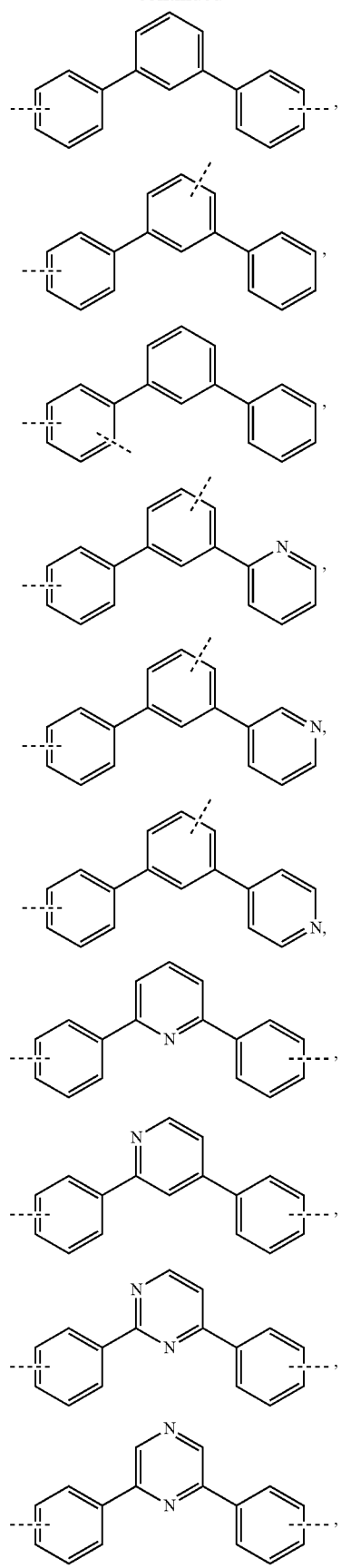
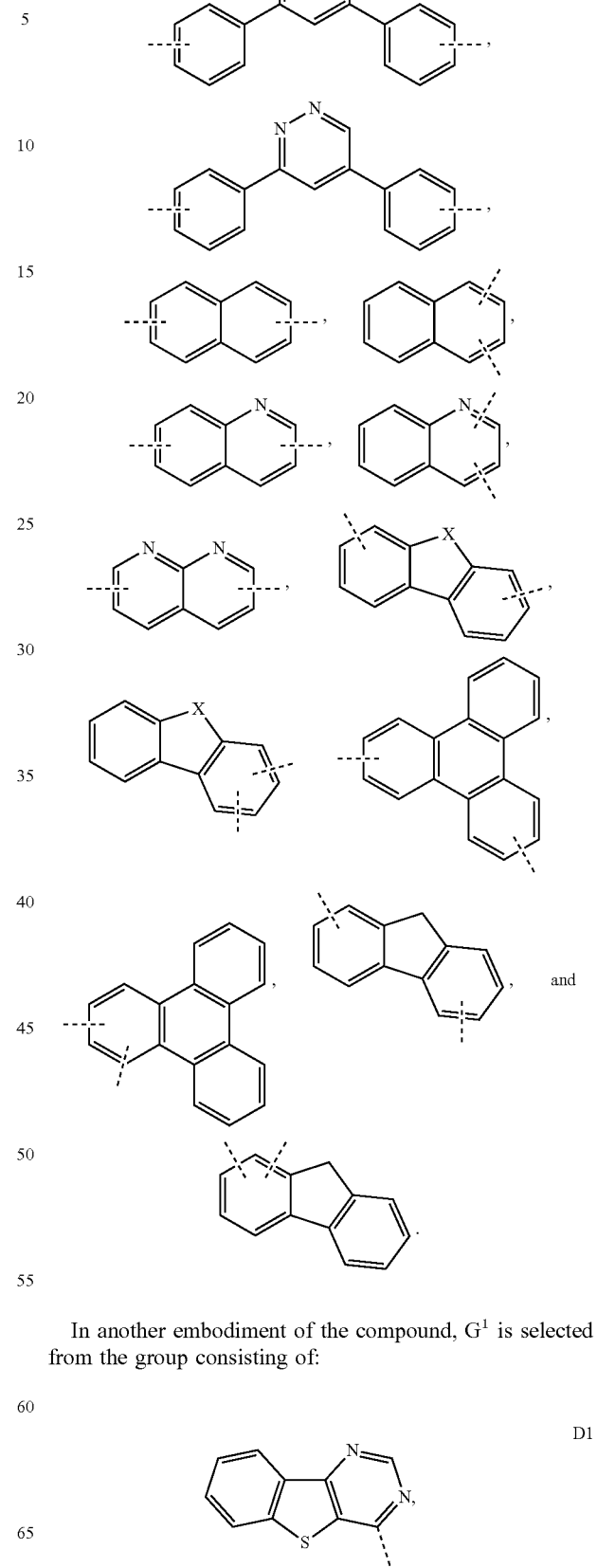
In another embodiment of the compound, $G^1$ is selected from the group consisting of:

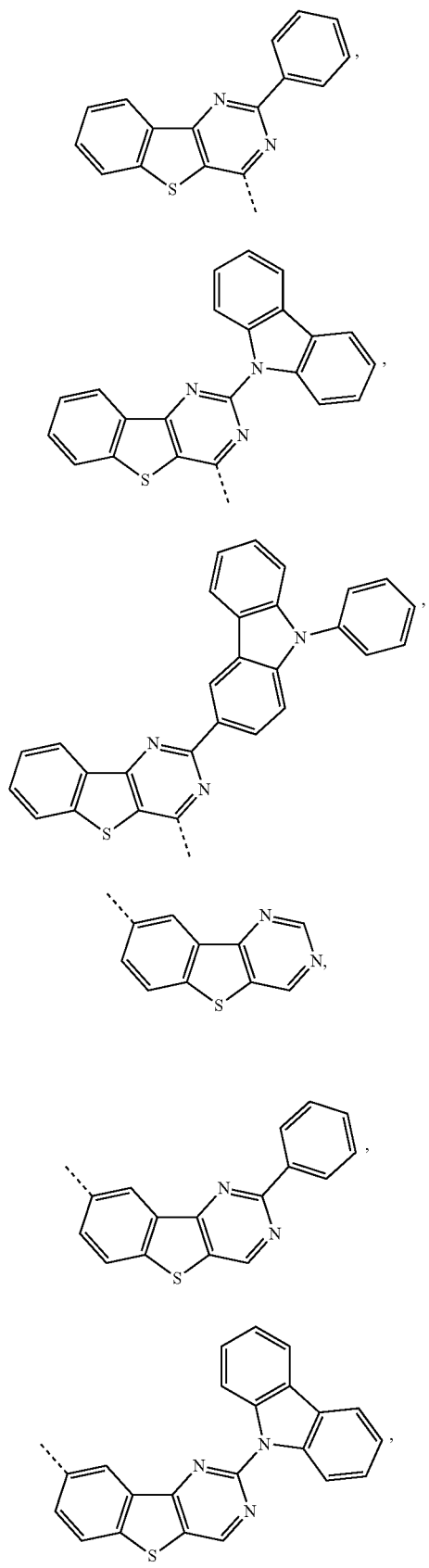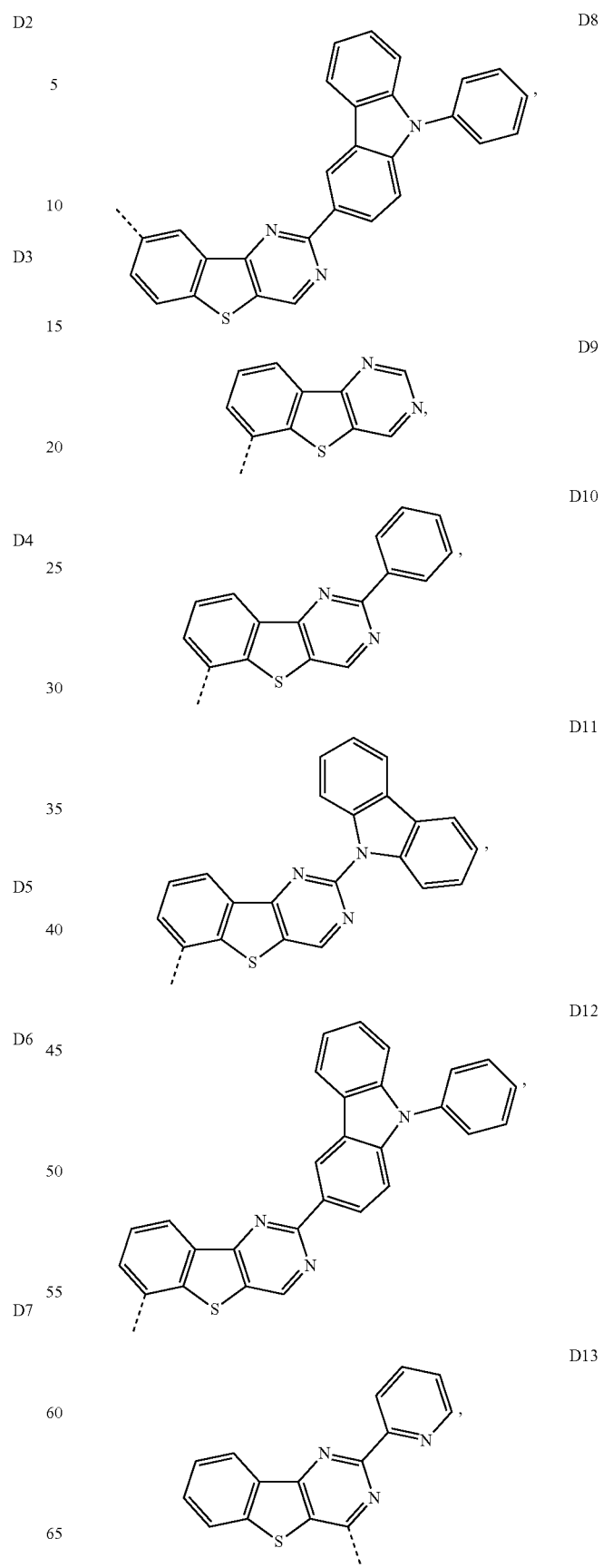

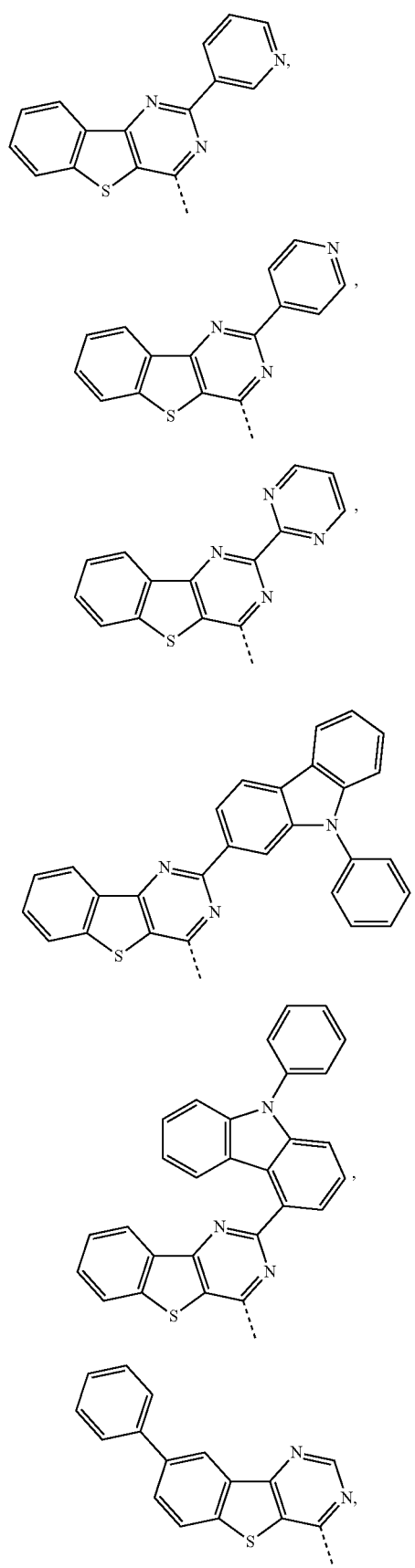
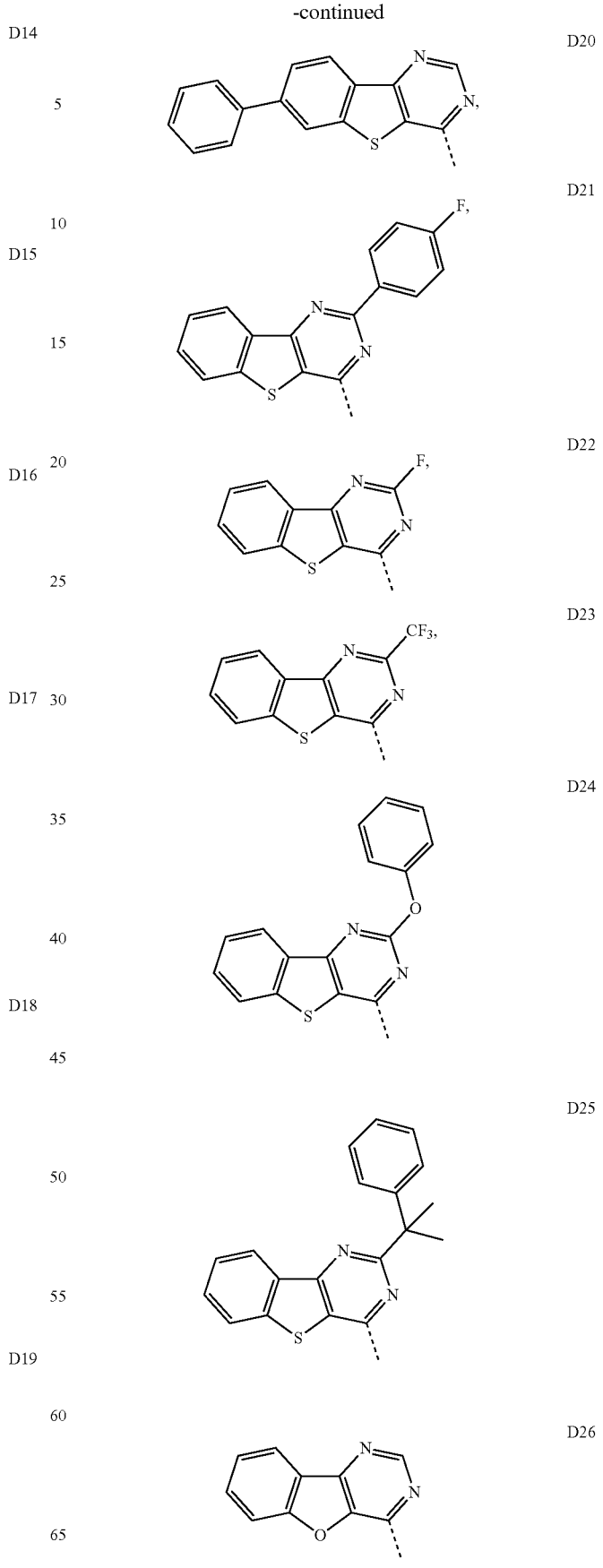

-continued
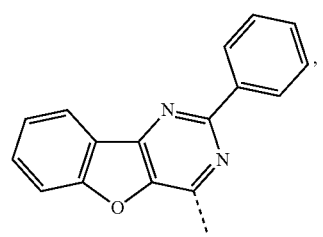
D27
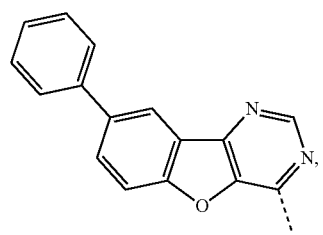
D28
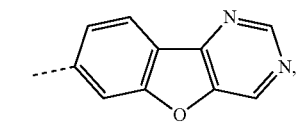
D29
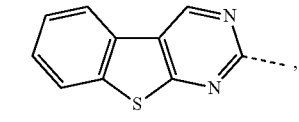
D30
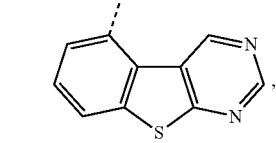
D31
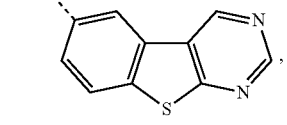
D32
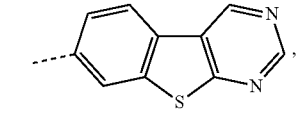
D33
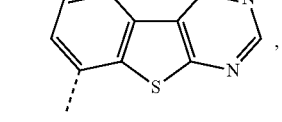
D34
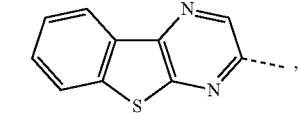
D35
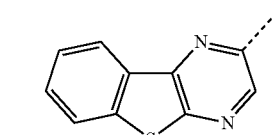
D36
-continued
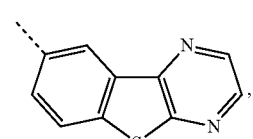
D37
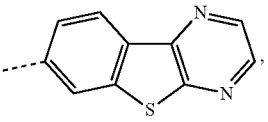
D38
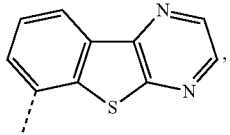
D39
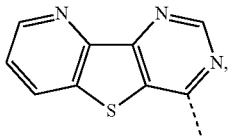
D40
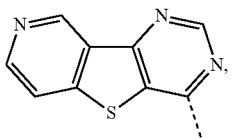
D41
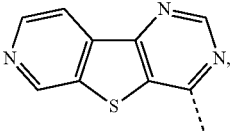
D42
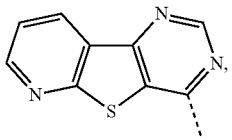
D43
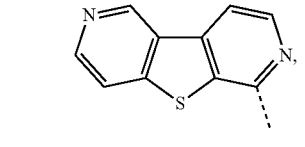
D44
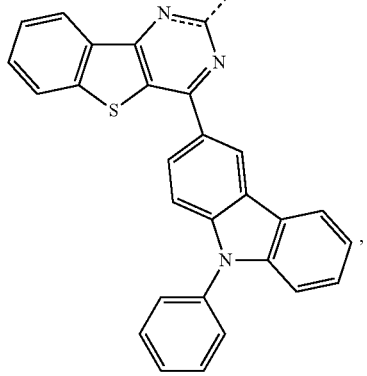
D45

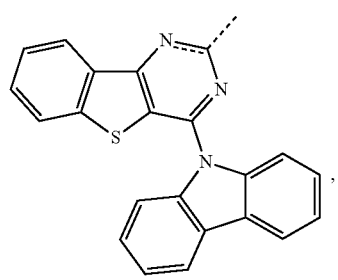
D46
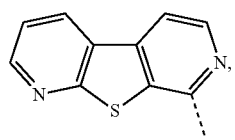
D47
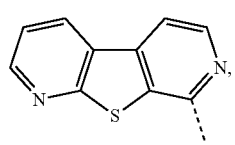
D48
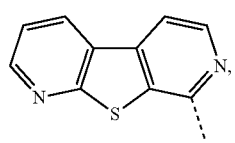
D49
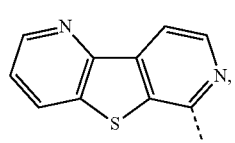
D50
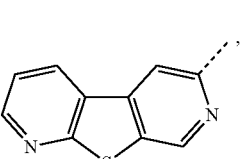
D51
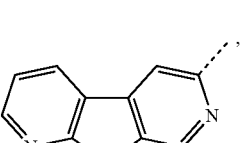
D52
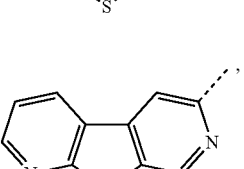
D53
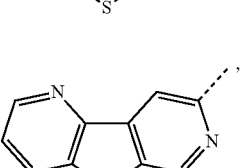
D54
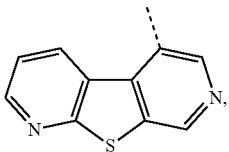
D55
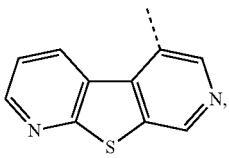
D56
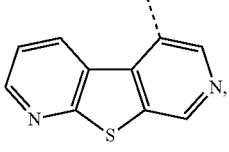
D57
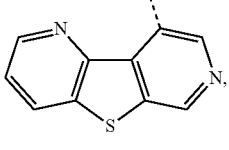
D58
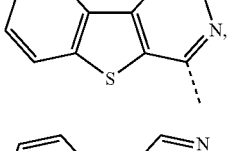
D59
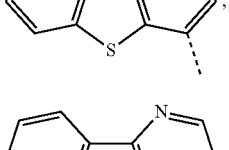
D60
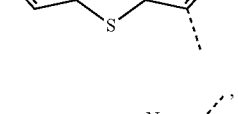
D61
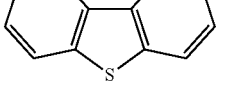
D62
and
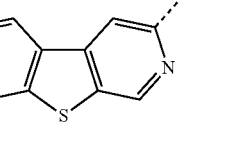
D63
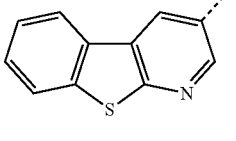
D64

In another embodiment of the compound, L is selected from the group consisting of:
a direct bond (L1),
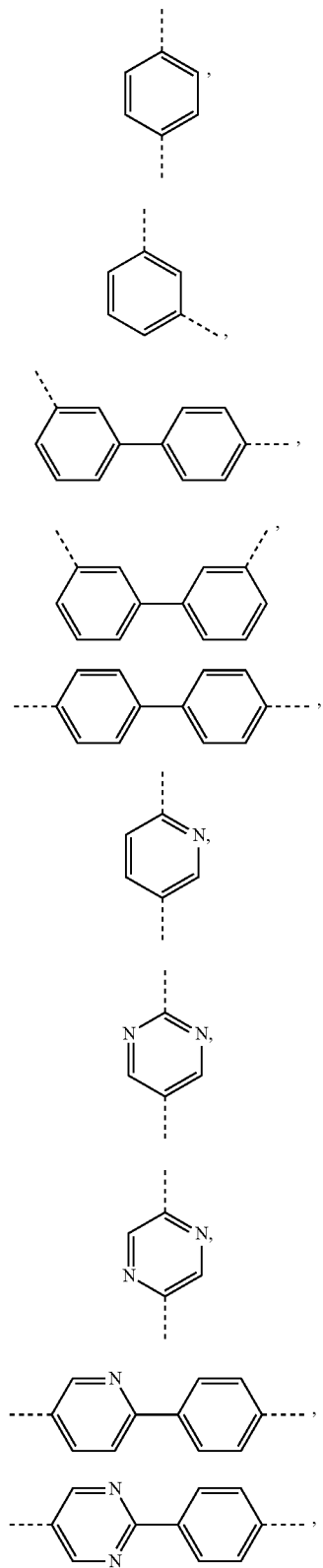
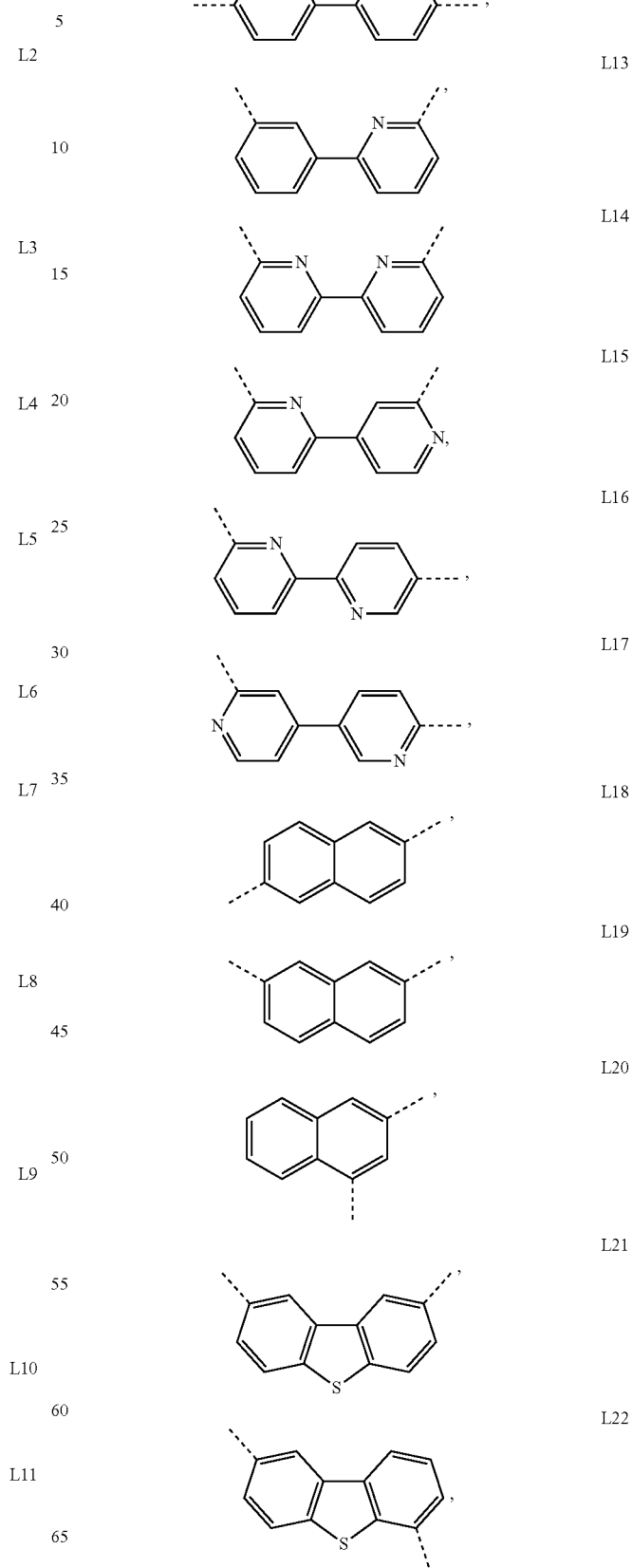

US 9,755,159 B2
| L23 | 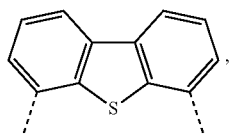 |
| --- | --- |
| L24 | 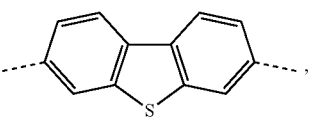 |
| L25 | 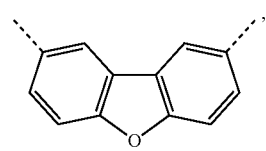 |
| L26 | 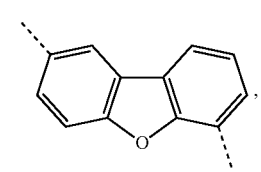 |
| L27 | 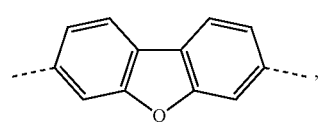 |
| L28 | 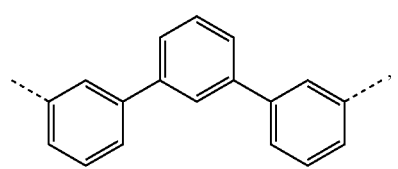 |
| L29 | 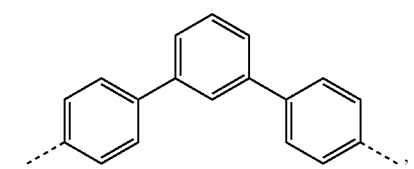 |
| L30 | 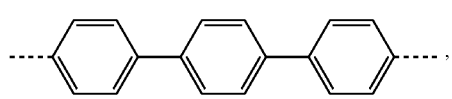 |
| L31 | 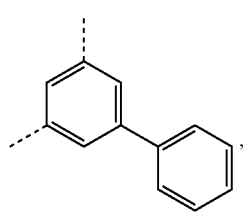 |
| L32 | 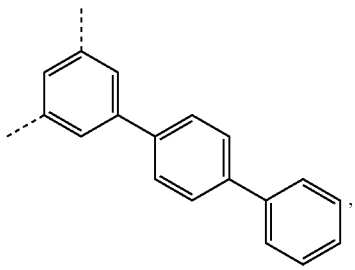 |
| L33 | 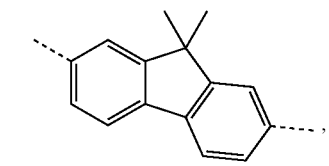 |
| L34 | 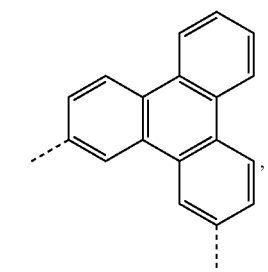 |
| L35 | 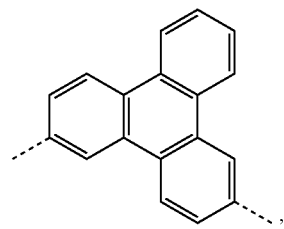 |
| L36 | 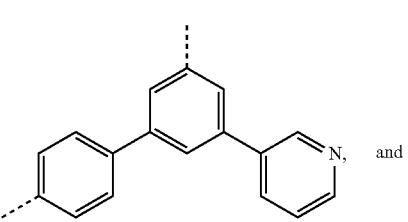 and |
| L37 | 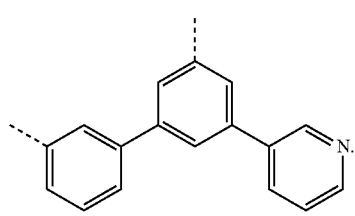 |
In another embodiment of the compound, $G^2$ is selected from the group consisting of:

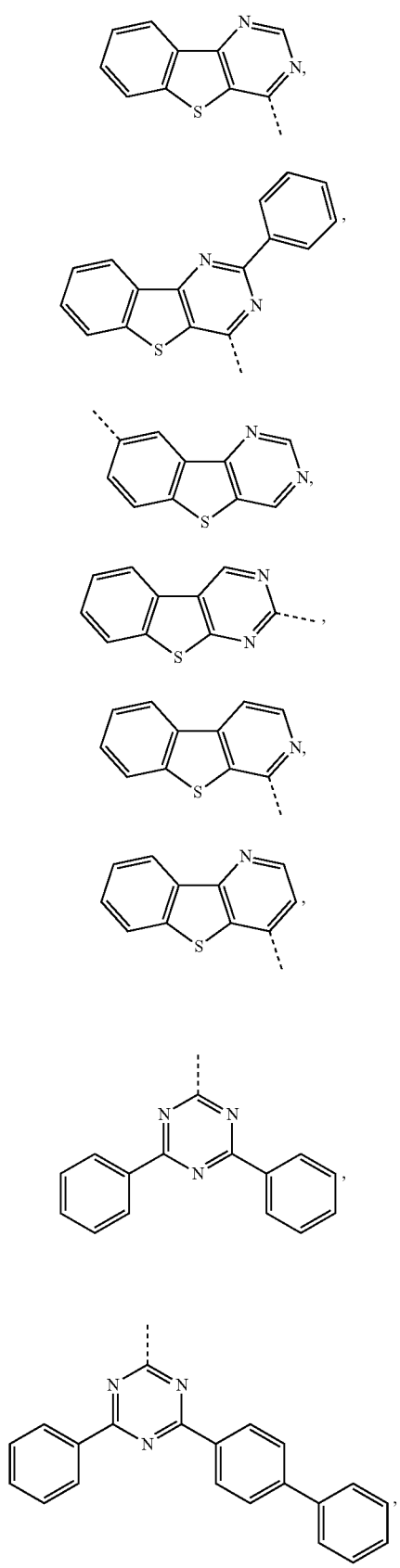
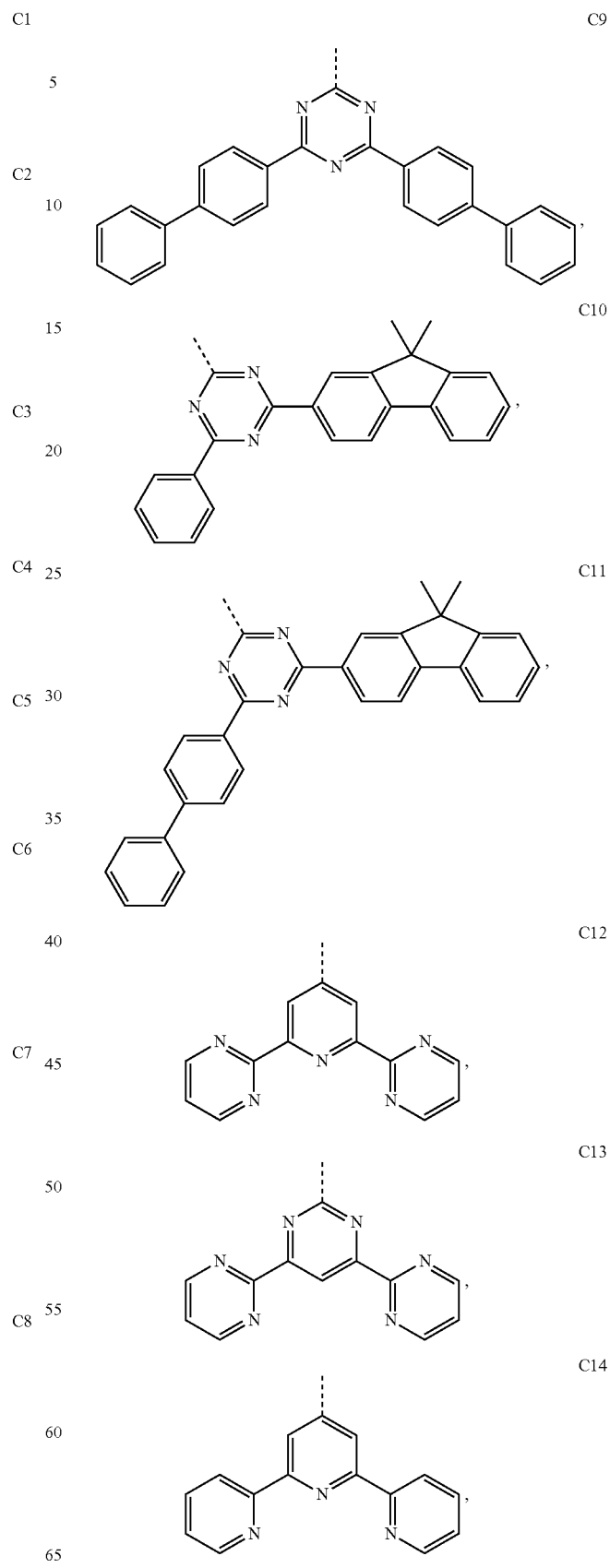

In another embodiment of the compound, the compound is selected from the group consisting of:
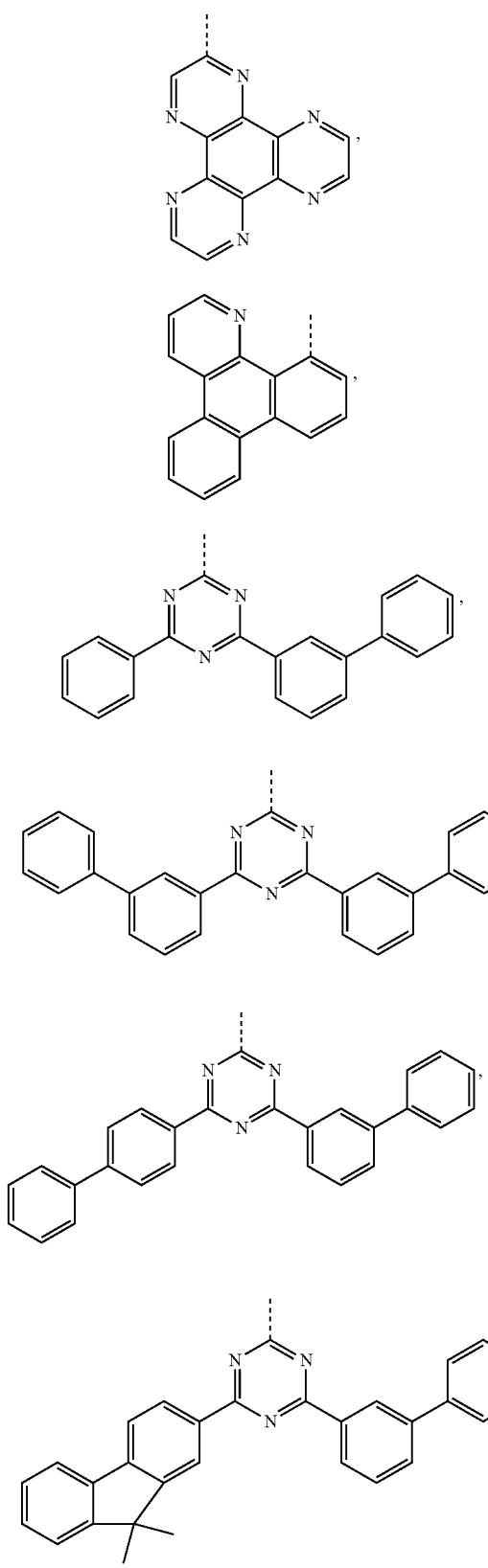
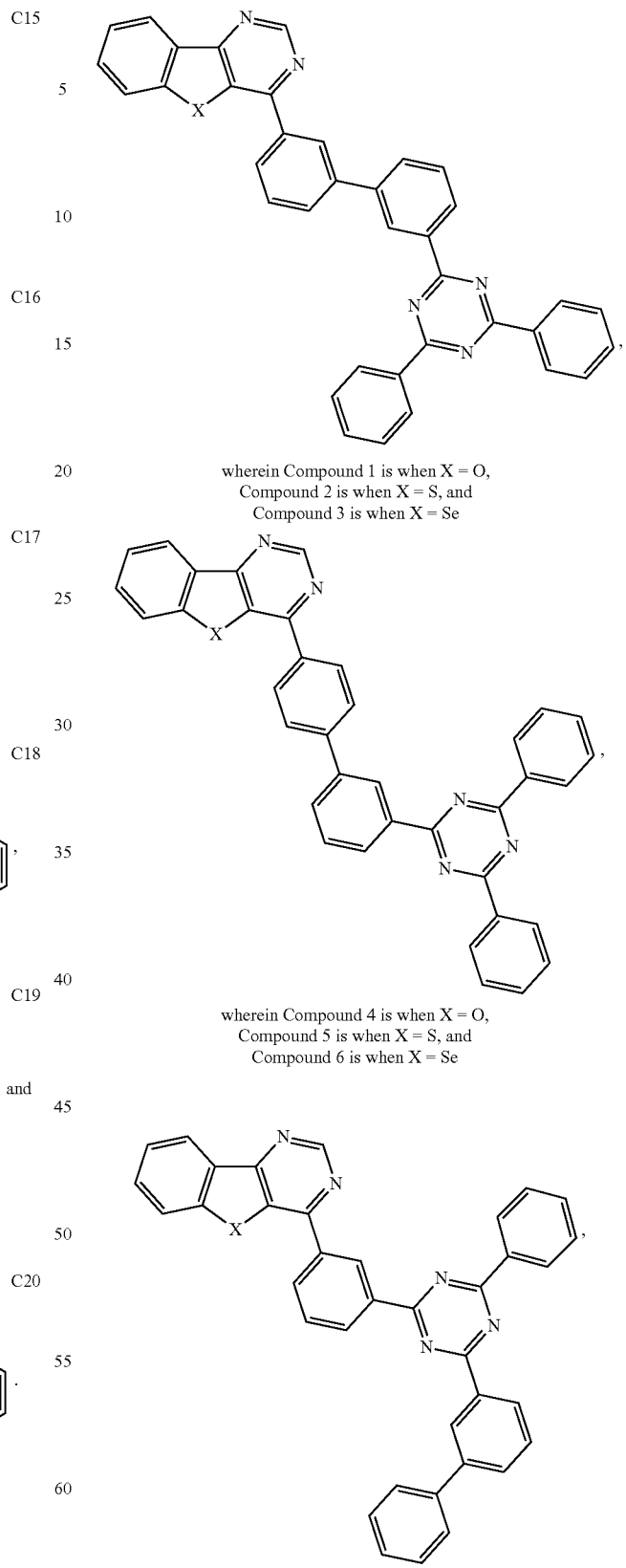
wherein Compound 1 is when X = O,
Compound 2 is when X = S, and
Compound 3 is when X = Se
wherein Compound 4 is when X = O,
Compound 5 is when X = S, and
Compound 6 is when X = Se
wherein Compound 7 is when X = O,
Compound 8 is when X = S, and
Compound 9 is when X = Se

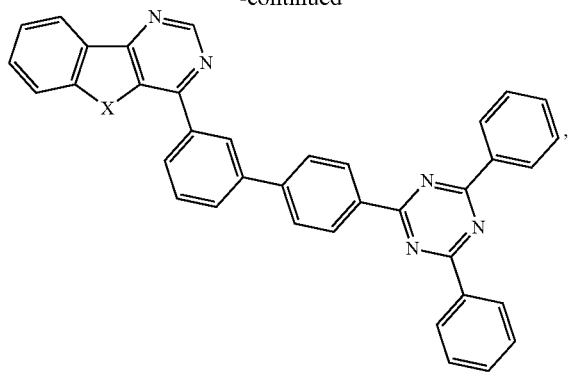

wherein Compound 10 is when X = O,
Compound 11 is when X = S, and
Compound 12 is when X = Se

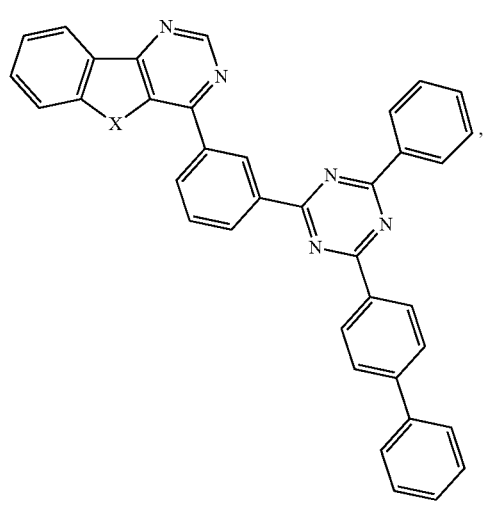

wherein Compound 13 is when X = O,
Compound 14 is when X = S, and
Compound 15 is when X = Se

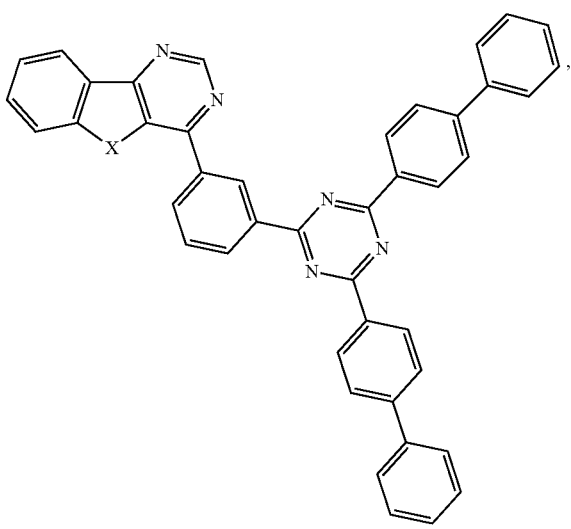

wherein Compound 16 is when X = O,
Compound 17 is when X = S, and
Compound 18 is when X = Se

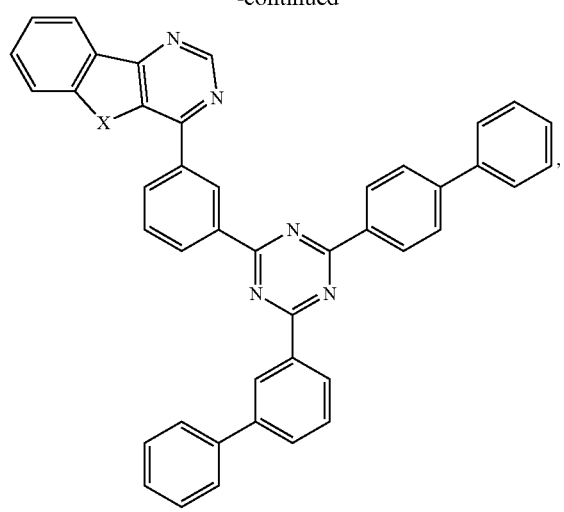

wherein Compound 19 is when X = O,
Compound 20 is when X = S, and
Compound 21 is when X = Se

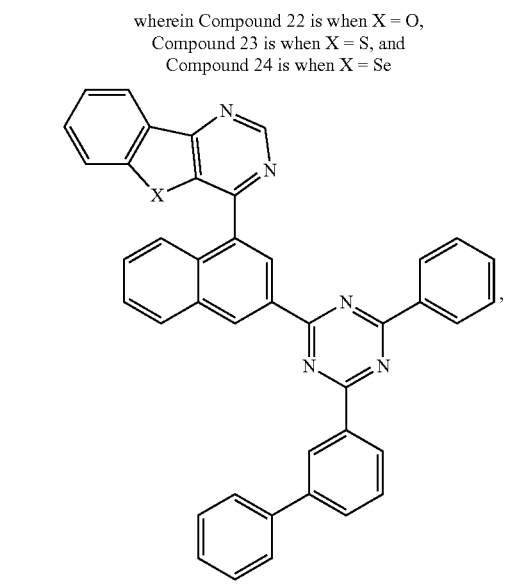

wherein Compound 22 is when X = O,
Compound 23 is when X = S, and
Compound 24 is when X = Se

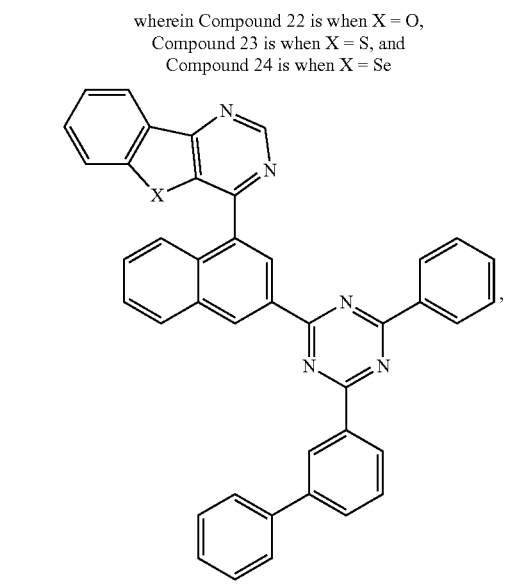

wherein Compound 25 is when X = O,
Compound 26 is when X = S, and
Compound 27 is when X = Se

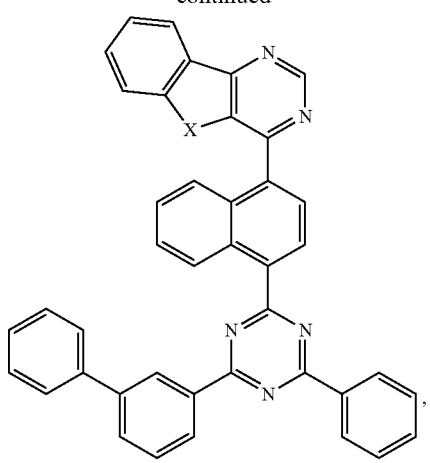

wherein Compound 28 is when X = O,
Compound 29 is when X = S, and
Compound 30 is when X = Se

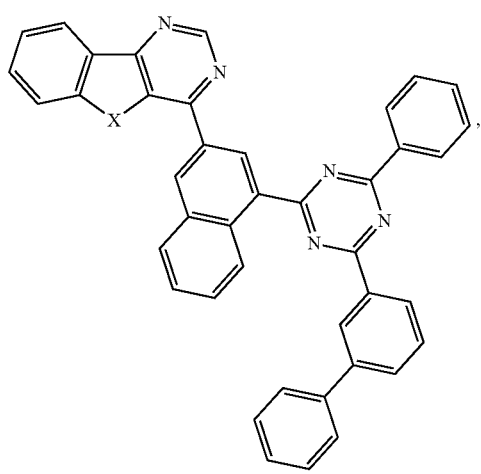

wherein Compound 31 is when X = O,
Compound 32 is when X = S, and
Compound 33 is when X = Se

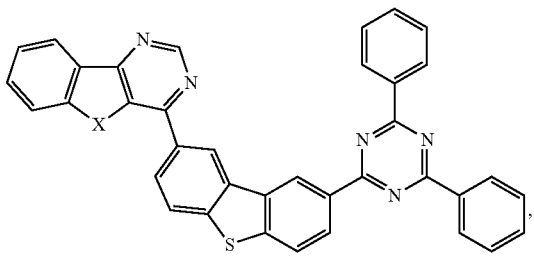

wherein Compound 34 is when X = O,
Compound 35 is when X = S, and
Compound 36 is when X = Se

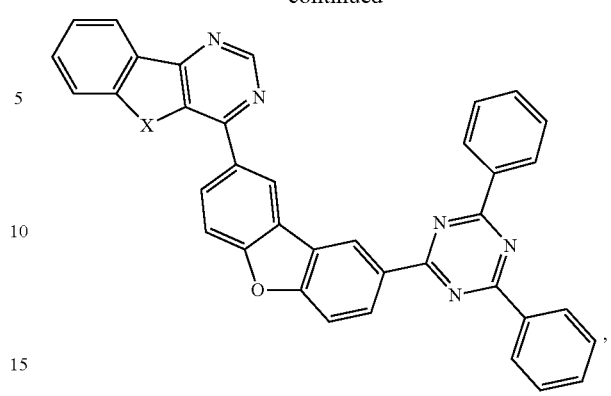

wherein Compound 37 is when X = O,
Compound 38 is when X = S, and
Compound 39 is when X = Se

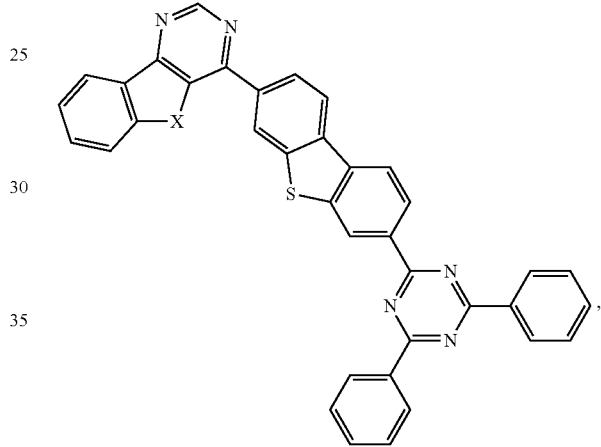

wherein Compound 40 is when X = O,
Compound 41 is when X = S, and
Compound 42 is when X = Se

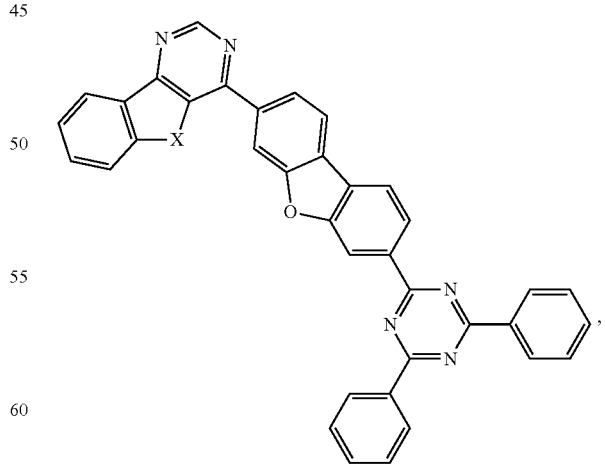

wherein Compound 43 is when X = O,
Compound 44 is when X = S, and
Compound 45 is when X = Se -continued

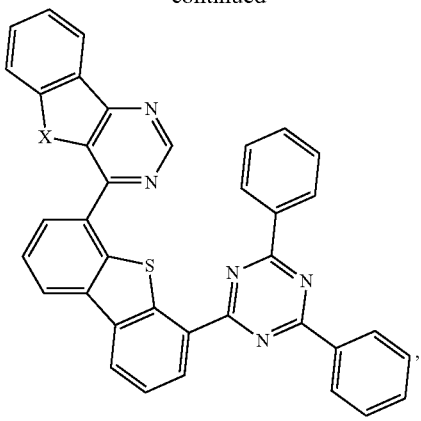

wherein Compound 46 is when X = O,
Compound 47 is when X = S, and
Compound 48 is when X = Se

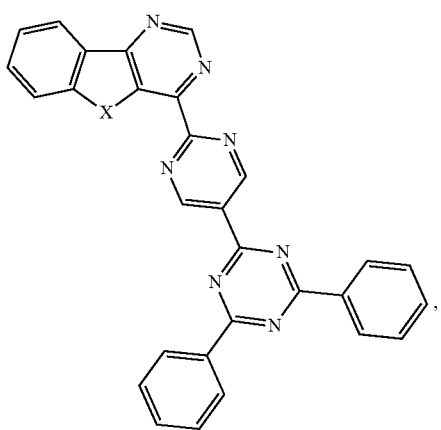

wherein Compound 49 is when X = O,
Compound 50 is when X = S, and
Compound 51 is when X = Se

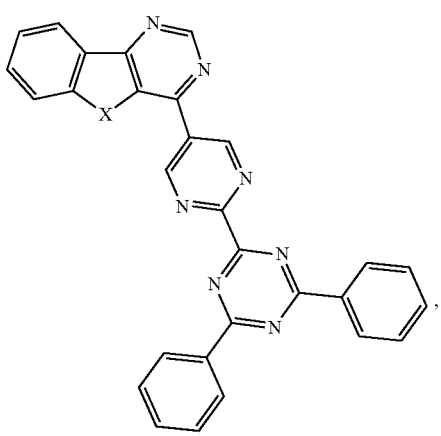

wherein Compound 52 is when X = O,
Compound 53 is when X = S, and
Compound 54 is when X = Se -continued

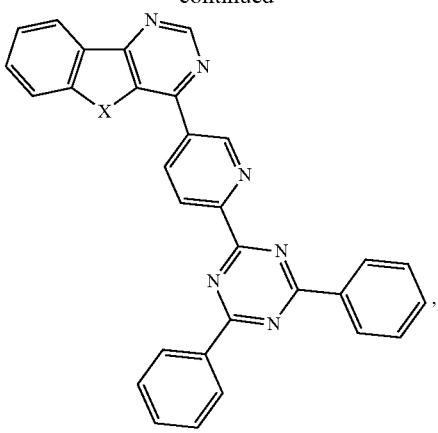

wherein Compound 55 is when X = O,
Compound 56 is when X = S, and
Compound 57 is when X = Se

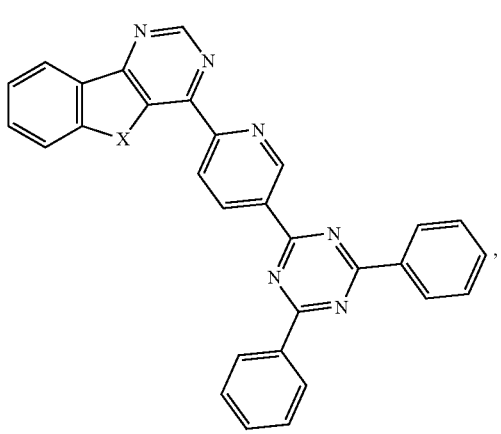

wherein Compound 58 is when X = O,
Compound 59 is when X = S, and
Compound 60 is when X = Se

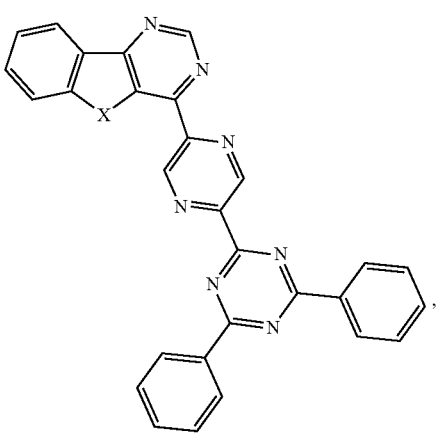

wherein Compound 61 is when X = O,
Compound 62 is when X = S, and
Compound 63 is when X = Se -continued

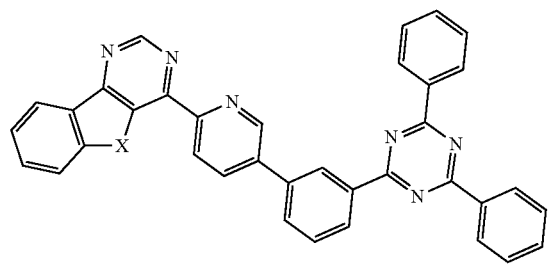

wherein Compound 64 is when X = O,
Compound 65 is when X = S, and
Compound 66 is when X = Se

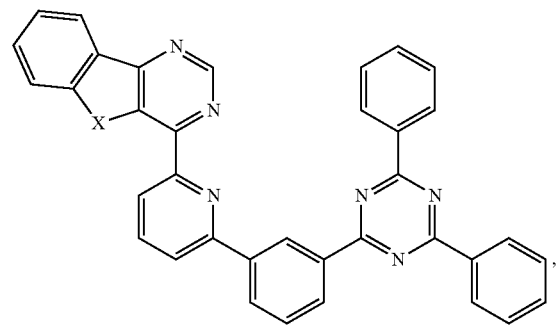

wherein Compound 67 is when X = O,
Compound 68 is when X = S, and
Compound 69 is when X = Se

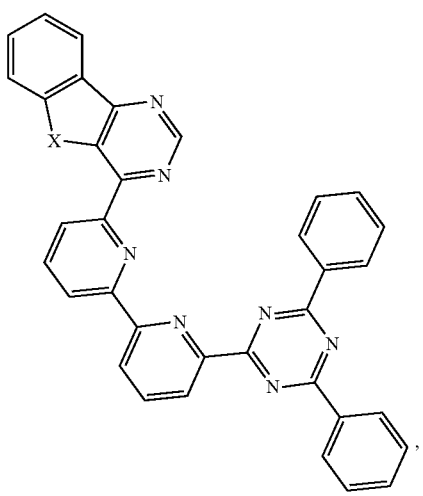

wherein Compound 70 is when X = O,
Compound 71 is when X = S, and
Compound 72 is when X = Se -continued

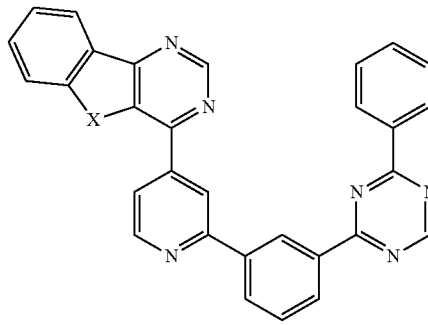

wherein Compound 73 is when X = O,
Compound 74 is when X = S, and
Compound 75 is when X = Se

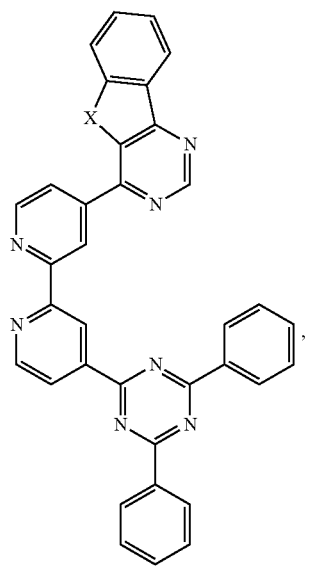

wherein Compound 76 is when X = O,
Compound 77 is when X = S, and
Compound 78 is when X = Se

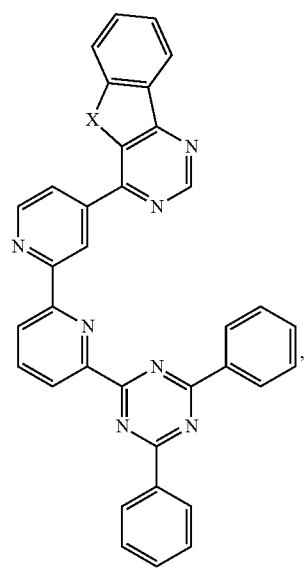

wherein Compound 79 is when X = O,
Compound 80 is when X = S, and
Compound 81 is when X = Se

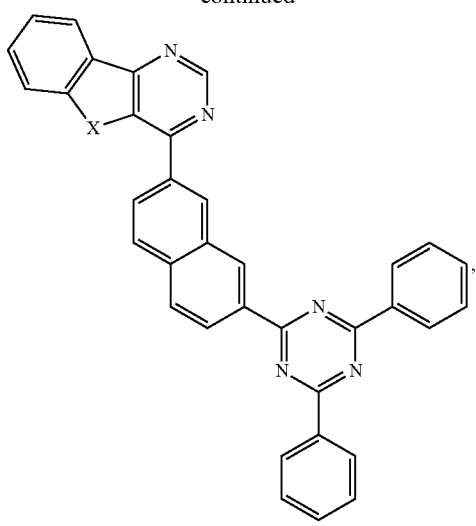

wherein Compound 82 is when X = O,
Compound 83 is when X = S, and
Compound 84 is when X = Se

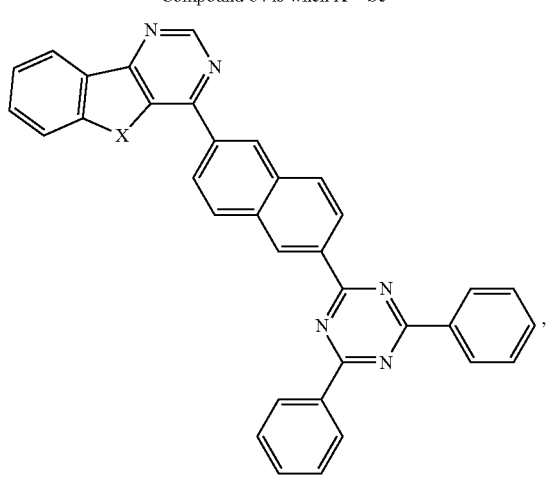

wherein Compound 85 is when X = O,
Compound 86 is when X = S, and
Compound 87 is when X = Se

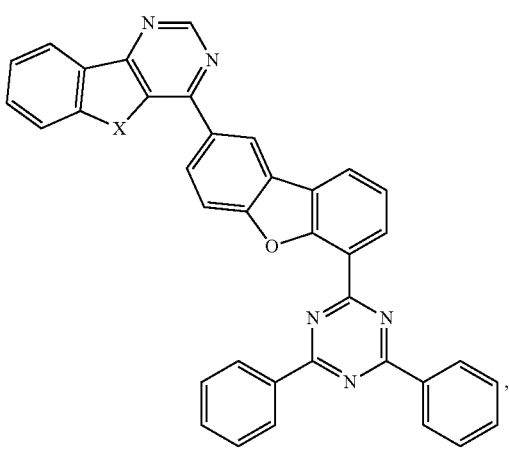

wherein Compound 88 is when X = O,
Compound 89 is when X = S, and
Compound 90 is when X = Se

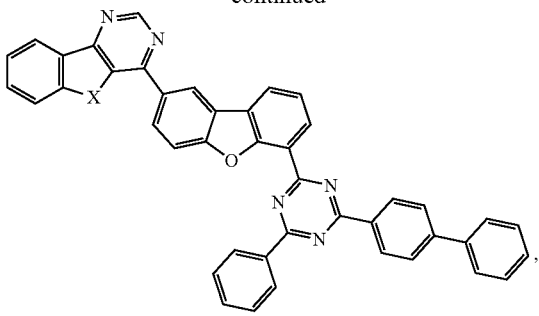

wherein Compound 91 is when X = O,
Compound 92 is when X = S, and
Compound 93 is when X = Se

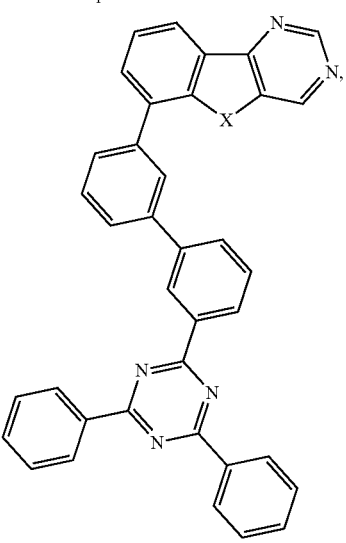

wherein Compound 94 is when X = O,
Compound 95 is when X = S, and
Compound 96 is when X = Se

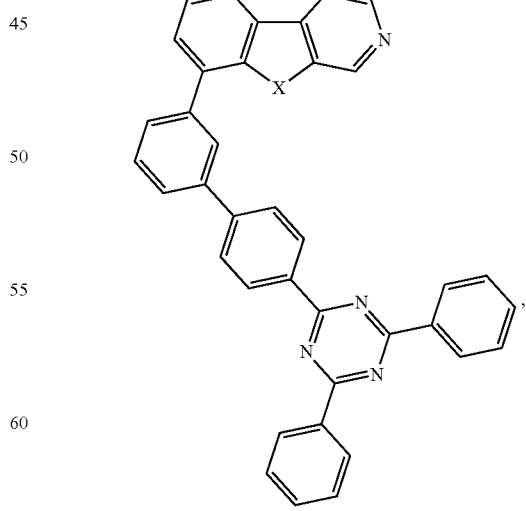

wherein Compound 97 is when X = O,
Compound 98 is when X = S, and
Compound 99 is when X = Se

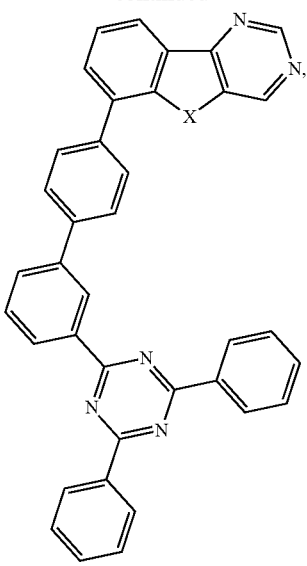

wherein Compound 100 is when X = O,
Compound 101 is when X = S, and
Compound 102 is when X = Se

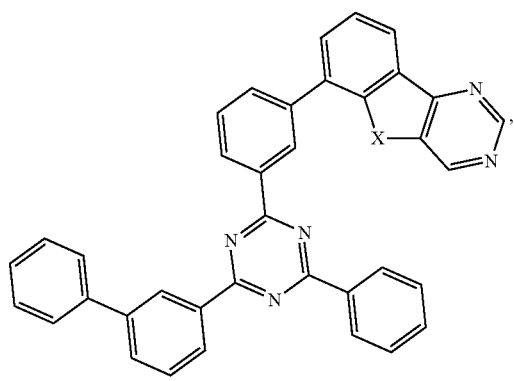

wherein Compound 103 is when X = O,
Compound 104 is when X = S, and
Compound 105 is when X = Se

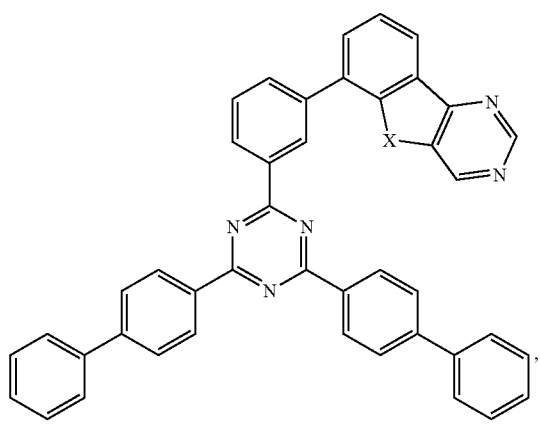

wherein Compound 106 is when X = O,
Compound 107 is when X = S, and
Compound 108 is when X = Se

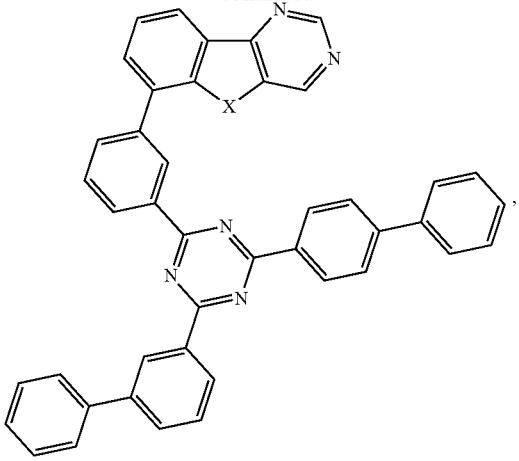

wherein Compound 109 is when X = O,
Compound 110 is when X = S, and
Compound 111 is when X = Se

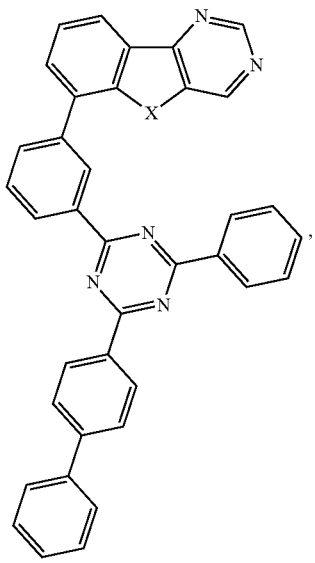

wherein Compound 112 is when X = O,
Compound 113 is when X = S, and
Compound 114 is when X = Se

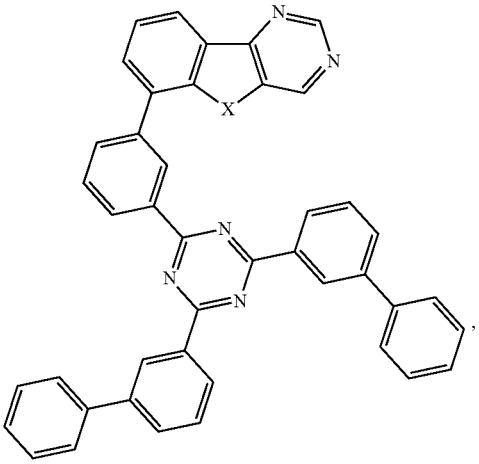

wherein Compound 115 is when X = O,
Compound 116 is when X = S, and
Compound 117 is when X = Se -continued

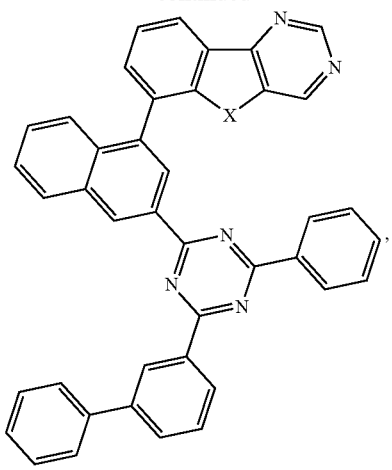

wherein Compound 118 is when X = O,
Compound 119 is when X = S, and
Compound 120 is when X = Se

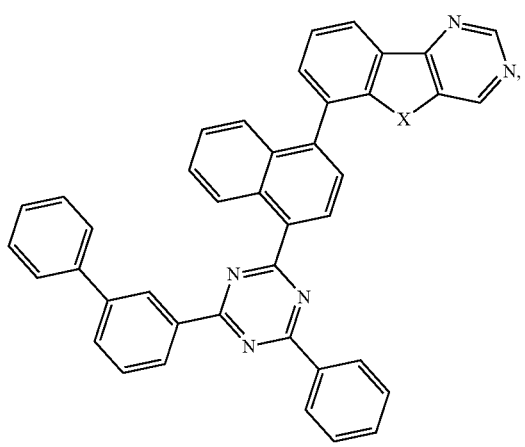

wherein Compound 121 is when X = O,
Compound 122 is when X = S, and
Compound 123 is when X = Se

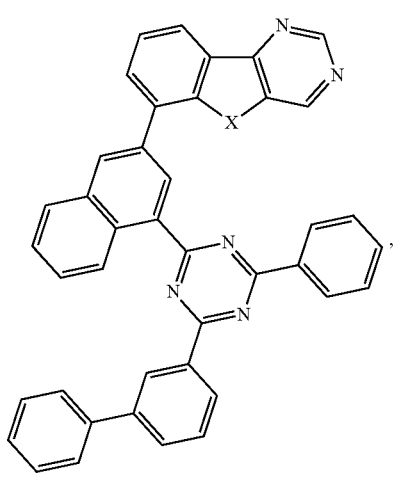

wherein Compound 124 is when X = O,
Compound 125 is when X = S, and
Compound 126 is when X = Se -continued

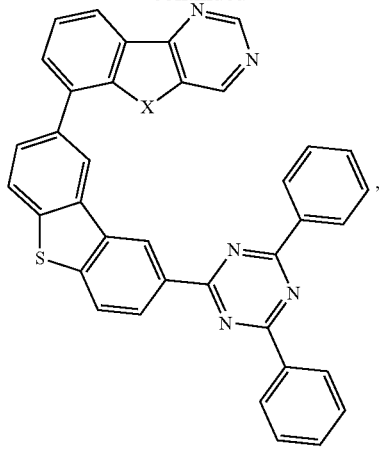

wherein Compound 127 is when X = O,
Compound 128 is when X = S, and
Compound 129 is when X = Se

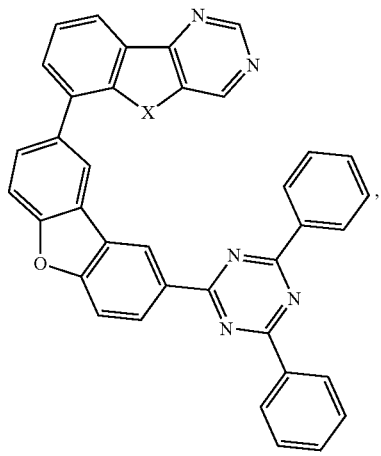

wherein Compound 130 is when X = O,
Compound 131 is when X = S, and
Compound 132 is when X = Se

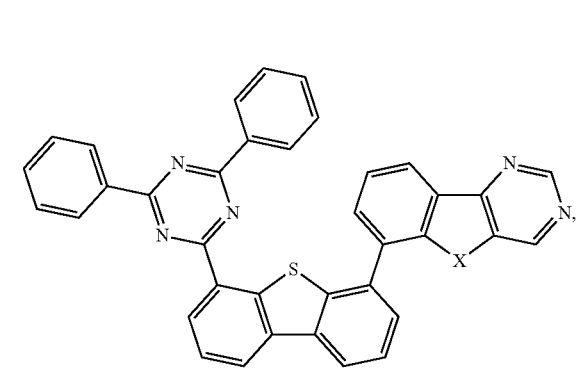

wherein Compound 133 is when X = O,
Compound 134 is when X = S, and
Compound 135 is when X = Se -continued

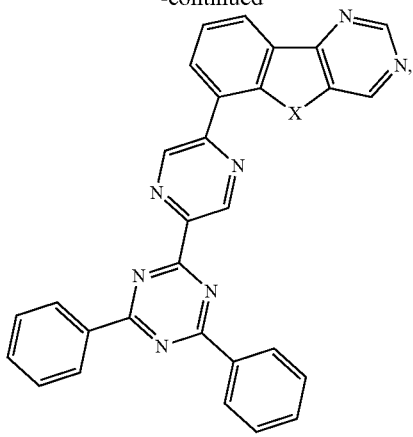

wherein Compound 136 is when X = O,
Compound 137 is when X = S, and
Compound 138 is when X = Se

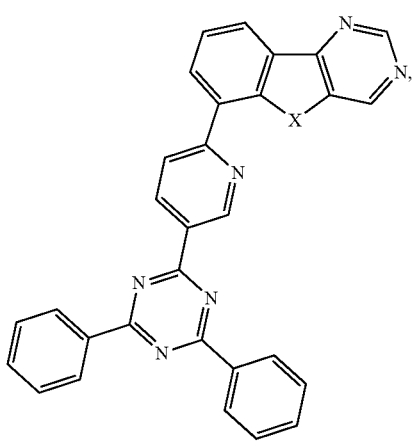

wherein Compound 139 is when X = O,
Compound 140 is when X = S, and
Compound 141 is when X = Se

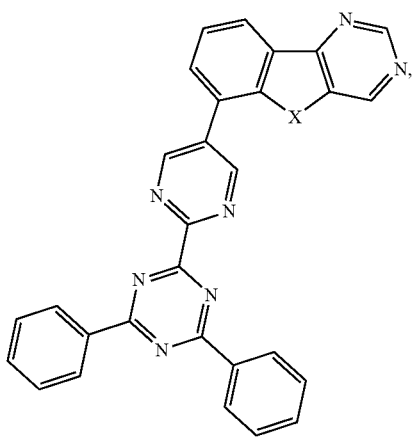

wherein Compound 142 is when X = O,
Compound 143 is when X = S, and
Compound 144 is when X = Se -continued

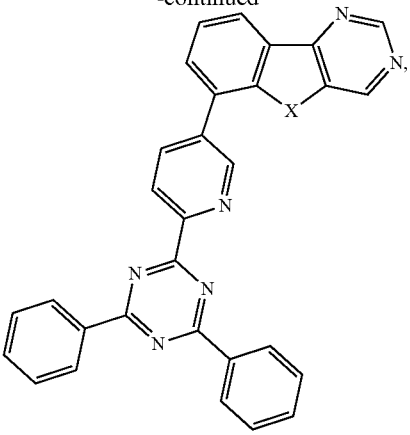

wherein Compound 145 is when X = O,
Compound 146 is when X = S, and
Compound 147 is when X = Se

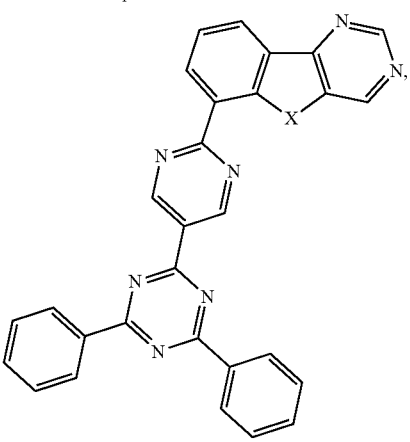

wherein Compound 148 is when X = O,
Compound 149 is when X = S, and
Compound 150 is when X = Se

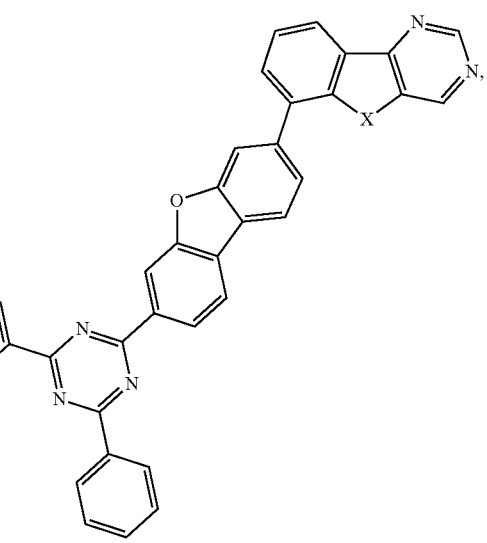

wherein Compound 151 is when X = O,
Compound 152 is when X = S, and
Compound 153 is when X = Se -continued

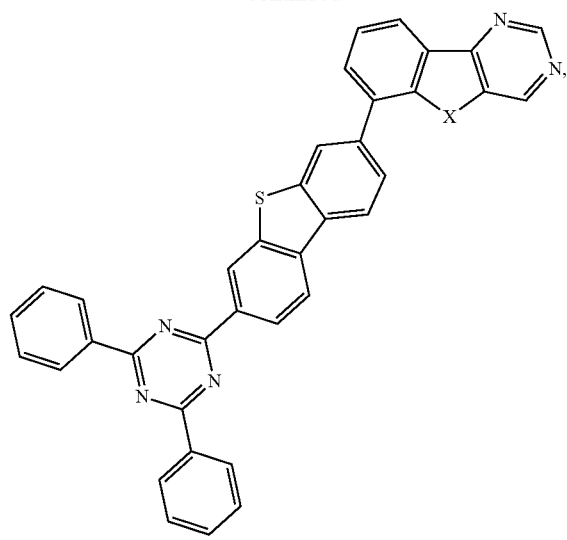

wherein Compound 154 is when X = O,
Compound 155 is when X = S, and
Compound 156 is when X = Se

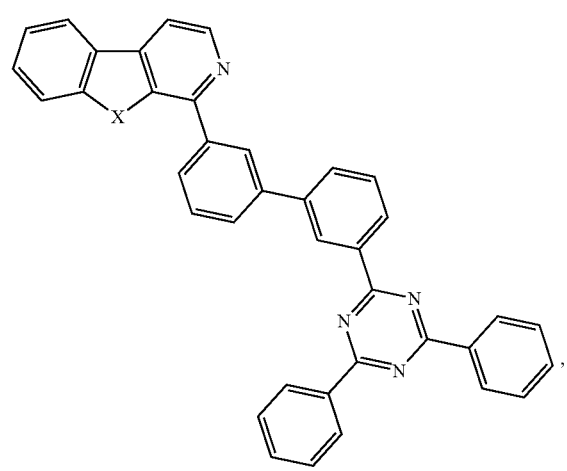

wherein Compound 157 is when X = O,
Compound 158 is when X = S, and
Compound 159 is when X = Se -continued

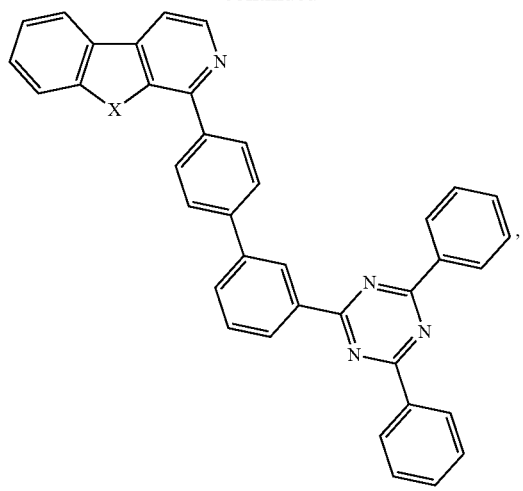

wherein Compound 160 is when X = O,
Compound 161 is when X = S, and
Compound 162 is when X = Se

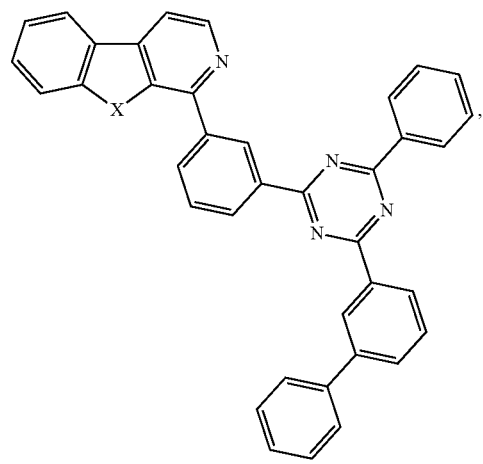

wherein Compound 163 is when X = O,
Compound 164 is when X = S, and
Compound 165 is when X = Se

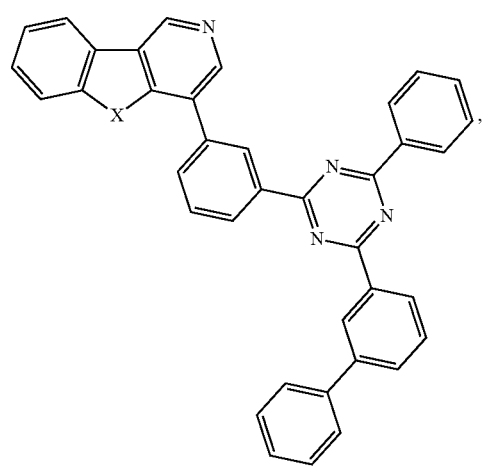

wherein Compound 166 is when X = O,
Compound 167 is when X = S, and
Compound 168 is when X = Se -continued

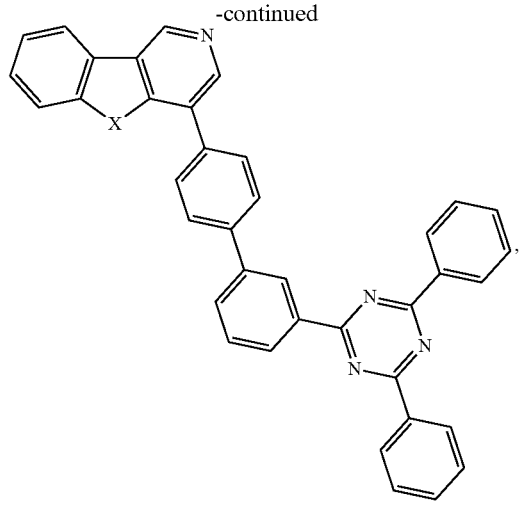

wherein Compound 169 is when X = O,
Compound 170 is when X = S, and
Compound 171 is when X = Se

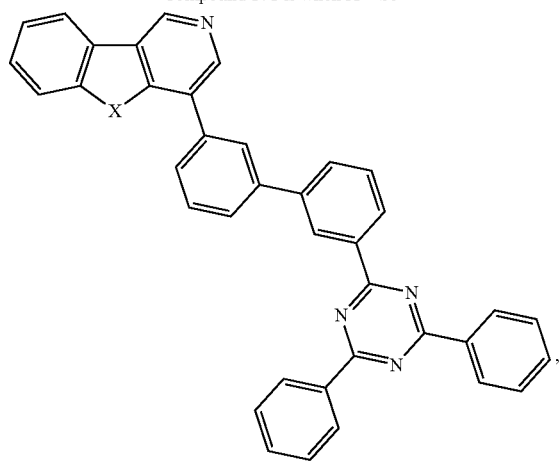

wherein Compound 172 is when X = O,
Compound 173 is when X = S, and
Compound 174 is when X = Se

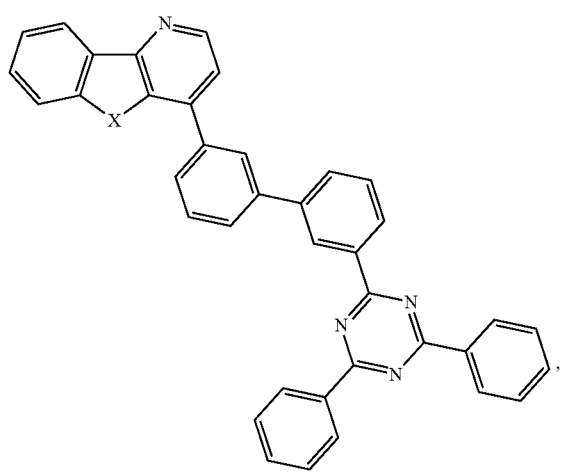

wherein Compound 175 is when X = O,
Compound 176 is when X = S, and
Compound 177 is when X = Se

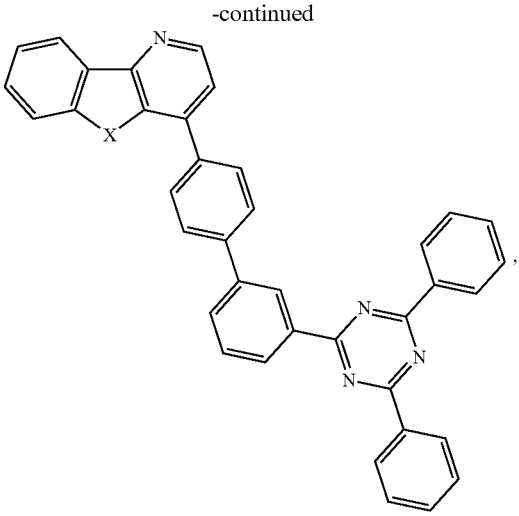

wherein Compound 178 is when X = O,
Compound 179 is when X = S, and
Compound 180 is when X = Se

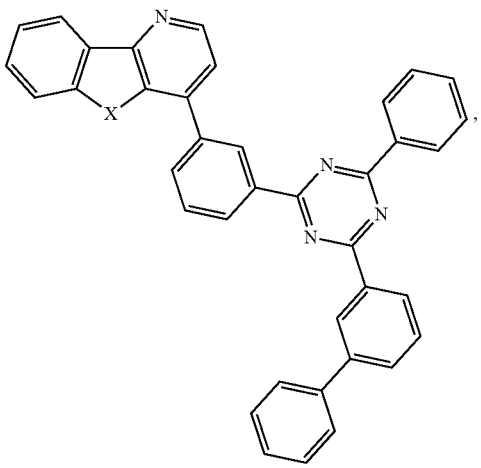

wherein Compound 181 is when X = O,
Compound 182 is when X = S, and
Compound 183 is when X = Se

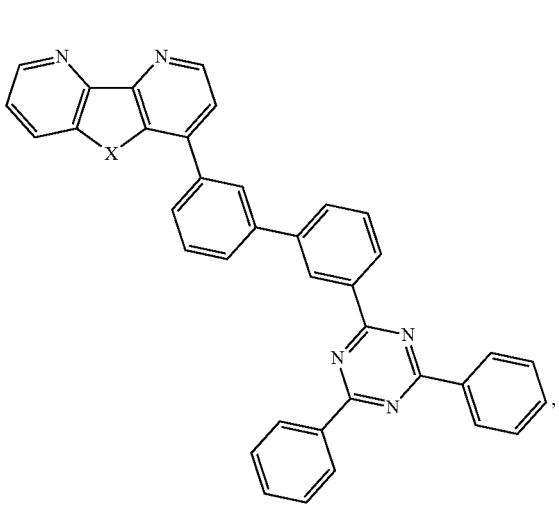

wherein Compound 184 is when X = O,
Compound 185 is when X = S, and
Compound 186 is when X = Se -continued

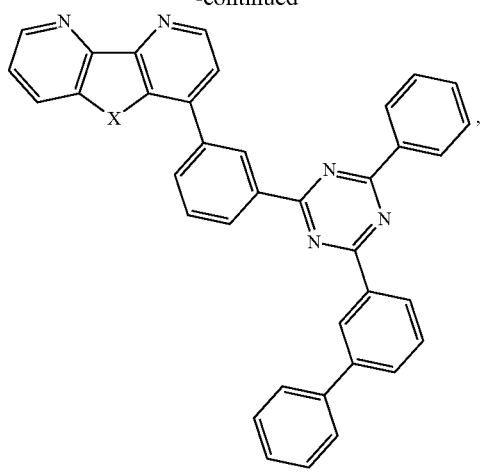

wherein Compound 187 is when X = O,
Compound 188 is when X = S, and
Compound 189 is when X = Se

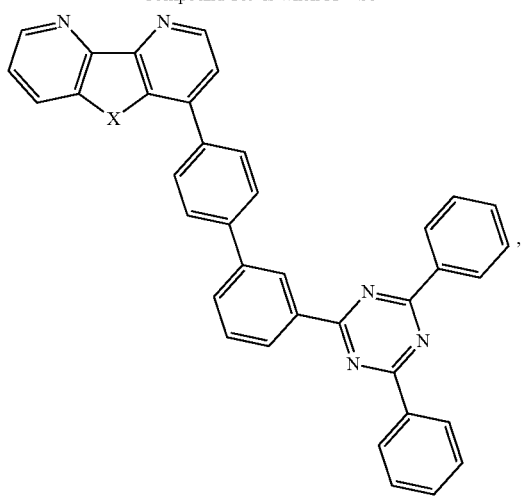

wherein Compound 190 is when X = O,
Compound 191 is when X = S, and
Compound 192 is when X = Se

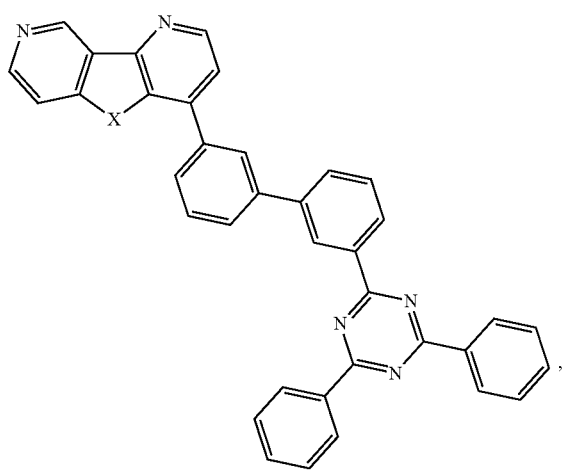

wherein Compound 193 is when X = O,
Compound 194 is when X = S, and
Compound 195 is when X = Se -continued

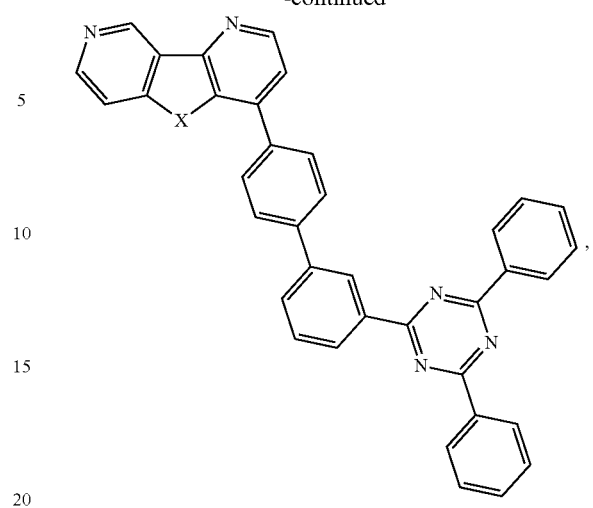

wherein Compound 196 is when X = O,
Compound 197 is when X = S, and
Compound 198 is when X = Se

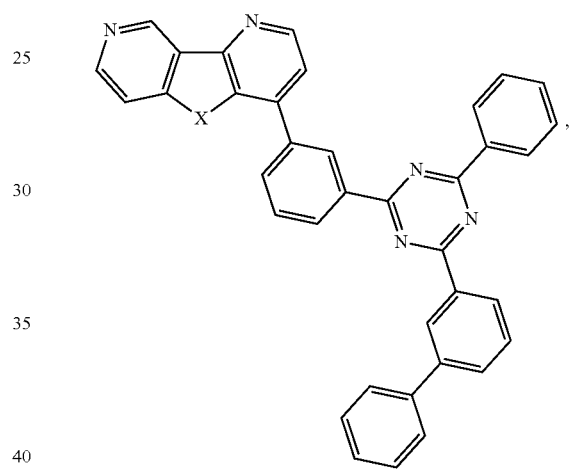

wherein Compound 199 is when X = O,
Compound 200 is when X = S, and
Compound 201 is when X = Se

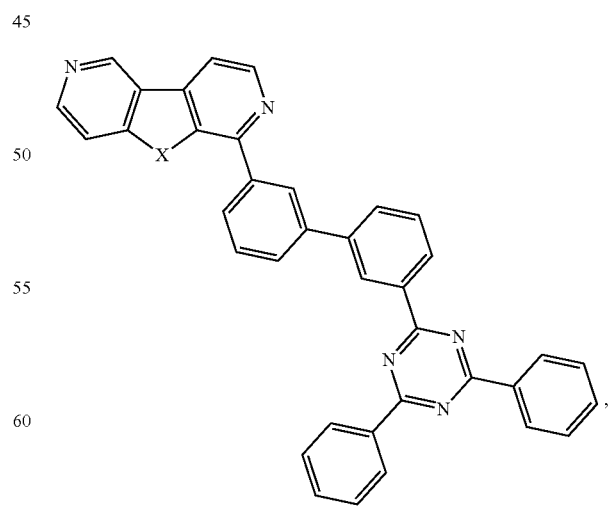

wherein Compound 202 is when X = O,
Compound 203 is when X = S, and
Compound 204 is when X = Se

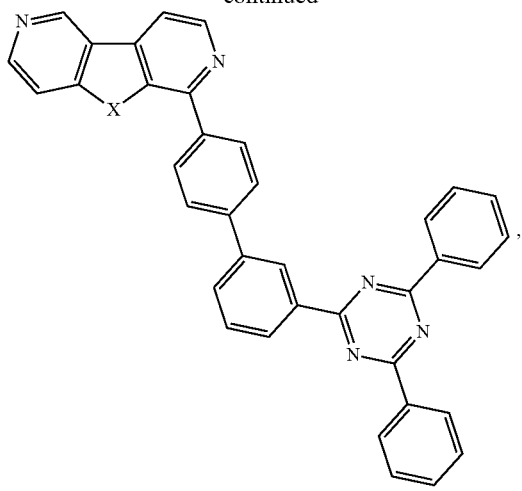

wherein Compound 205 is when X = O,
Compound 206 is when X = S, and
Compound 207 is when X = Se

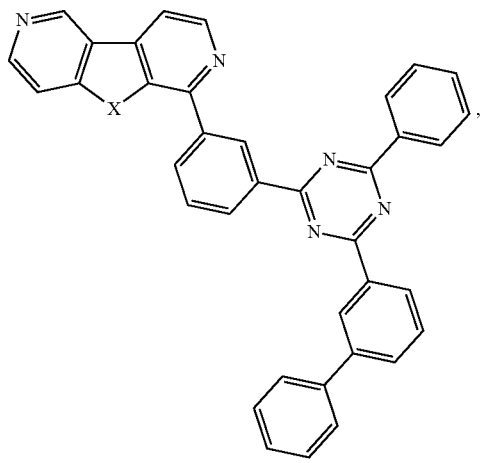

wherein Compound 208 is when X = O,
Compound 209 is when X = S, and
Compound 210 is when X = Se

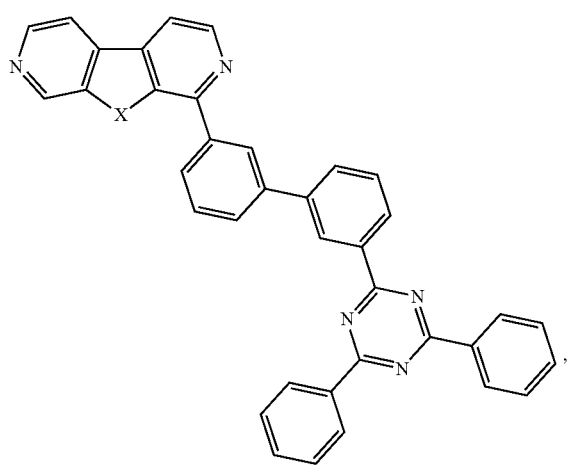

wherein Compound 211 is when X = O,
Compound 212 is when X = S, and
Compound 213 is when X = Se

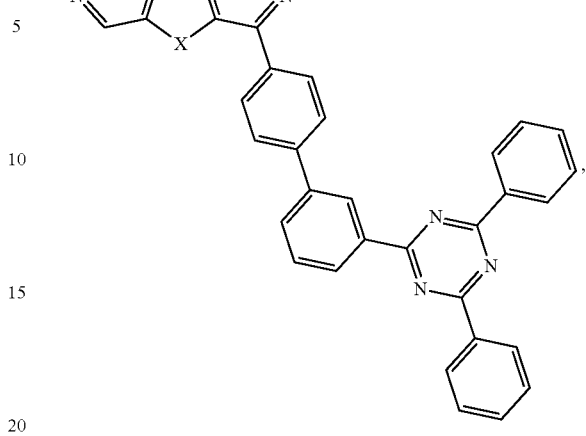

wherein Compound 214 is when X = O,
Compound 215 is when X = S, and
Compound 216 is when X = Se

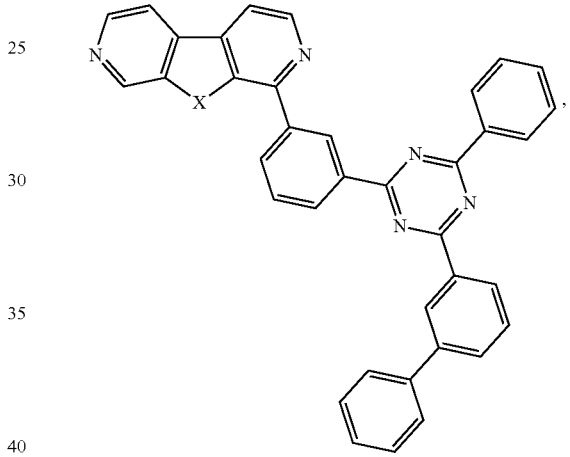

wherein Compound 217 is when X = O,
Compound 218 is when X = S, and
Compound 219 is when X = Se

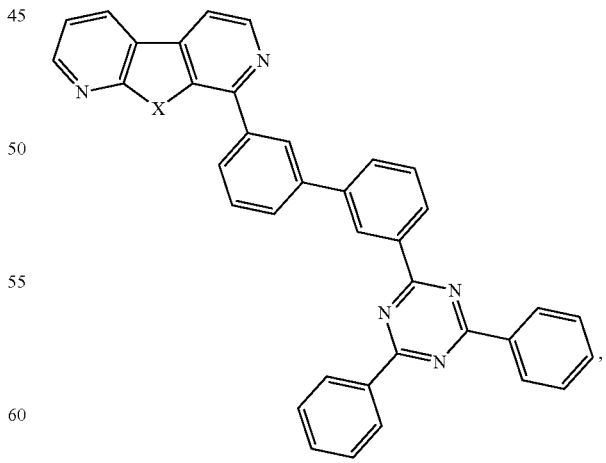

wherein Compound 220 is when X = O,
Compound 221 is when X = S, and
Compound 222 is when X = Se

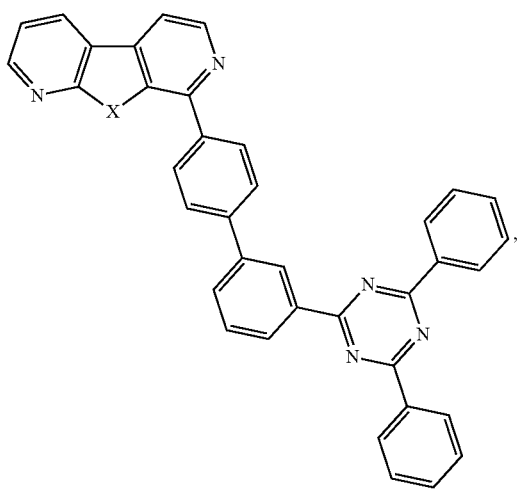

wherein Compound 223 is when X = O,
Compound 224 is when X = S, and
Compound 225 is when X = Se

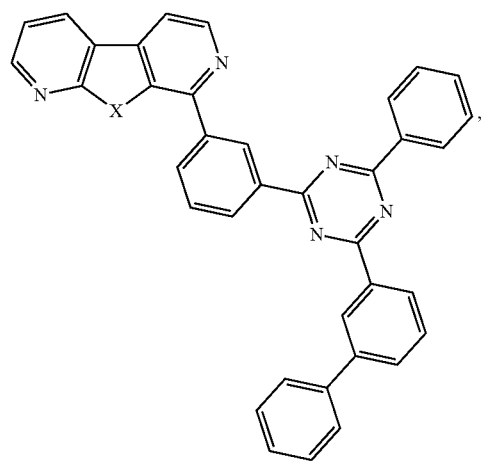

wherein Compound 226 is when X = O,
Compound 227 is when X = S, and
Compound 228 is when X = Se

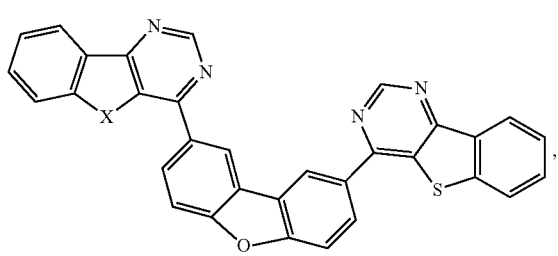

wherein Compound 229 is when X = O,
Compound 230 is when X = S, and
Compound 231 is when X = Se

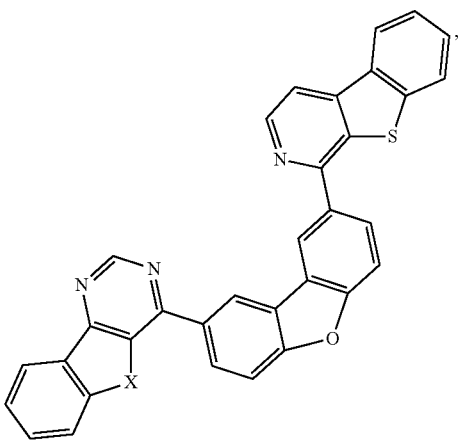

wherein Compound 232 is when X = O,
Compound 233 is when X = S, and
Compound 234 is when X = Se

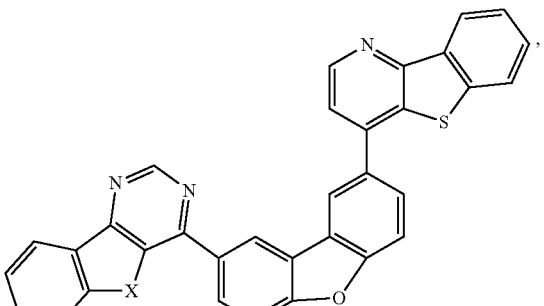

wherein Compound 235 is when X = O,
Compound 236 is when X = S, and
Compound 237 is when X = Se

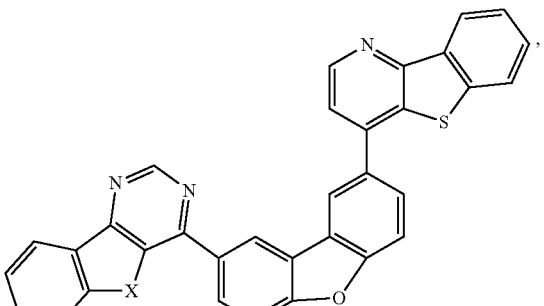

wherein Compound 238 is when X = O,
Compound 239 is when X = S, and
Compound 240 is when X = Se -continued

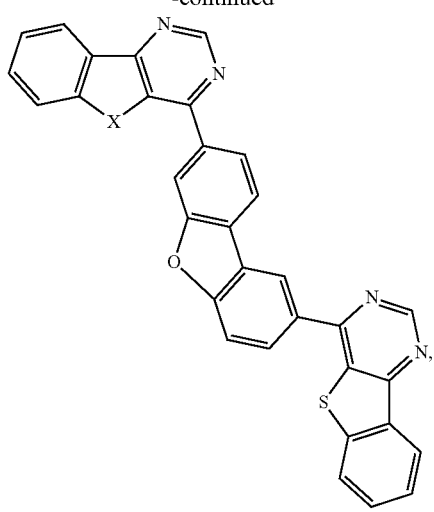

wherein Compound 241 is when X = O,
Compound 242 is when X = S, and
Compound 243 is when X = Se

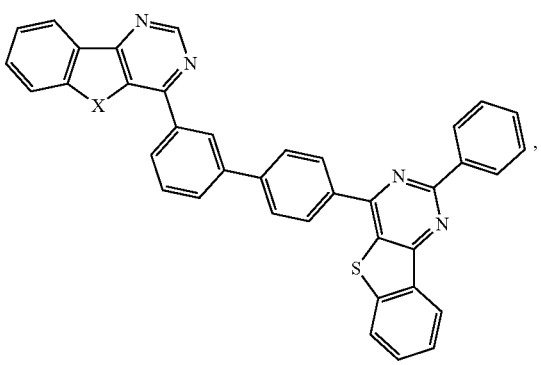

wherein Compound 244 is when X = O,
Compound 245 is when X = S, and
Compound 246 is when X = Se

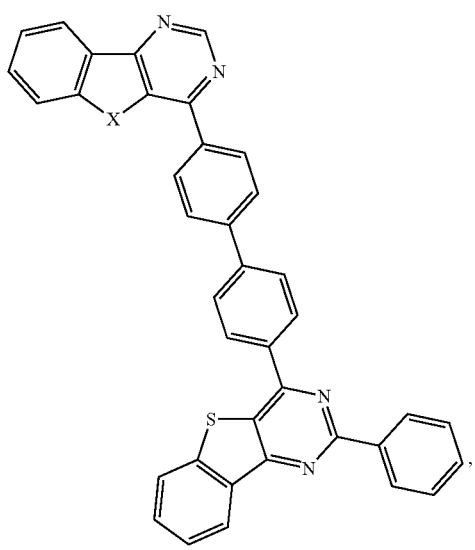

wherein Compound 247 is when X = O,
Compound 248 is when X = S, and
Compound 249 is when X = Se -continued

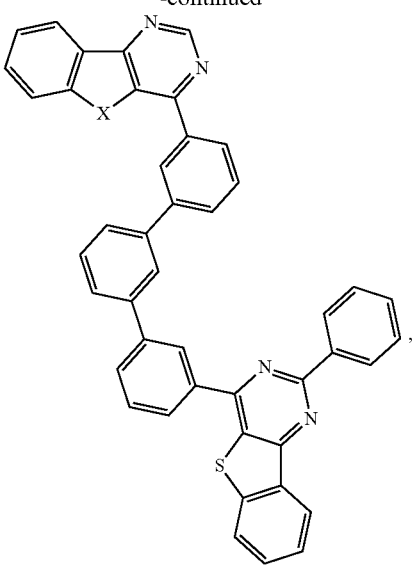

wherein Compound 250 is when X = O,
Compound 251 is when X = S, and
Compound 252 is when X = Se

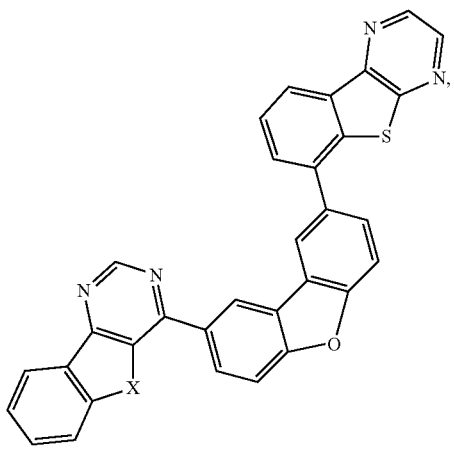

wherein Compound 253 is when X = O,
Compound 254 is when X = S, and
Compound 255 is when X = Se

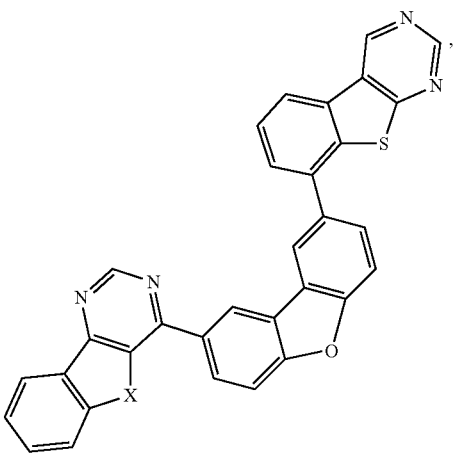

wherein Compound 256 is when X = O,
Compound 257 is when X = S, and
Compound 258 is when X = Se

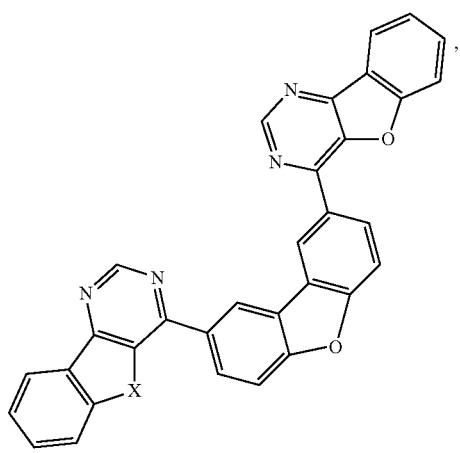

wherein Compound 259 is when X = O,
Compound 260 is when X = S, and
Compound 261 is when X = Se

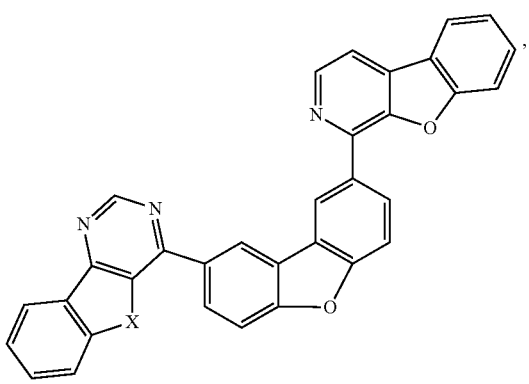

wherein Compound 262 is when X = O,
Compound 263 is when X = S, and
Compound 264 is when X = Se

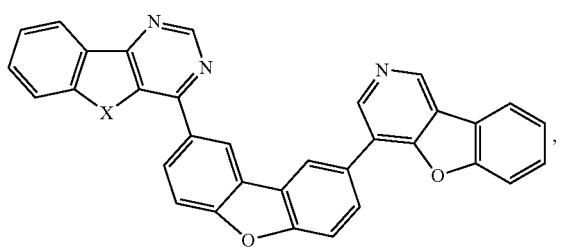

wherein Compound 265 is when X = O,
Compound 266 is when X = S, and
Compound 267 is when X = Se

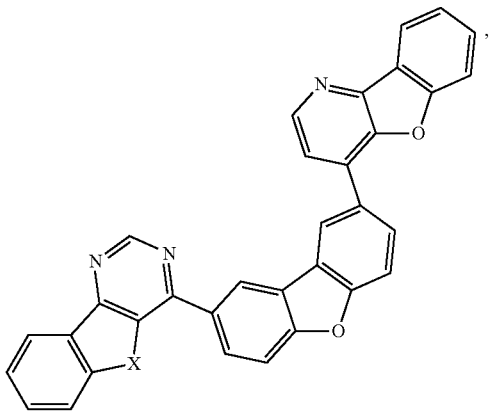

wherein Compound 268 is when X = O,
Compound 269 is when X = S, and
Compound 270 is when X = Se

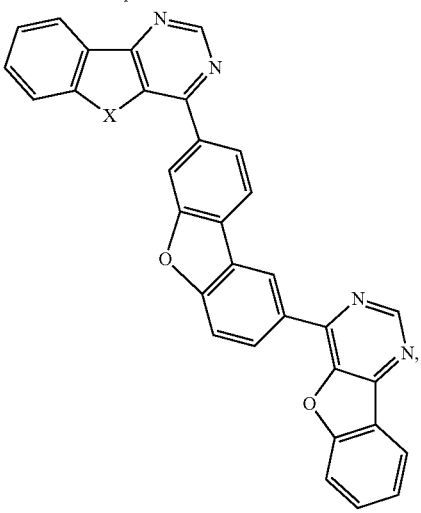

wherein Compound 271 is when X = O,
Compound 272 is when X = S, and
Compound 273 is when X = Se

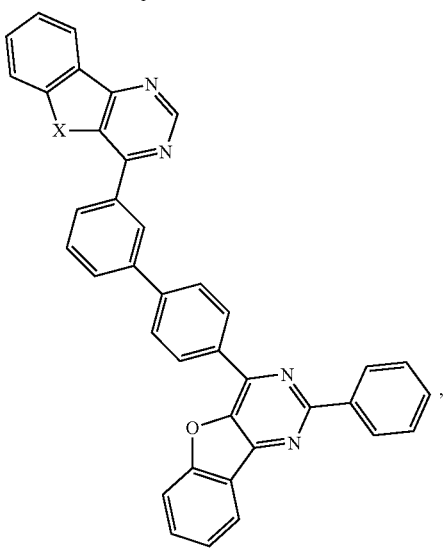

wherein Compound 274 is when X = O,
Compound 275 is when X = S, and
Compound 276 is when X = Se

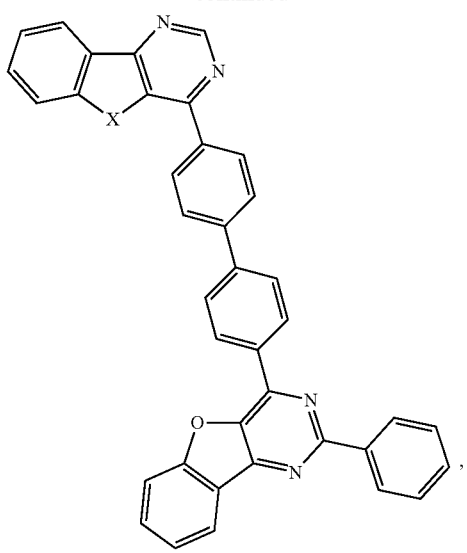

wherein Compound 277 is when X = O,
Compound 278 is when X = S, and
Compound 279 is when X = Se

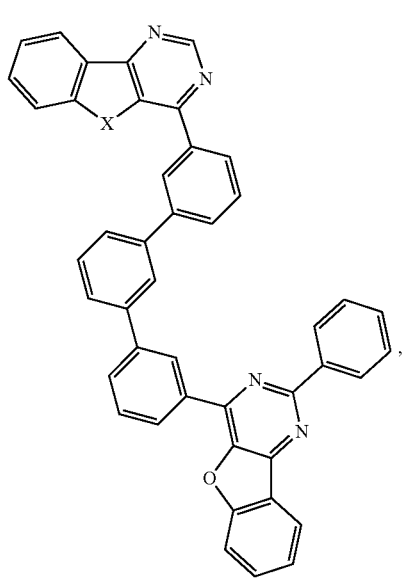

wherein Compound 280 is when X = O,
Compound 281 is when X = S, and
Compound 282 is when X = Se

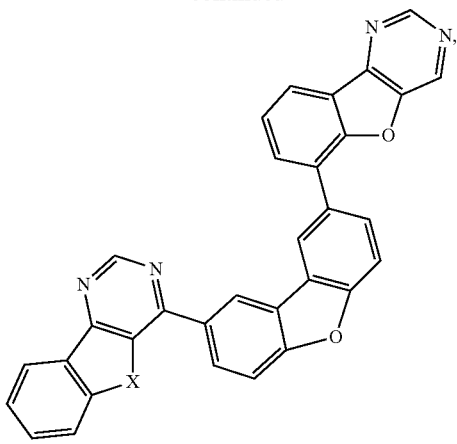

wherein Compound 283 is when X = O,
Compound 284 is when X = S, and
Compound 285 is when X = Se

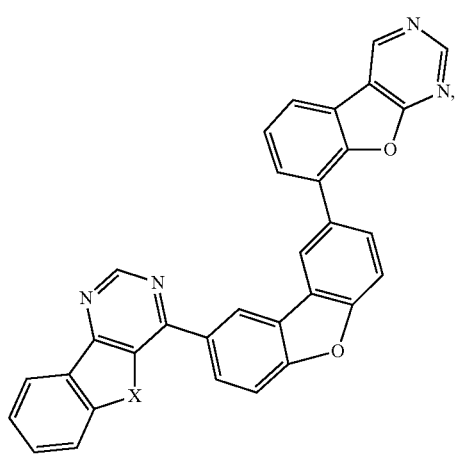

wherein Compound 286 is when X = O,
Compound 287 is when X = S, and
Compound 288 is when X = Se

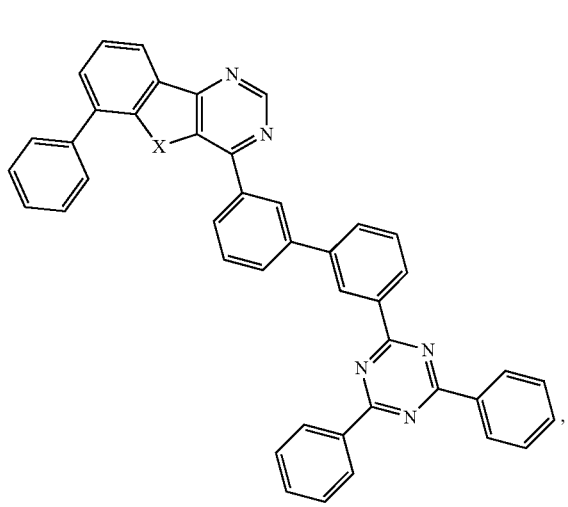

wherein Compound 289 is when X = O,
Compound 290 is when X = S, and
Compound 291 is when X = Se -continued

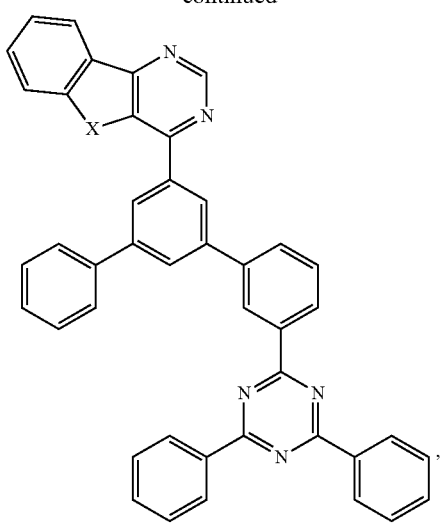

wherein Compound 292 is when X = O,
Compound 293 is when X = S, and
Compound 294 is when X = Se

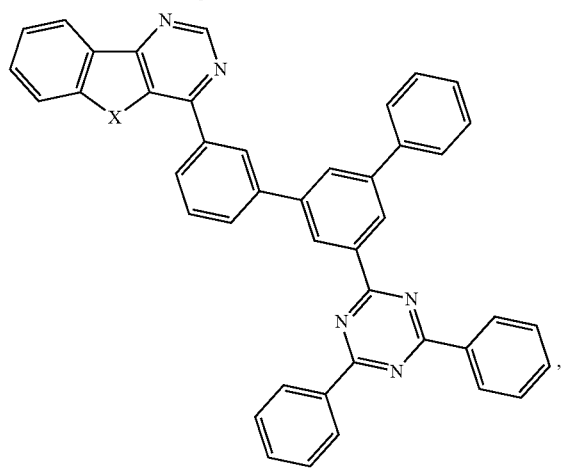

wherein Compound 295 is when X = O,
Compound 296 is when X = S, and
Compound 297 is when X = Se

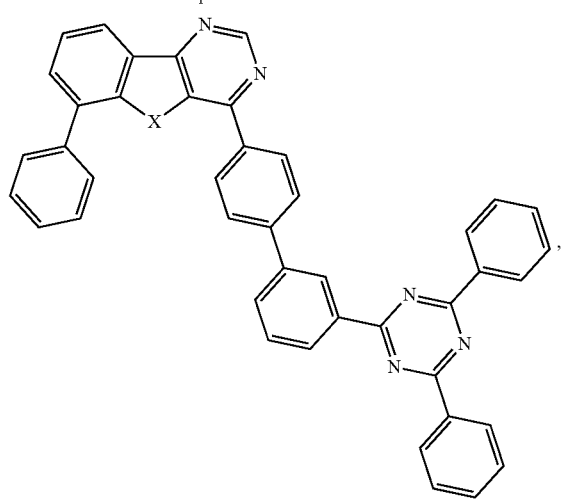

wherein Compound 298 is when X = O,
Compound 299 is when X = S, and
Compound 300 is when X = Se -continued

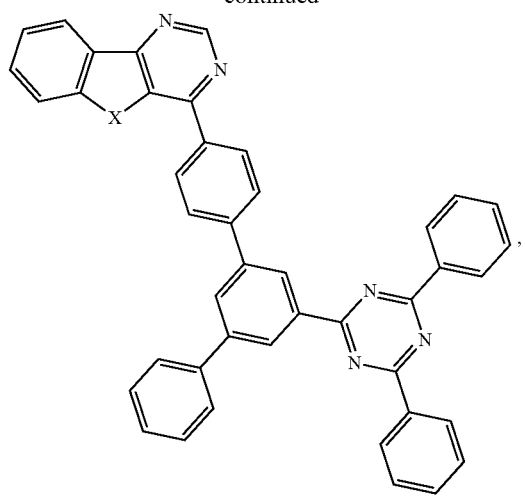

wherein Compound 301 is when X = O,
Compound 302 is when X = S, and
Compound 303 is when X = Se

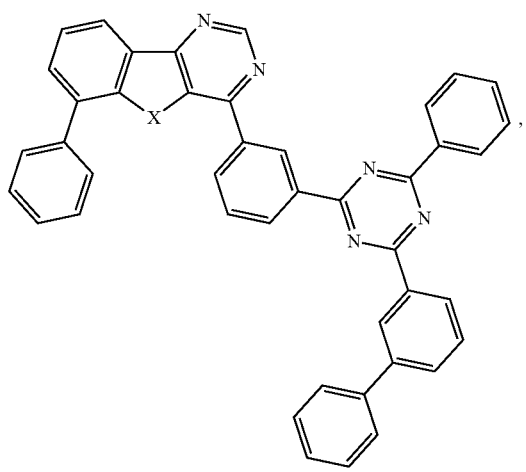

wherein Compound 304 is when X = O,
Compound 305 is when X = S, and
Compound 306 is when X = Se

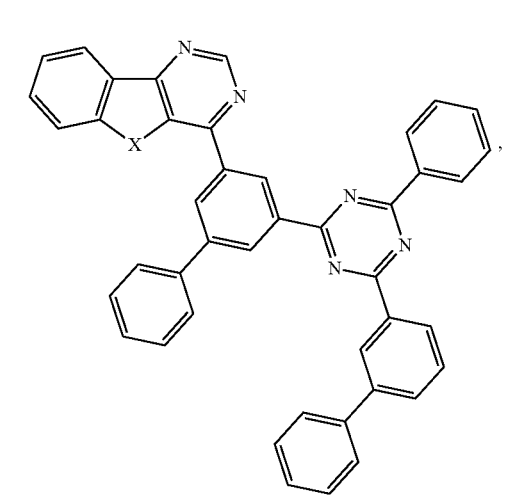

wherein Compound 307 is when X = O,
Compound 308 is when X = S, and
Compound 309 is when X = Se -continued

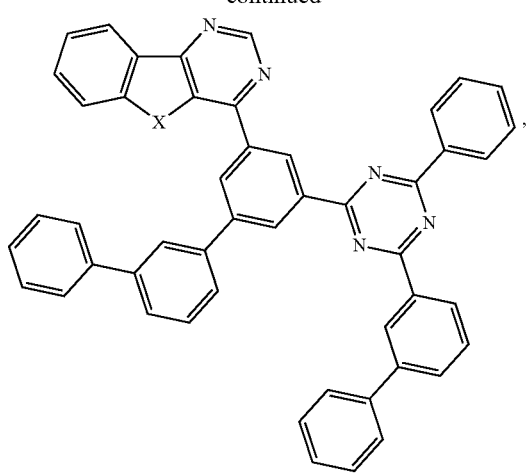

wherein Compound 310 is when X = O,
Compound 311 is when X = S, and
Compound 312 is when X = Se

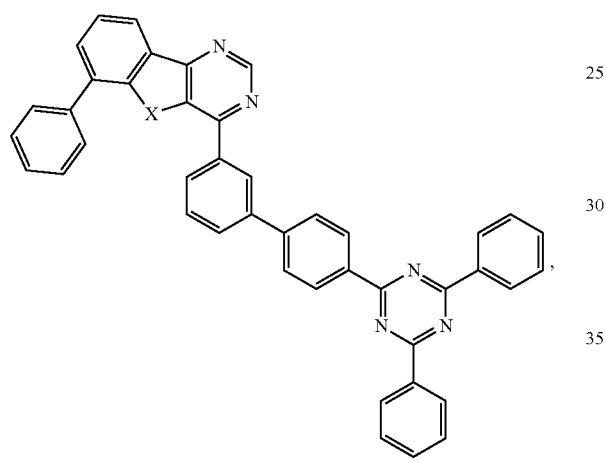

wherein Compound 313 is when X = O,
Compound 314 is when X = S, and
Compound 315 is when X = Se

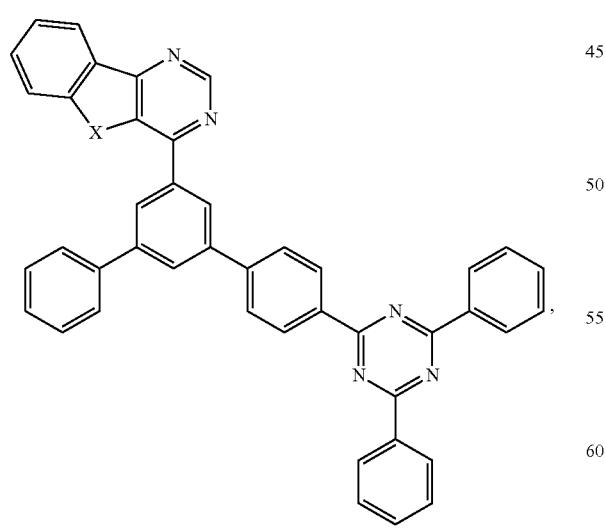

wherein Compound 316 is when X = O,
Compound 317 is when X = S, and
Compound 318 is when X = Se -continued

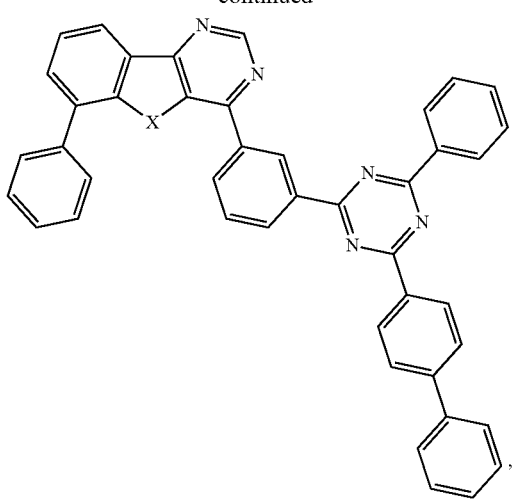

wherein Compound 319 is when X = O,
Compound 320 is when X = S, and
Compound 321 is when X = Se

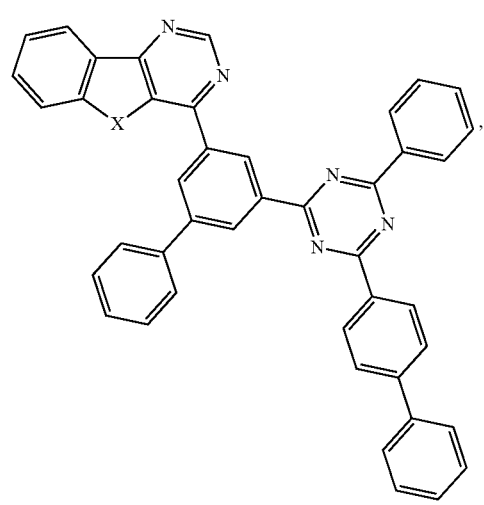

wherein Compound 322 is when X = O,
Compound 323 is when X = S, and
Compound 324 is when X = Se -continued
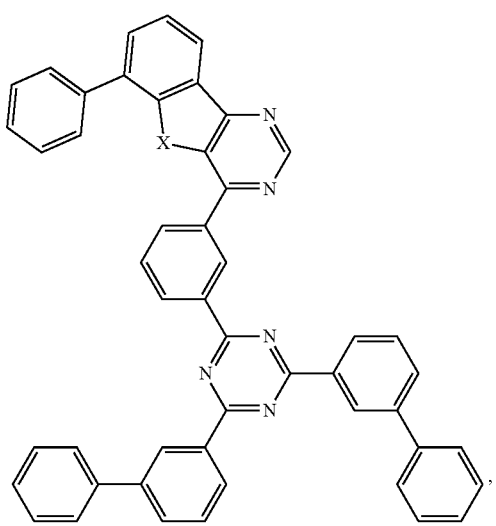
wherein Compound 325 is when X = O,
Compound 326 is when X = S, and
Compound 327 is when X = Se
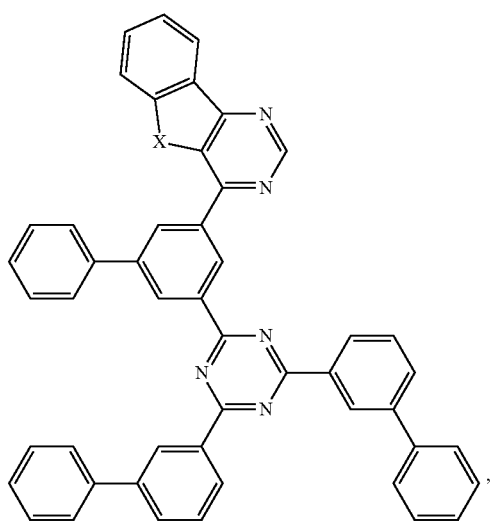
wherein Compound 328 is when X = O,
Compound 329 is when X = S, and
Compound 330 is when X = Se
-continued
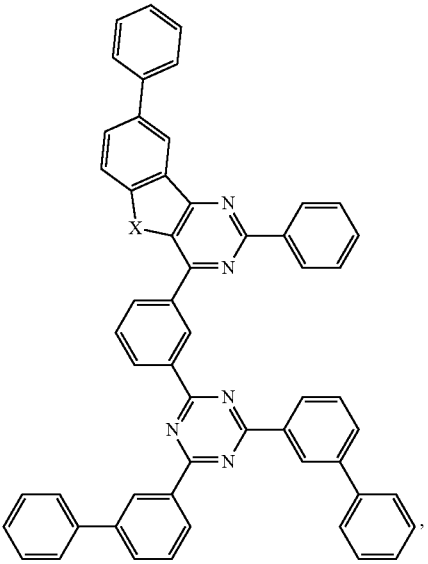
wherein Compound 331 is when X = O,
Compound 332 is when X = S, and
Compound 333 is when X = Se
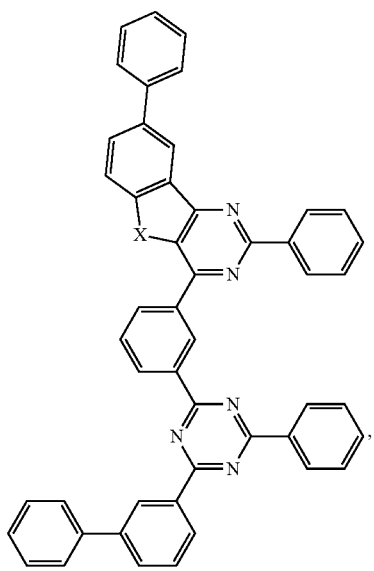
wherein Compound 334 is when X = O,
Compound 335 is when X = S, and
Compound 336 is when X = Se

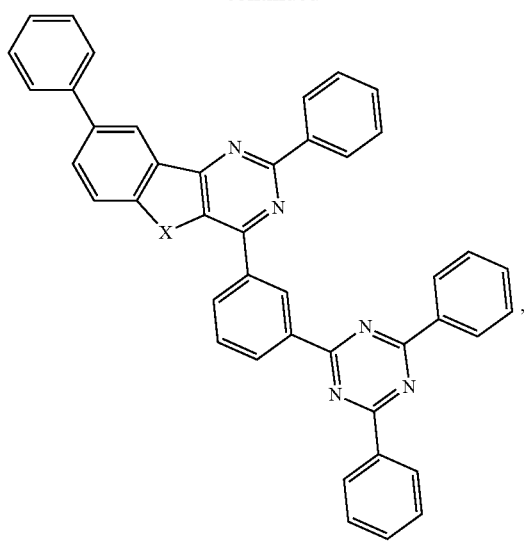

wherein Compound 337 is when X = O,
Compound 338 is when X = S, and
Compound 339 is when X = Se

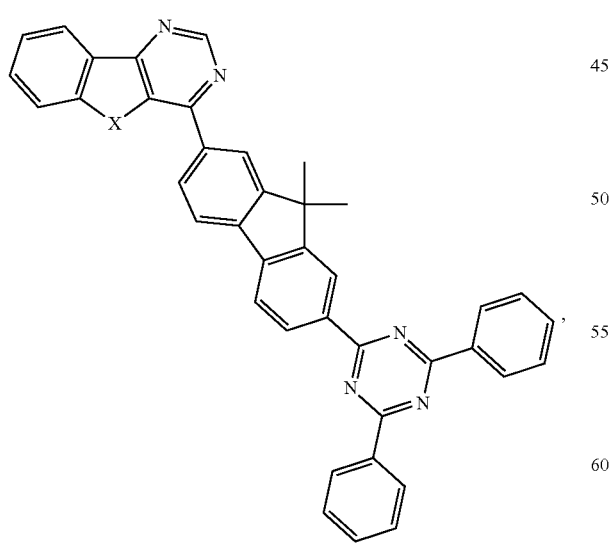

wherein Compound 340 is when X = O,
Compound 341 is when X = S, and
Compound 342 is when X = Se

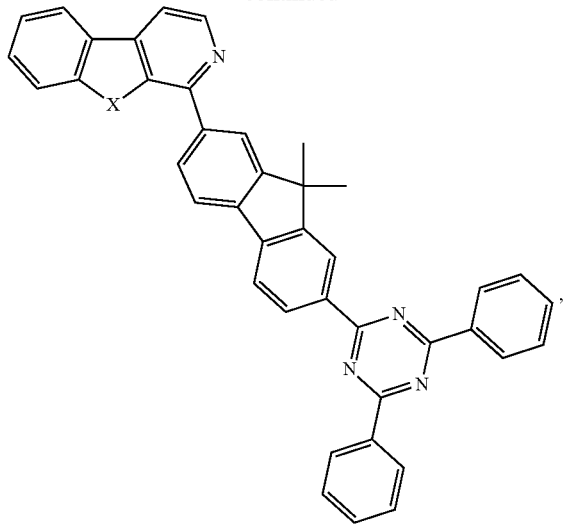

wherein Compound 343 is when X = O,
Compound 344 is when X = S, and
Compound 345 is when X = Se

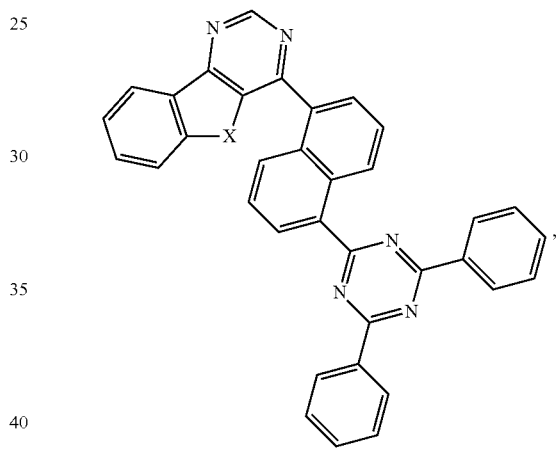

wherein Compound 346 is when X = O,
Compound 347 is when X = S, and
Compound 348 is when X = Se

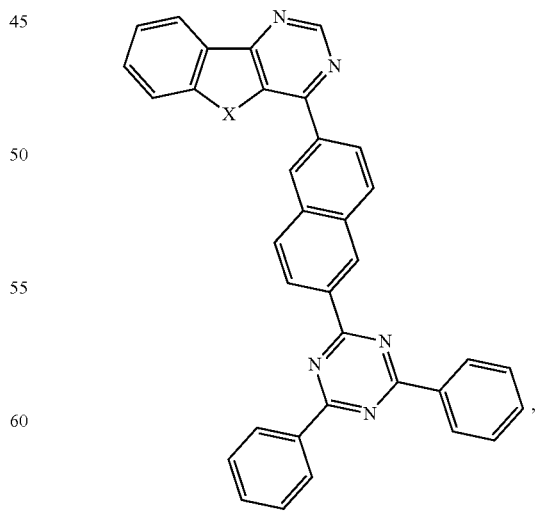

wherein Compound 349 is when X = O,
Compound 350 is when X = S, and
Compound 351 is when X = Se -continued

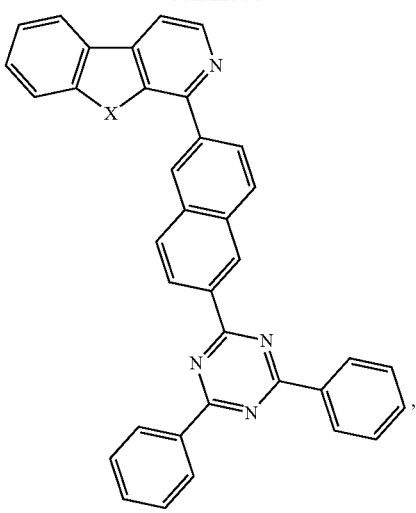

wherein Compound 352 is when X = O,
Compound 353 is when X = S, and
Compound 354 is when X = Se

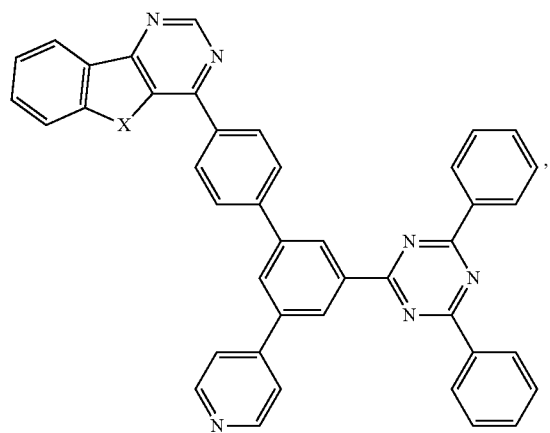

wherein Compound 355 is when X = O,
Compound 356 is when X = S, and
Compound 357 is when X = Se

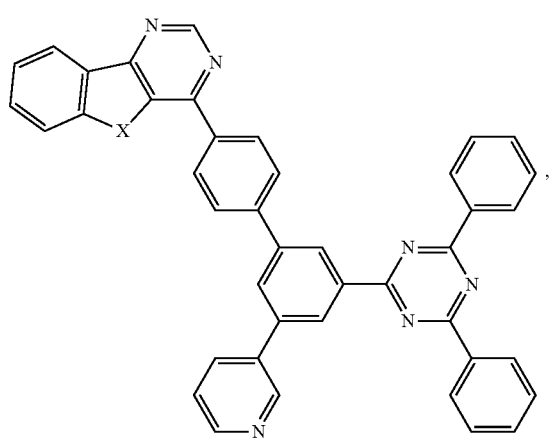

wherein Compound 358 is when X = O,
Compound 359 is when X = S, and
Compound 360 is when X = Se -continued

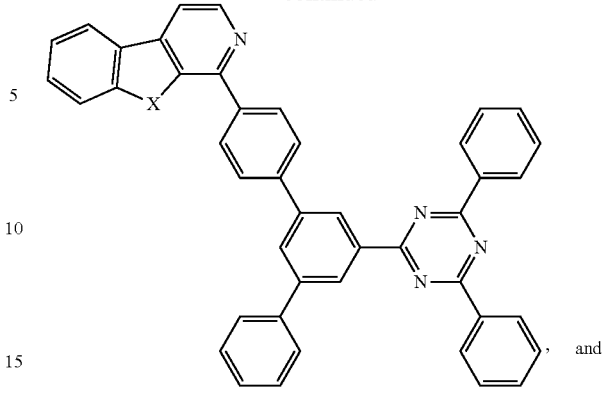

wherein Compound 361 is when X = O,
Compound 362 is when X = S, and
Compound 363 is when X = Se

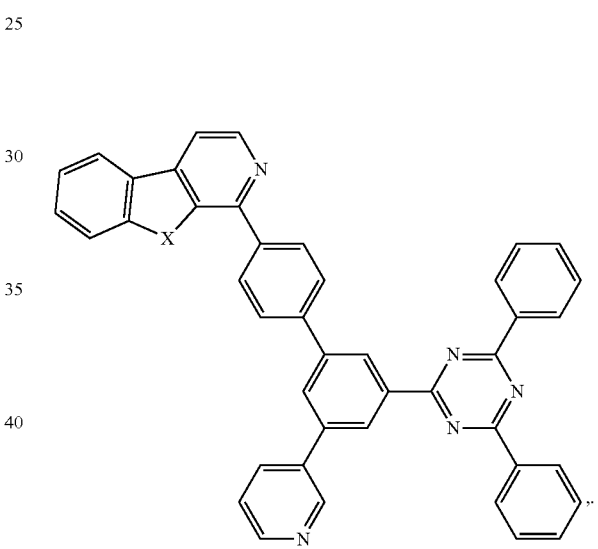

wherein Compound 364 is when X = O,
Compound 365 is when X = S, and
Compound 366 is when X = Se According to another aspect of the present disclosure, a device comprising one or more organic light emitting devices is disclosed. According to some embodiments, of the device, at least one of the one or more organic light emitting devices comprises: an anode; a cathode; and an organic layer, disposed between the anode and the cathode. The organic layer comprises a compound having a structure according to Formula I and its variations as described herein.

According to an embodiment of the device, the organic layer is an emissive layer and the compound of Formula I is a host.

According to an embodiment of the device, the organic layer further comprises a phosphorescent emissive dopant. The phosphorescent emissive dopant can be a transition metal complex having at least one ligand or part of the ligand if the ligand is more than bidentate selected from the group consisting of:

-continued
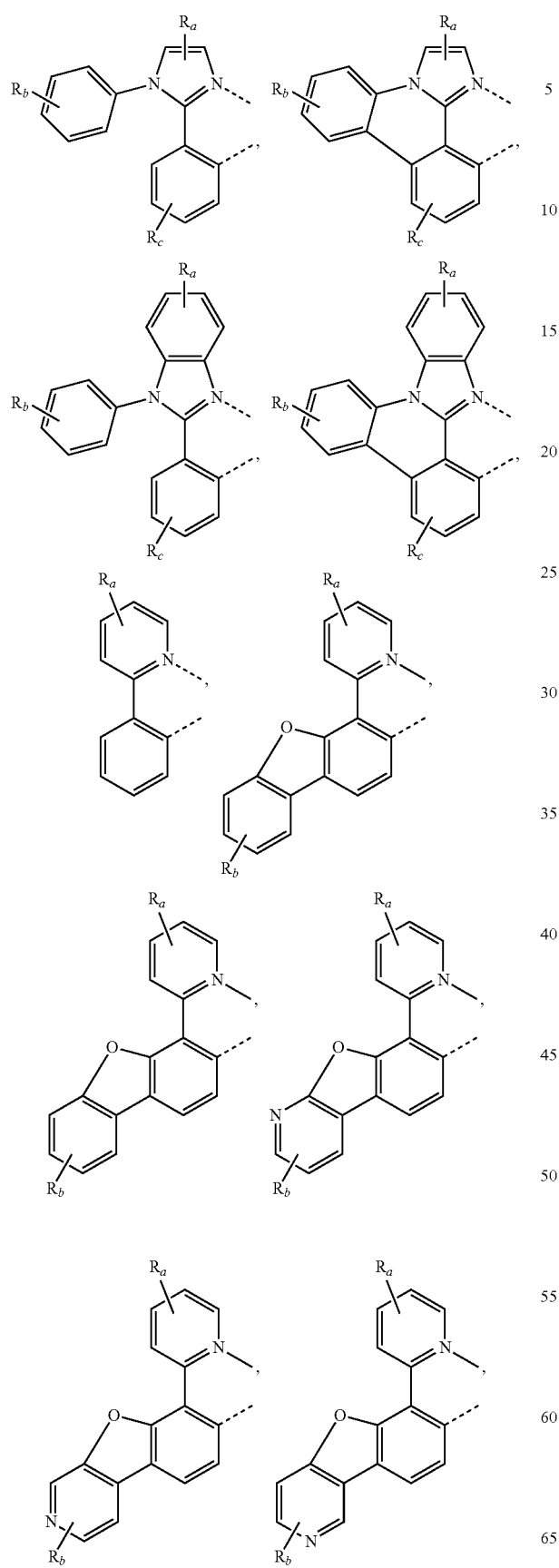
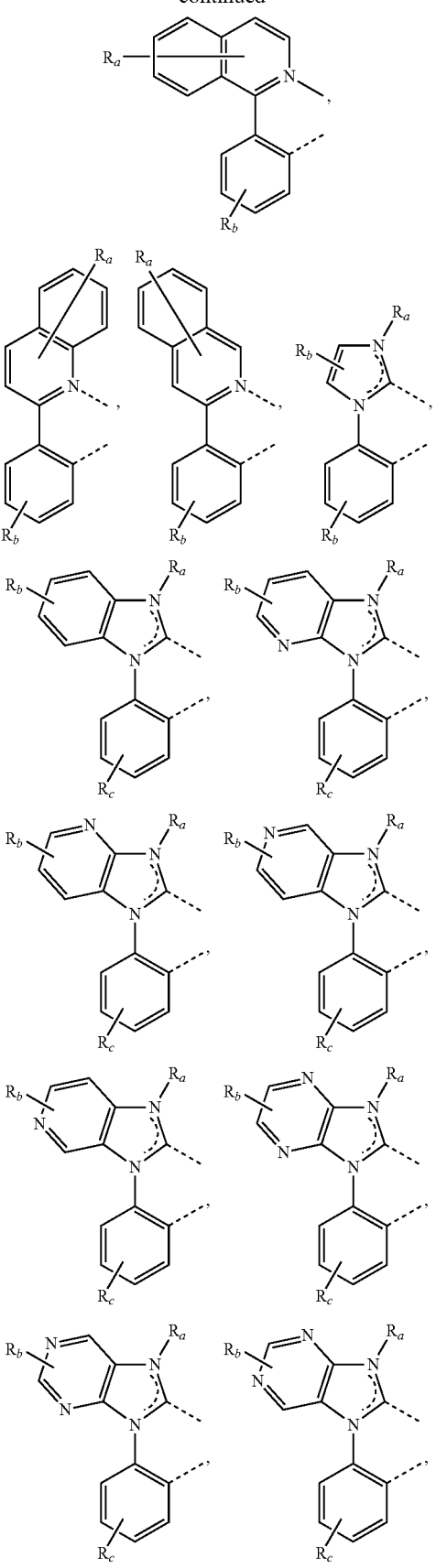

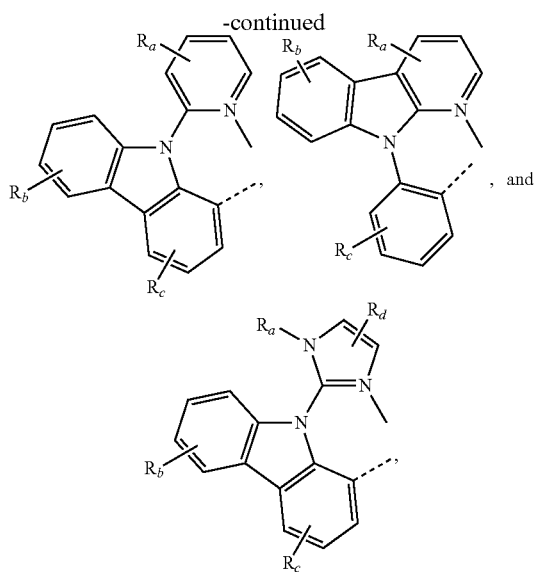

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In one embodiment of the device, the device is selected from the group consisting of a consumer product, an electronic component module, an organic light-emitting device, and a lighting panel.

In another embodiment of the device, the organic layer is a blocking layer and the compound of Formula I is a blocking material in the organic layer.

In some embodiments of the device, the organic layer is an electron transport layer and the compound of Formula I is an electron transporting material in the organic layer.

According to another aspect of the present disclosure, a formulation comprising a compound having a structure according to Formula I and its variations as described herein is also disclosed. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

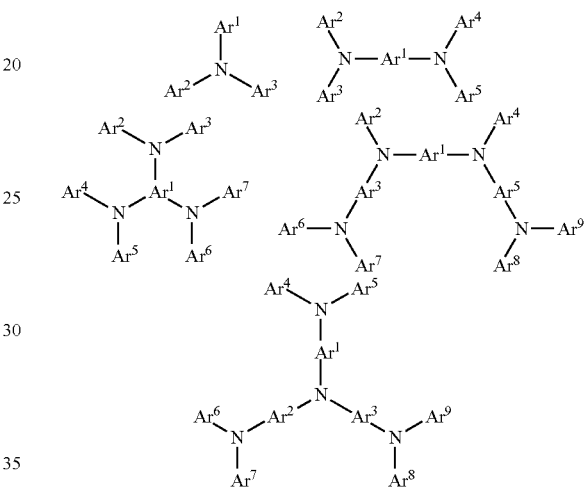

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

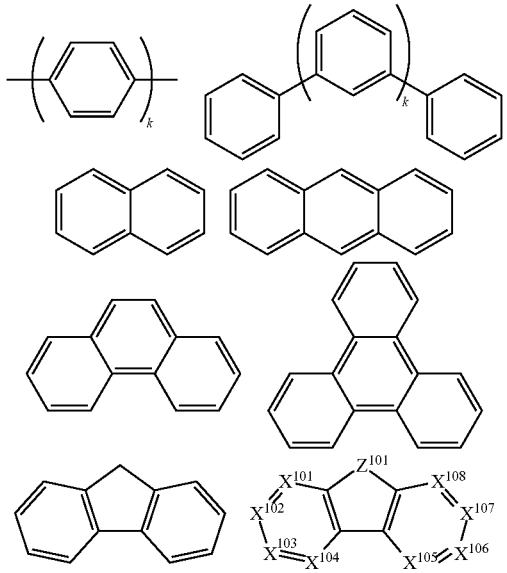

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

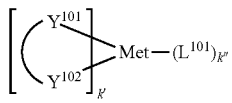

wherein Met is a metal, which can have an atomic weight greater than 40; $(Y^{101}-Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}-Y^x)$ is a 2-phenylpyridine derivative. In another aspect, $(Y^{101}-Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

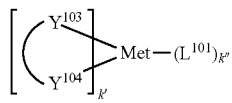

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

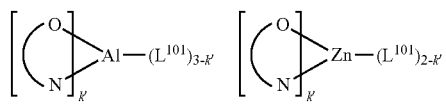

wherein (O—N) is a bidentate ligand, having metal coordinated to atoms O and N.

In another aspect, Met is selected from Ir and Pt. In a further aspect, $(Y^{103}-Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

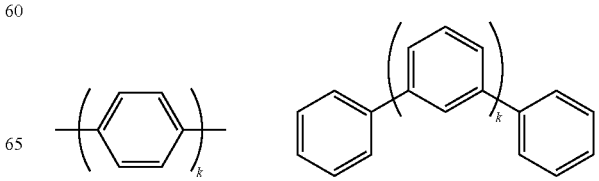

-continued

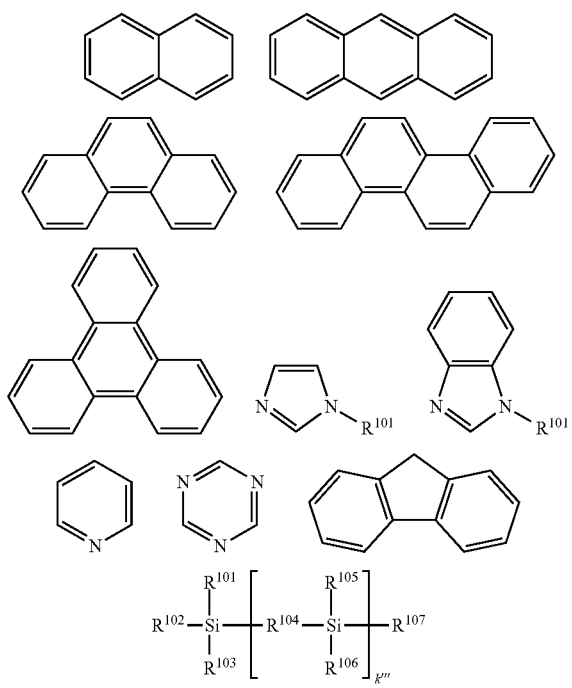

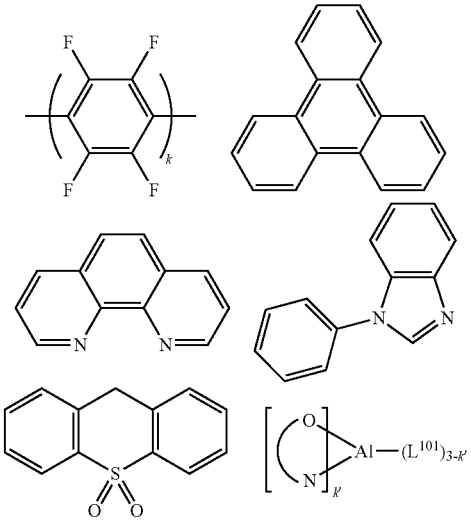

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

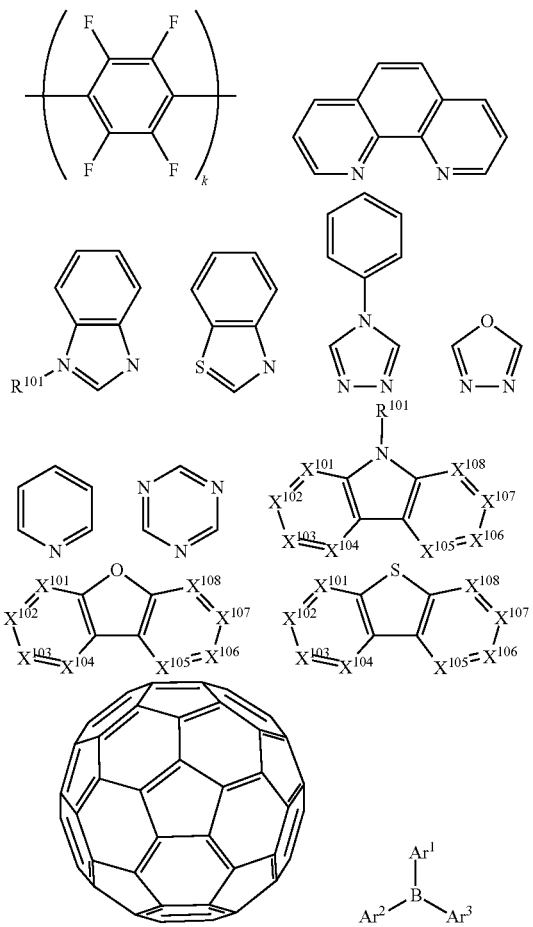

wherein $R^{101}$ is selected from the group consisting of hydrogen, deuterium, halide, alkyl, cycloalkyl, heteroalkyl, aryl-alkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but are not limited to the following general formula:

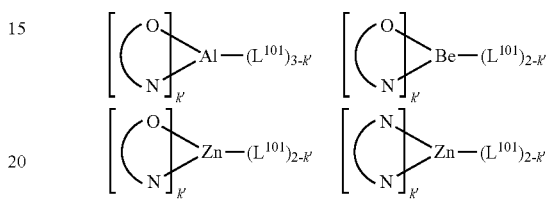

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A
| MATERIAL | EXAMPLES OF MATERIAL | PUBLICATIONS |
|---|---|---|
| Hole injection materials | | |
| Phthalocyanine and porphyrin compounds | 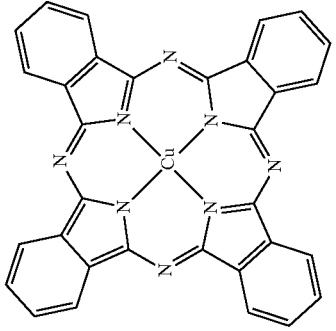 | Appl. Phys. Lett. 69, 2160 (1996) |
| Starburst triarylamines | 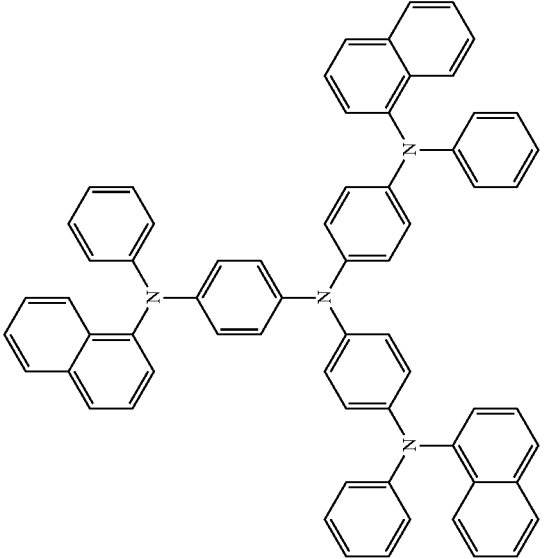 | J. Lumin. 72-74, 985 (1997) |
| $CF_x$ Fluorohydrocarbon polymer | $\mathrm{-\!\!\!+\!\!CH_xF_y\!\!+\!\!\!-}_n$ | Appl. Phys. Lett. 78, 673 (2001) |

TABLE A-continued

| MATERIAL | EXAMPLES OF MATERIAL | PUBLICATIONS |
|---|---|---|
| Conducting polymers (e.g., PEDOT:PSS, polyaniline, polythiophene) | | Synth. Met. 87, 171 (1997) WO2007002683 |
| Phosphonic acid and silane SAMs | | US20030162053 |
| Triarylamine or polythiophene polymers with conductivity dopants | | EP1725079A1 |

TABLE A-continued

| MATERIAL | EXAMPLES OF MATERIAL | PUBLICATIONS |
|---|---|---|
| Organic compounds with conductive inorganic compounds, such as molybdenum and tungsten oxides | [chemical structures: tetrakis(pentafluorophenyl)borate; N,N'-di(naphthalen-1-yl)-N,N'-diphenyl-benzidine + MoO$_x$] | US2005012375 SID Symposium Digest, 37, 923 (2006) WO2009018009 |
| n-type semiconducting organic complexes | [hexacyano-hexaazatriphenylene structure] | US20020158242 |

TABLE A-continued
| MATERIAL | EXAMPLES OF MATERIAL | PUBLICATIONS |
|---|---|---|
| Metal organometallic complexes | 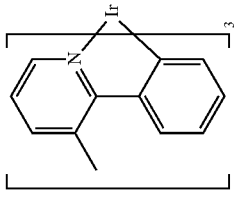 | US2006240279 |
| Cross-linkable compounds | 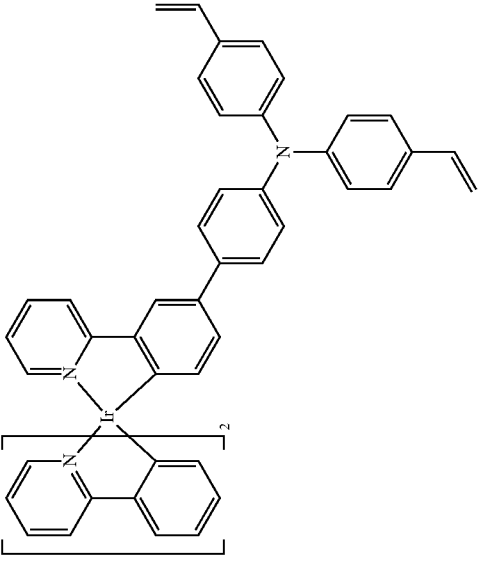 | US2008220265 |

TABLE A-continued
| MATERIAL | EXAMPLES OF MATERIAL | PUBLICATIONS |
|---|---|---|
| Polythiophene based polymers and copolymers | 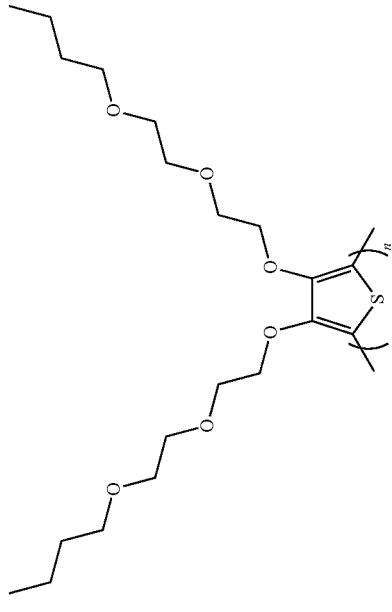 | WO2011075644<br>EP2350216 |
| Hole transporting materials | | |
| Triarylamines (e.g., TPD, α-NPD) | 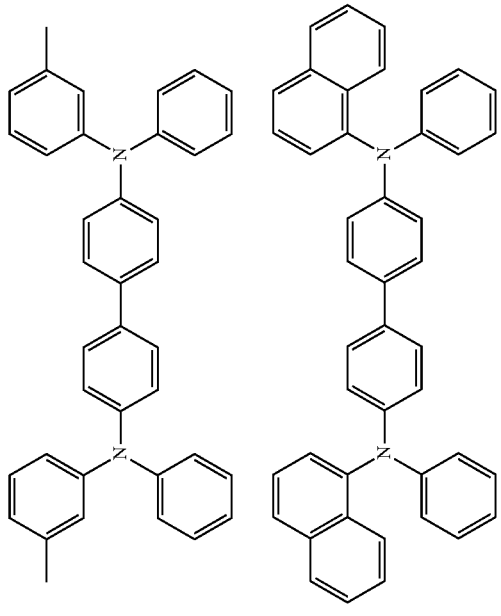 | Appl. Phys. Lett. 51, 913 (1987)<br><br>U.S. Pat. No. 5,061,569 |

TABLE A-continued
| MATERIAL | EXAMPLES OF MATERIAL | PUBLICATIONS |
|---|---|---|
| | 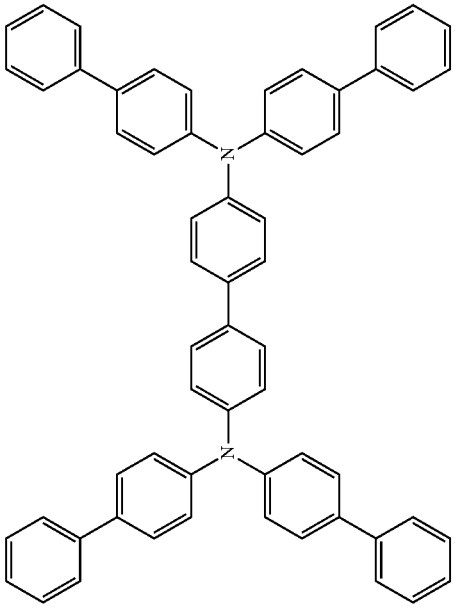 | EP650955 |
| | 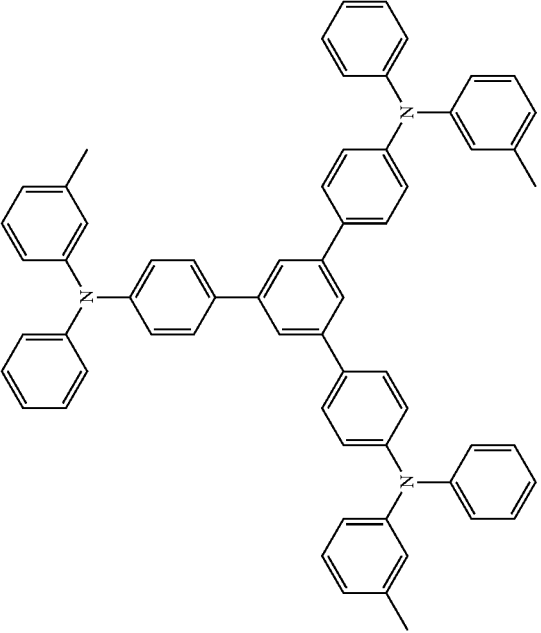 | J. Mater. Chem. 3, 319 (1993) |

TABLE A-continued
| MATERIAL | EXAMPLES OF MATERIAL | PUBLICATIONS |
|---|---|---|
| | 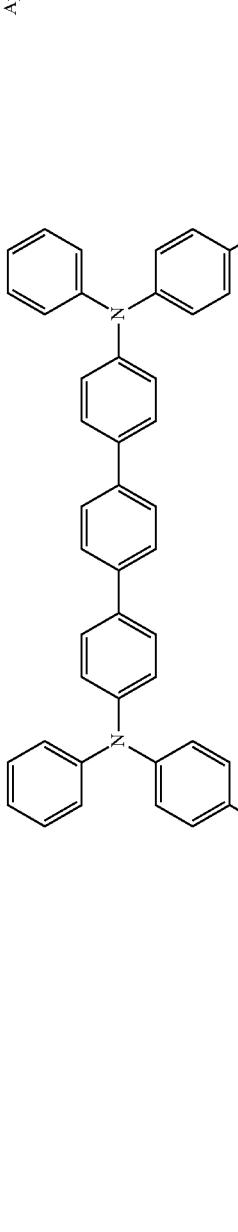 | Appl. Phys. Lett. 90, 183503 (2007) |

TABLE A-continued
| MATERIAL | EXAMPLES OF MATERIAL | PUBLICATIONS |
|---|---|---|
| | 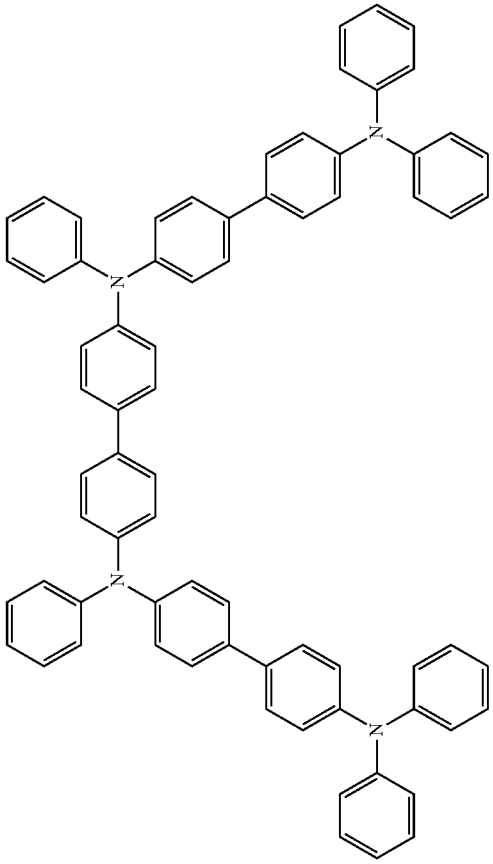 | Appl. Phys. Lett. 90, 183503 (2007) |
| Triarylamine on spirofluorene core | 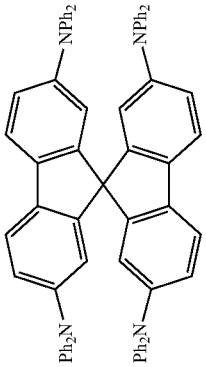 | Synth. Met. 91, 209 (1997) |

TABLE A-continued
| MATERIAL | EXAMPLES OF MATERIAL | PUBLICATIONS |
|---|---|---|
| Arylamine carbazole compounds | 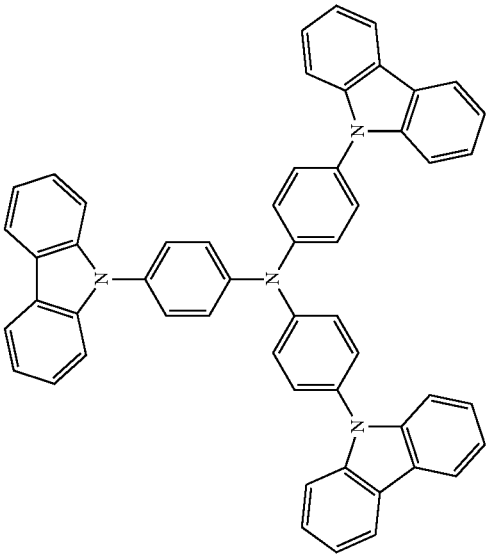 | Adv. Mater. 6, 677 (1994), US20080124572 |
| Triarylamine with (di)benzothiophene/(di)benzofuran | 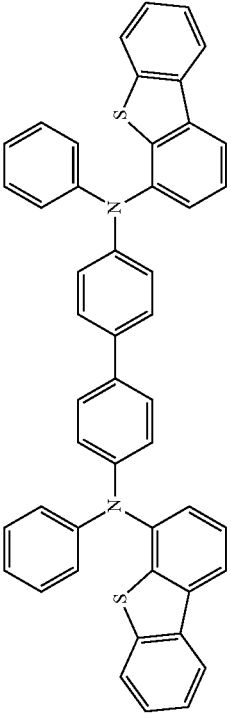 | US20070278938, US20080106190 US20110163302 |

TABLE A-continued
| MATERIAL | EXAMPLES OF MATERIAL | PUBLICATIONS |
|---|---|---|
| Indolocarbazoles | 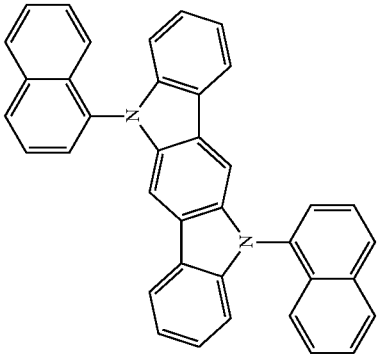 | Synth. Met. 111, 421 (2000) |
| Isoindole compounds | 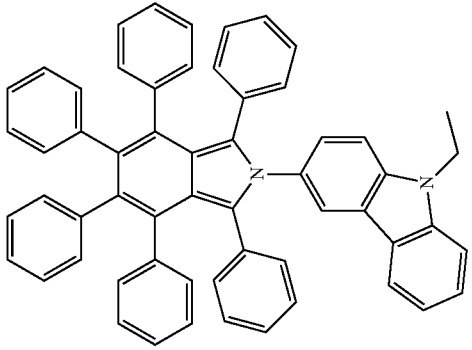 | Chem. Mater. 15, 3148 (2003) |

TABLE A-continued
| MATERIAL | EXAMPLES OF MATERIAL | PUBLICATIONS |
|---|---|---|
| Metal carbene complexes | 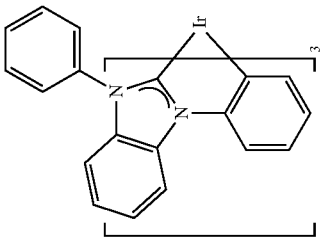 | US20080018221 |
| Phosphorescent OLED host materials Red hosts | | |
| Arylcarbazoles | 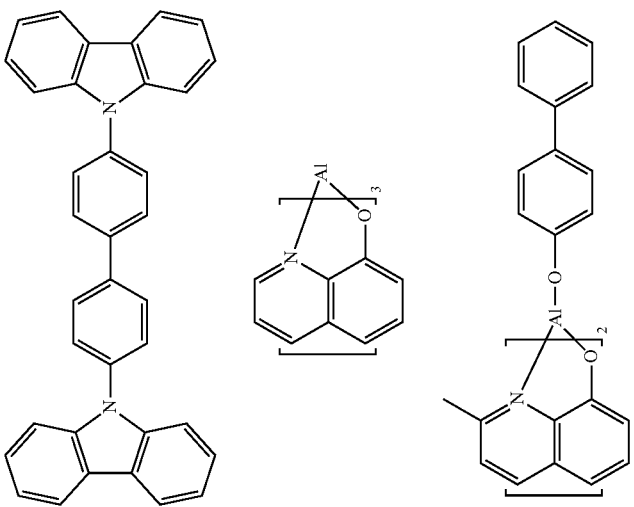 | Appl. Phys. Lett. 78, 1622 (2001) |
| Metal 8-hydroxyquinolates (e.g., Alq$_3$, BAlq) | | Nature 395, 151 (1998) |
| | | US20060202194 |

TABLE A-continued

| MATERIAL | EXAMPLES OF MATERIAL | PUBLICATIONS |
|---|---|---|
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE A-continued
| MATERIAL | EXAMPLES OF MATERIAL | PUBLICATIONS |
|---|---|---|
| Aromatic fused rings | 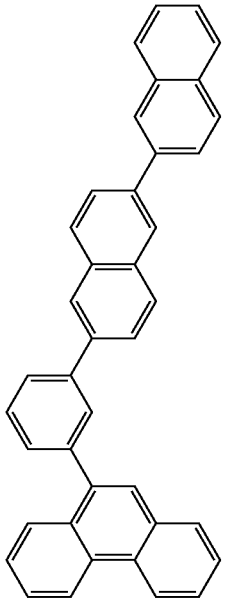 | WO2009066779, WO2009066778, WO2009063833, US20090045731, US20090045730, WO2009008311, US20090008605, US20090009065 |
| Zinc complexes | 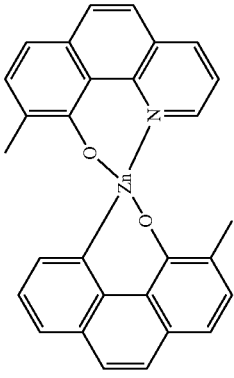 | WO2010056066 |
| Chrysene based compounds | 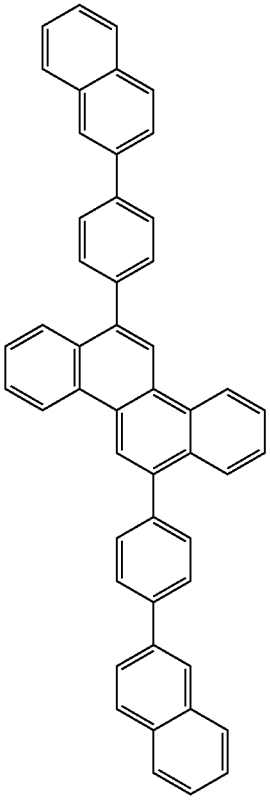 | WO2011086863 |
| Green hosts | | |
| Arylcarbazoles | 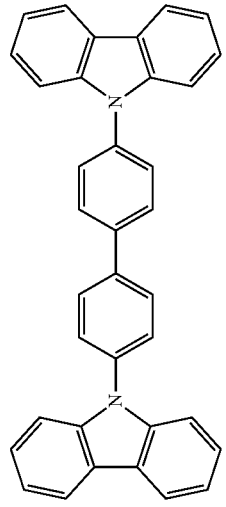 | Appl. Phys. Lett. 78, 1622 (2001) |

TABLE A-continued
| MATERIAL | EXAMPLES OF MATERIAL | PUBLICATIONS |
|---|---|---|
| | 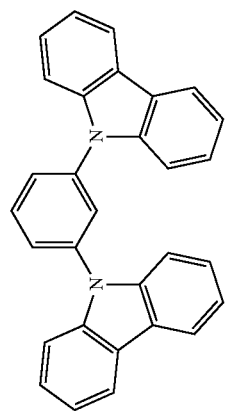 | US2003017553 |
| | 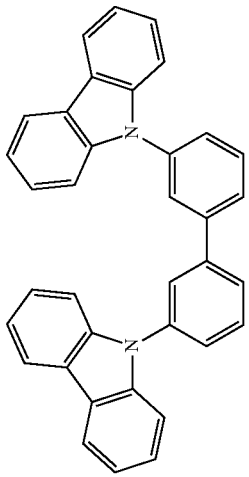 | WO2001039234 |
| Aryltriphenylene compounds | 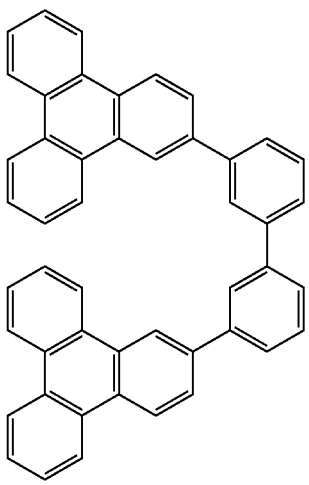 | US2006028096 |

TABLE A-continued
| MATERIAL | EXAMPLES OF MATERIAL | PUBLICATIONS |
|---|---|---|
| | 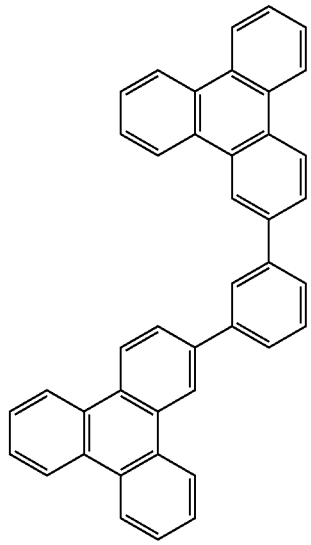 | US20060280965 |
| | 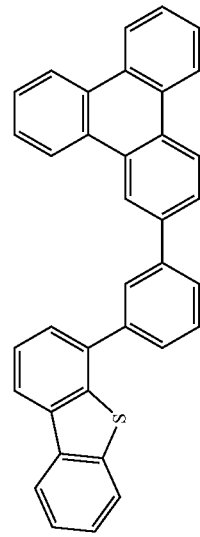 | WO2009021126 |
| Poly-fused heteroaryl compounds | 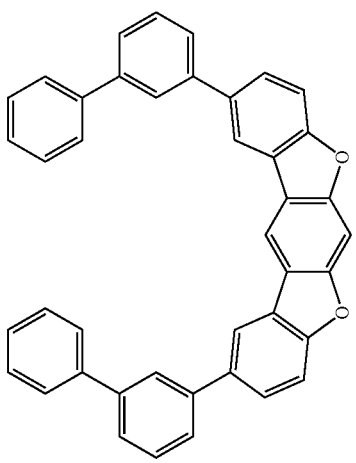 | US20090309488<br>US20090302743<br>US20100012931 |

TABLE A-continued
| MATERIAL | EXAMPLES OF MATERIAL | PUBLICATIONS |
|---|---|---|
| Donor acceptor type molecules | 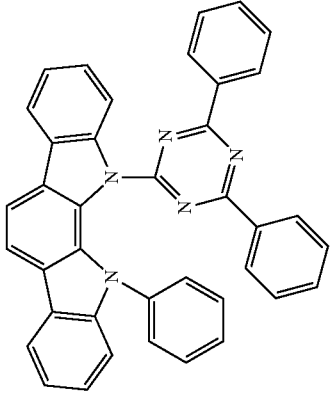 | WO2008056746 |
| | 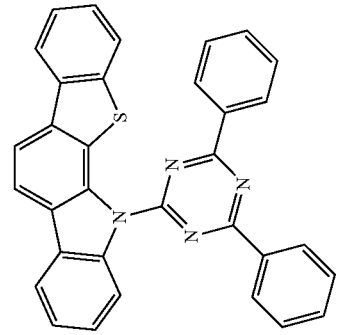 | WO2010107244 |

TABLE A-continued
| MATERIAL | EXAMPLES OF MATERIAL | PUBLICATIONS |
|---|---|---|
| Aza-carbazole/DBT/DBF | 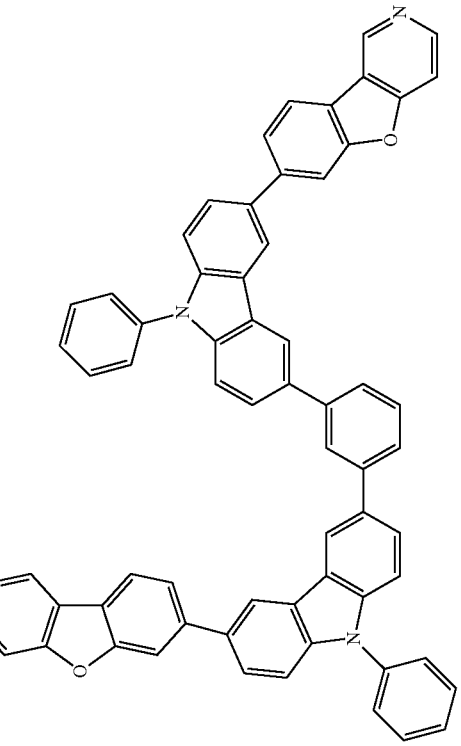 | JP2008074939 US20100187984 |
| Polymers (e.g., PVK) | 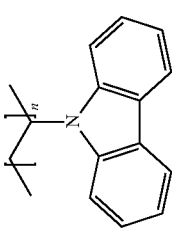 | Appl. Phys. Lett. 77, 2280 (2000) |

TABLE A-continued

| MATERIAL | EXAMPLES OF MATERIAL | PUBLICATIONS |
|---|---|---|
| Spirofluorene compounds | | WO2004093207 |
| Metal phenoxybenzooxazole compounds | | WO2005089025 |
| | | WO2006132173 |

TABLE A-continued
| MATERIAL | EXAMPLES OF MATERIAL | PUBLICATIONS |
|---|---|---|
| | 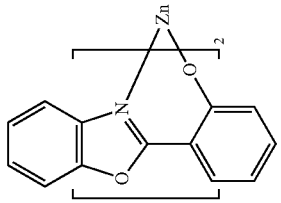 | JP2005111610 |
| Spirofluorene-carbazole compounds | 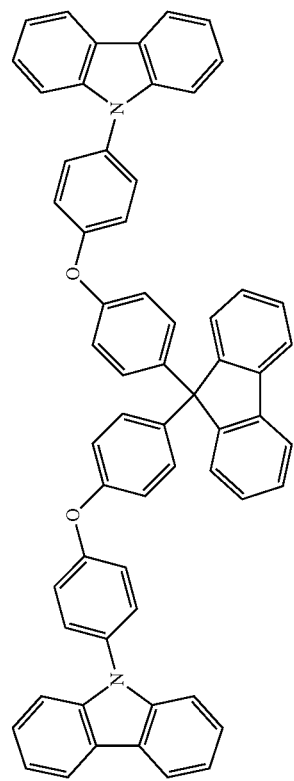 | JP2007254297 |
| | 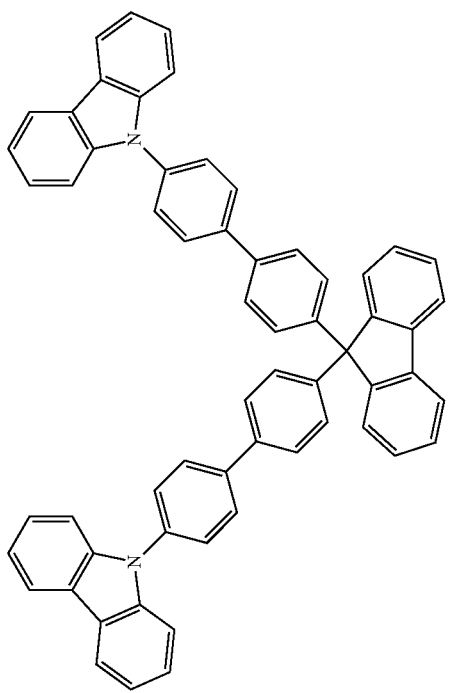 | JP2007254297 |

TABLE A-continued
| MATERIAL | EXAMPLES OF MATERIAL | PUBLICATIONS |
|---|---|---|
| Indolocarbazoles | 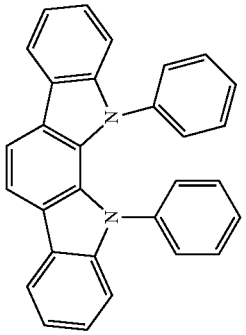 | WO2007063796 |
| | 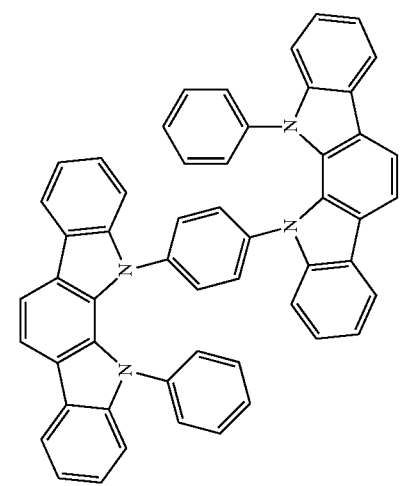 | WO2007063754 |
| 5-member ring electron deficient heterocycles (e.g., triazole, oxadiazole) | 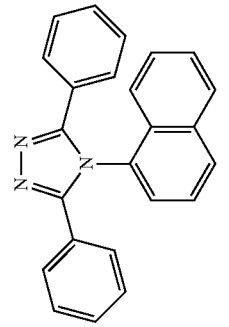 | J. Appl. Phys. 90, 5048 (2001) |

TABLE A-continued

| MATERIAL | EXAMPLES OF MATERIAL | PUBLICATIONS |
|---|---|---|
| | | WO2004107822 |
| | | US20050112407 |
| Tetraphenylene complexes | | |
| Metal phenoxypyridine compounds | | WO2005030900 |

TABLE A-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |
| Blue hosts | | |
| Arylcarbazoles | | Appl. Phys. Lett. 82, 2422 (2003) |
| | | US20070190359 |

TABLE A-continued
| MATERIAL | EXAMPLES OF MATERIAL | PUBLICATIONS |
|---|---|---|
| Dibenzothiophene/Dibenzofuran-carbazole compounds | 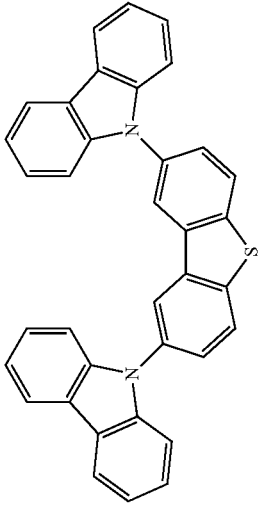 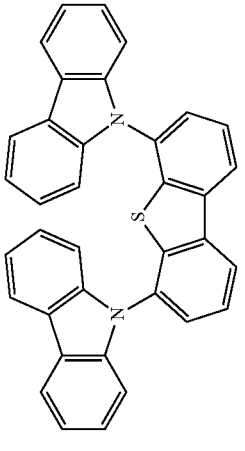 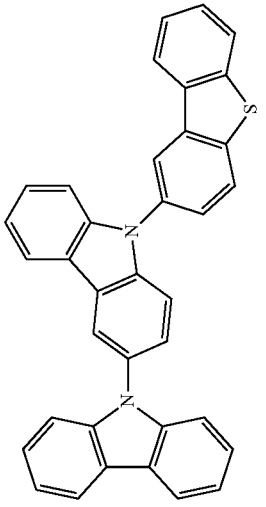 | WO2006114966, US20090167162<br>US20090167162<br>WO2009086028 |

TABLE A-continued
| MATERIAL | EXAMPLES OF MATERIAL | PUBLICATIONS |
|---|---|---|
| | 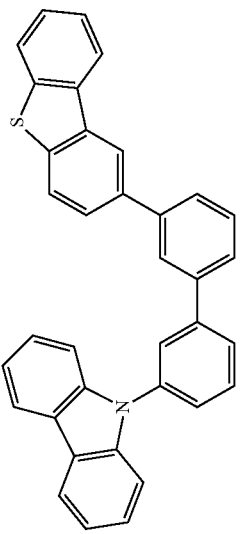 | US20090030202, US20090017330 |
| | 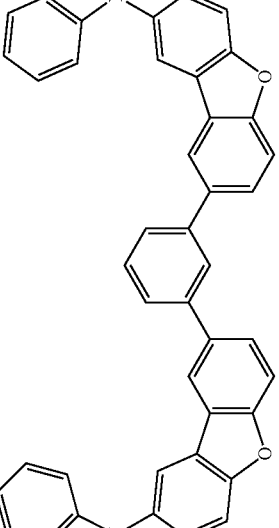 | US20100084966 |
| Silicon aryl compounds | 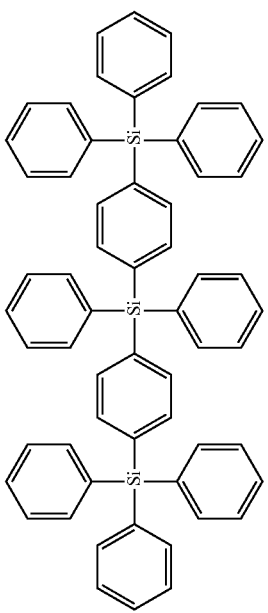 | US20050238919 |

TABLE A-continued
| MATERIAL | EXAMPLES OF MATERIAL | PUBLICATIONS |
|---|---|---|
| Silicon/Germanium aryl compounds | 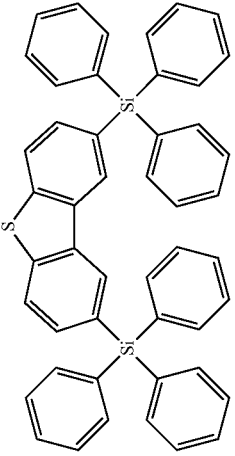 | WO2009003898 |
| | 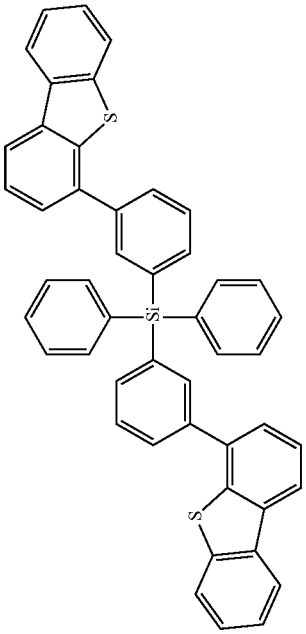 | EP2034538A |
| Aryl benzoyl ester | 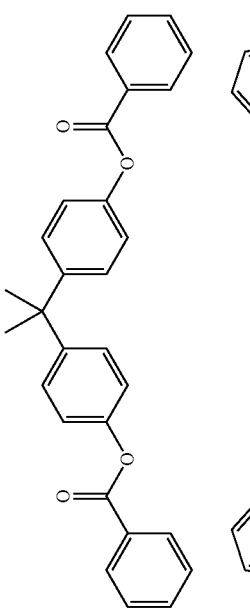 | WO2006100298 |
| Carbazole linked by non-conjugated groups | 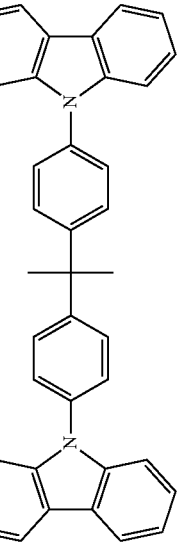 | US20040115476 |

TABLE A-continued
| MATERIAL | EXAMPLES OF MATERIAL | PUBLICATIONS |
|---|---|---|
| Aza-carbazoles | 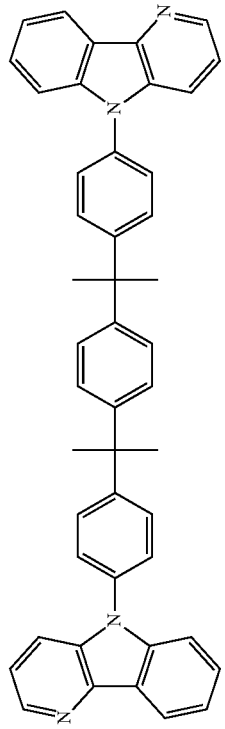 | US20060121308 |
| High triplet metal organometallic complex | 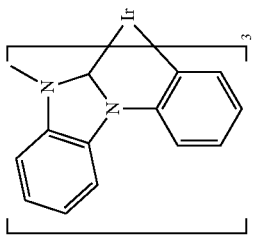 | U.S. Pat. No. 7,154,114 |
| Phosphorescent dopants Red dopants | | |
| Heavy metal porphyrins (e.g., PtOEP) | 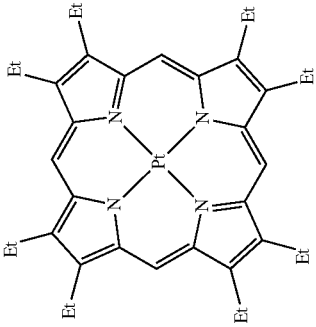 | Nature 395, 151 (1998) |

TABLE A-continued
| MATERIAL | EXAMPLES OF MATERIAL | PUBLICATIONS |
|---|---|---|
| Iridium(III) organometallic complexes | 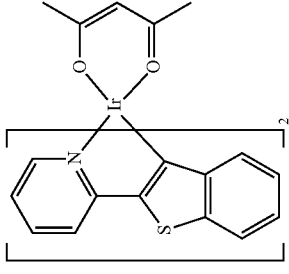 | Appl. Phys. Lett. 78, 1622 (2001) |
| | 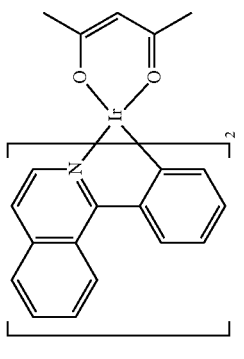 | US2003072964 |
| | 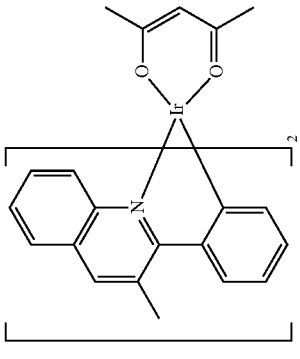 | US2003072964 |

TABLE A-continued
| MATERIAL | EXAMPLES OF MATERIAL | PUBLICATIONS |
|---|---|---|
| | 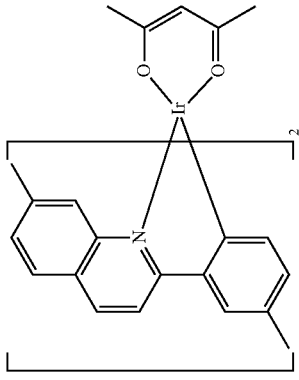 | US20060202194 |
| | 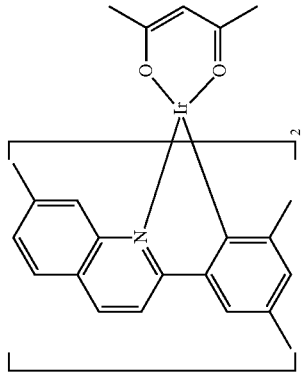 | US20060202194 |
| | 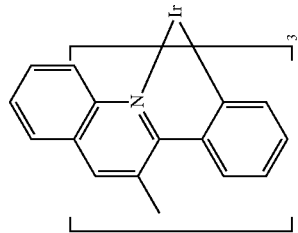 | US20070087321 |

TABLE A-continued
| MATERIAL | EXAMPLES OF MATERIAL | PUBLICATIONS |
|---|---|---|
| | 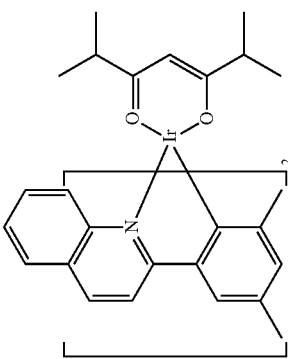 | US20080261076 US20100090591 |
| | 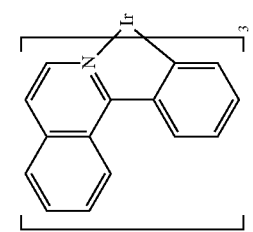 | US20070087321 |
| | 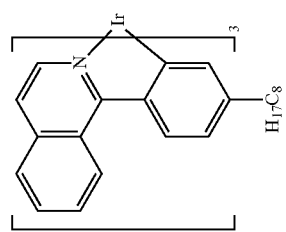 | Adv. Mater. 19, 739 (2007) |

TABLE A-continued

| MATERIAL | EXAMPLES OF MATERIAL | PUBLICATIONS |
|---|---|---|
| | | WO2009100991 |
| | | WO2008101842 |
| | | U.S. Pat. No. 7,232,618 |

TABLE A-continued
| MATERIAL | EXAMPLES OF MATERIAL | PUBLICATIONS |
|---|---|---|
| Platinum(II) organometallic complexes | 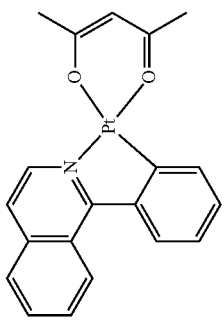 | WO2003040257 |
| | 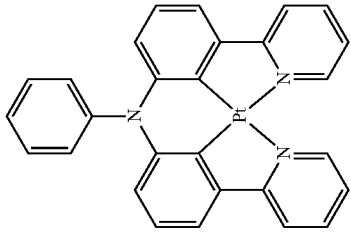 | US20070103060 |
| Osminum(III) complexes | 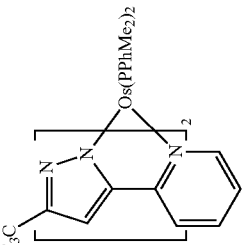 | Chem. Mater. 17, 3532 (2005) |

TABLE A-continued
| MATERIAL | EXAMPLES OF MATERIAL | PUBLICATIONS |
| --- | --- | --- |
| Ruthenium(II) complexes | 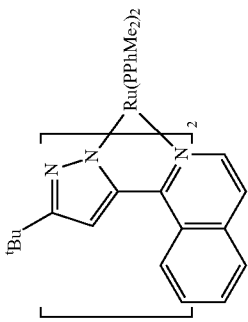 | Adv. Mater. 17, 1059 (2005) |
| Rhenium (I), (II), and (III) complexes | 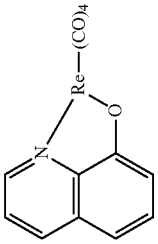 | US20050244673 |
| | Green dopants | |
| Iridium(III) organometallic complexes | 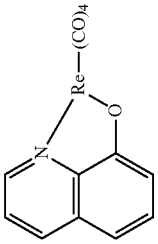 and its derivatives | Inorg. Chem. 40, 1704 (2001) |

TABLE A-continued
| MATERIAL | EXAMPLES OF MATERIAL | PUBLICATIONS |
|---|---|---|
| | 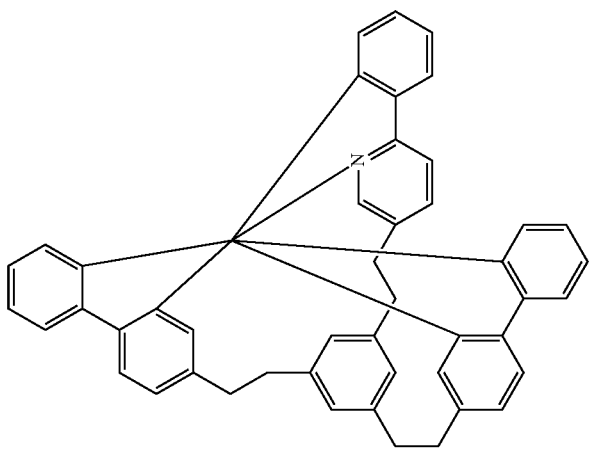 | US20020034656<br><br>U.S. Pat. No. 7,332,232 |

TABLE A-continued
| MATERIAL | EXAMPLES OF MATERIAL | PUBLICATIONS |
|---|---|---|
| | 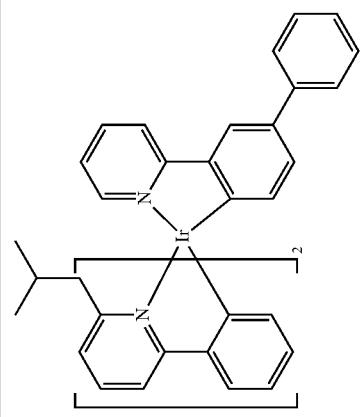 | US20090108737 |
| | 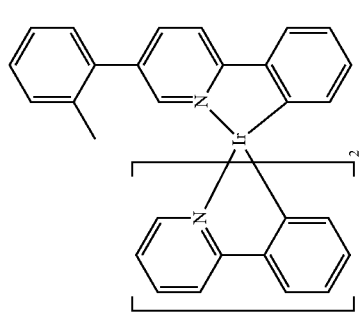 | WO2010028151 |

TABLE A-continued
| MATERIAL | EXAMPLES OF MATERIAL | PUBLICATIONS |
|---|---|---|
| | 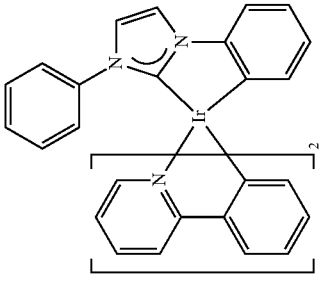 | EP1841834B<br><br>US20060127696<br><br>US20090039776 |

TABLE A-continued
| MATERIAL | EXAMPLES OF MATERIAL | PUBLICATIONS |
|---|---|---|
| | 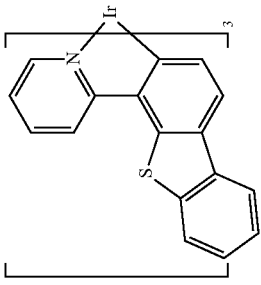 | U.S. Pat. No. 6,921,915 |
| | 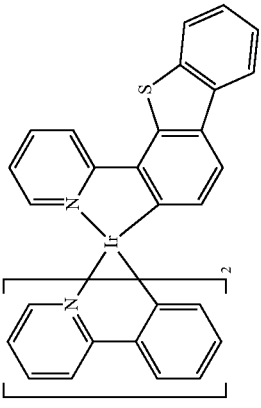 | US20100244004 |
| | 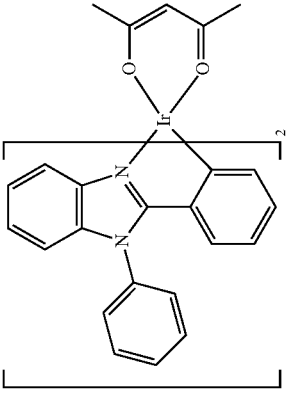 | U.S. Pat. No. 6,687,266 |

TABLE A-continued
| MATERIAL | EXAMPLES OF MATERIAL | PUBLICATIONS |
|---|---|---|
| | 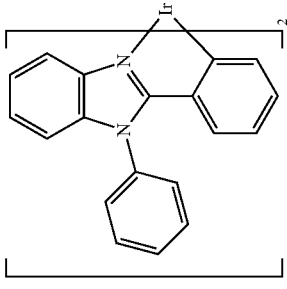 | Chem. Mater. 16, 2480 (2004) |
| | 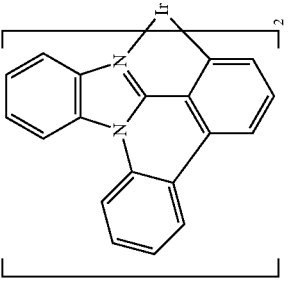 | US20070190359 |
| | 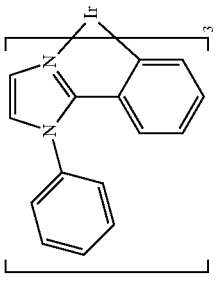 | US20060008670 JP2007123392 |

TABLE A-continued
| MATERIAL | EXAMPLES OF MATERIAL | PUBLICATIONS |
|---|---|---|
| | 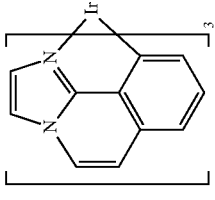 | WO2010086089, WO2011044988 |
| | 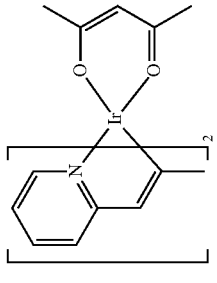 | Adv. Mater. 16, 2003 (2004) |
| | 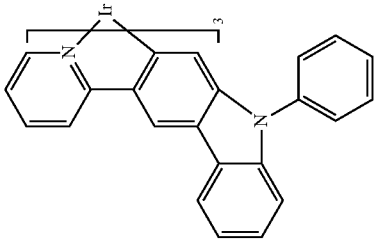 | Angew. Chem. Int. Ed. 2006, 45, 7800 |

TABLE A-continued
| MATERIAL | EXAMPLES OF MATERIAL | PUBLICATIONS |
|---|---|---|
| | 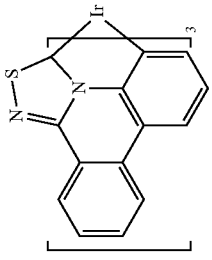 | WO2009050290 |
| | 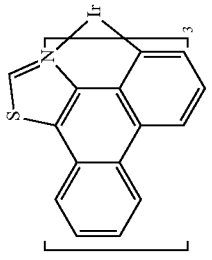 | US20090165846 |
| | 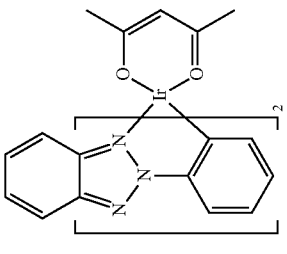 | US20080015355 |
| | 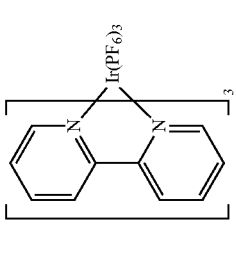 | US20100015432 |

TABLE A-continued
| MATERIAL | EXAMPLES OF MATERIAL | PUBLICATIONS |
| --- | --- | --- |
| Monomer for polymeric metal organometallic compounds | 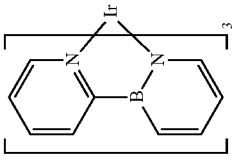 | US20100295032 U.S. Pat. No. 7,250,226, U. S. Pat. No. 7,396,598 |
| Pt(II) organometallic complexes, including polydentated ligands | 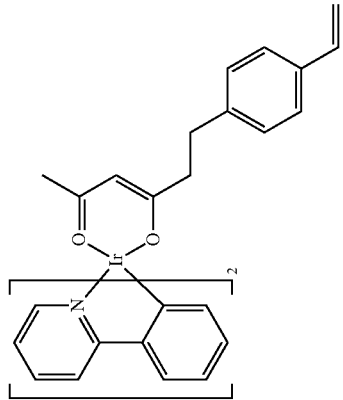 | Appl. Phys. Lett. 86, 153505 (200) |

TABLE A-continued

| MATERIAL | EXAMPLES OF MATERIAL | PUBLICATIONS |
|---|---|---|
| | (Pt complex with phenoxy and bis-pyridylphenyl ligand) | Appl. Phys. Lett. 86, 153505 (2005) |
| | (Pt complex with pentafluorophenyl and bis-pyridyl-diphenyl-naphthalene ligand) | Chem. Lett. 34, 592 (2005) |
| | (Pt complex with acetylacetonate and phenylpyridine ligand) | WO2002015645 |

TABLE A-continued
| MATERIAL | EXAMPLES OF MATERIAL | PUBLICATIONS |
|---|---|---|
| | 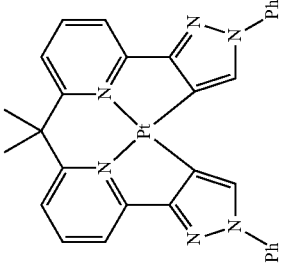 | US20060263635 |
| | 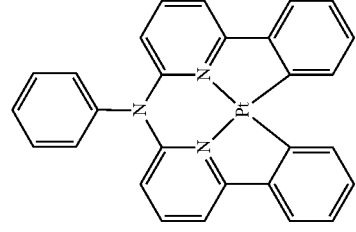 | US20060182992<br>US20070103060 |

TABLE A-continued
| MATERIAL | EXAMPLES OF MATERIAL | PUBLICATIONS |
|---|---|---|
| Cu complexes | 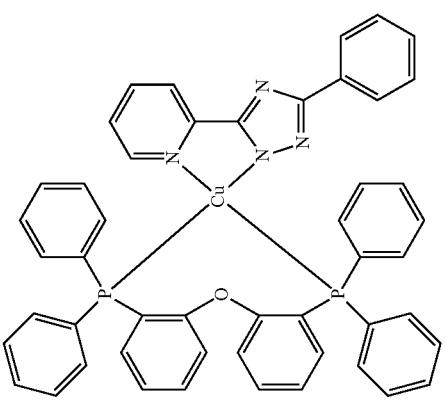 | WO2009000673 |
| | 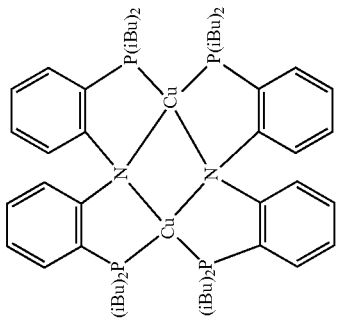 | US20070111026 |

TABLE A-continued
| MATERIAL | EXAMPLES OF MATERIAL | PUBLICATIONS |
|---|---|---|
| Gold complexes | 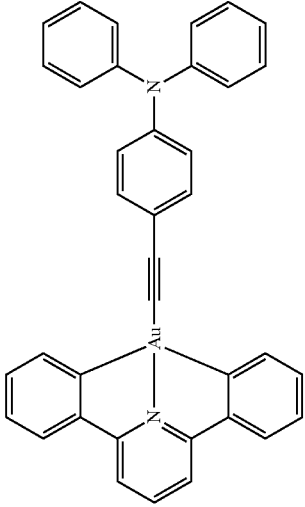 | Chem. Commun. 2906 (2005) |
| Rhenium(III) complexes | 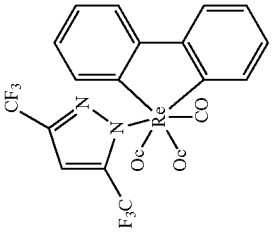 | Inorg. Chem. 42, 1248 (2003) |
| Osmium(II) complexes | 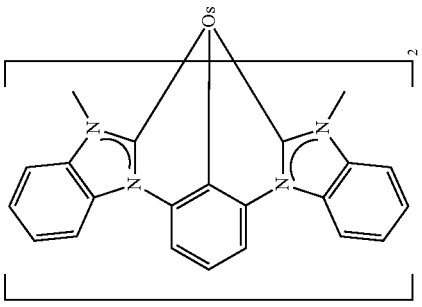 | U.S. Pat. No. 7,279,704 |

TABLE A-continued
| MATERIAL | EXAMPLES OF MATERIAL | PUBLICATIONS |
|---|---|---|
| Deuterated organometallic complexes | 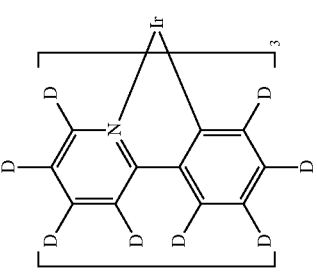 | US20030138657 |
| Organometallic complexes with two or more metal centers | 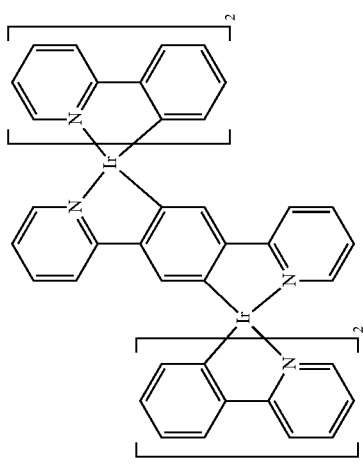 | US20030152802 |

TABLE A-continued
| MATERIAL | EXAMPLES OF MATERIAL | PUBLICATIONS |
|---|---|---|
| | 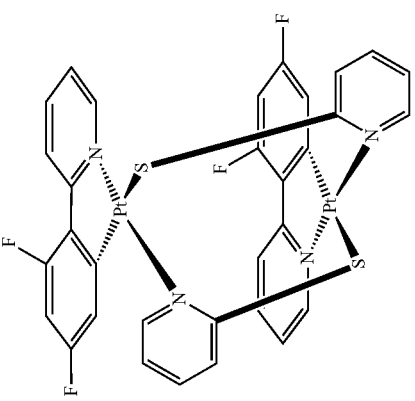 | U.S. Pat. No. 7,090,928 |
| Iridium(III) organometallic complexes Blue dopants | 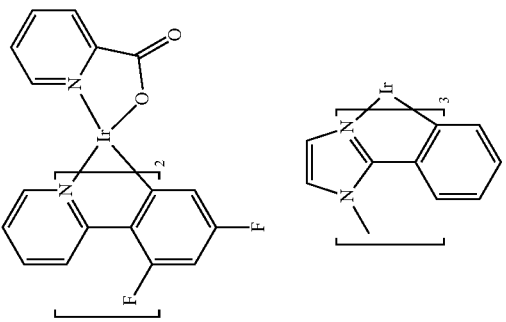 | WO2002002714<br><br>WO2006009024 |

TABLE A-continued
| MATERIAL | EXAMPLES OF MATERIAL | PUBLICATIONS |
|---|---|---|
| | 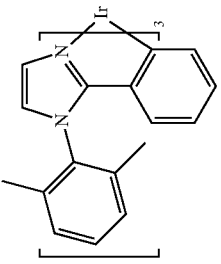 | US20060251923 US20110057559 US20110204333 |
| | 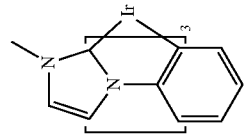 | U.S. Pat. No. 7,393,599, WO2006056418, US20050260441, WO2005019373 |
| | 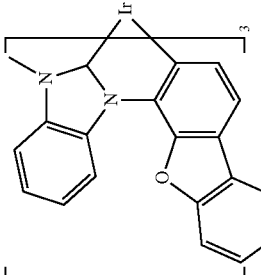 | U.S. Pat. No. 7,534,505 |

TABLE A-continued
| MATERIAL | EXAMPLES OF MATERIAL | PUBLICATIONS |
|---|---|---|
| | 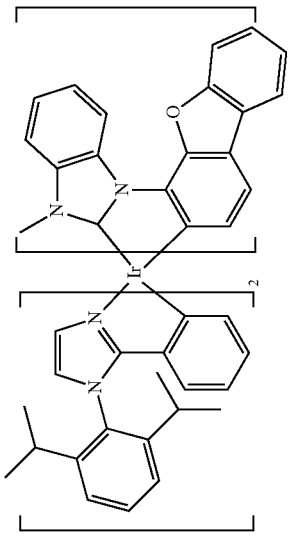 | WO2011051404 |
| | 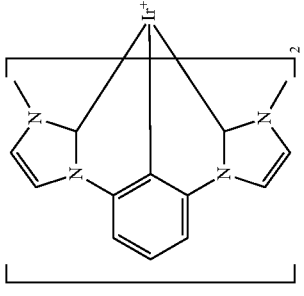 | U.S. Pat. No. 7,445,855 |
| | 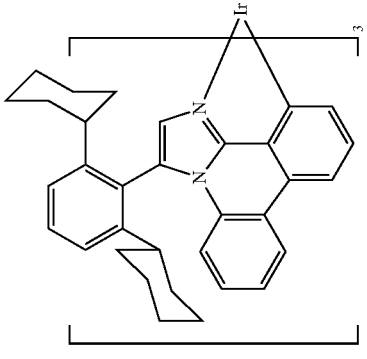 | US2007/0190359, US2008/0297033 US2010/0148663 |

TABLE A-continued
| MATERIAL | EXAMPLES OF MATERIAL | PUBLICATIONS |
|---|---|---|
| | 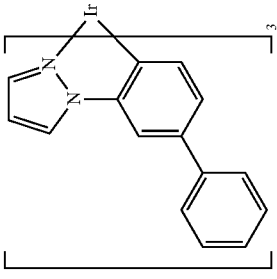 | U.S. Pat. No. 7,338,722 |
| | | US20020134984 |
| | 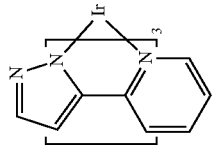 | Angew. Chem. Int. Ed. 47, 4542 (2008) |

TABLE A-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO2005123873 |

TABLE A-continued

| MATERIAL | EXAMPLES OF MATERIAL | PUBLICATIONS |
|---|---|---|
| | | WO2005123873 |
| | | WO2007004380 |
| | | WO2006082742 |

TABLE A-continued
| MATERIAL | EXAMPLES OF MATERIAL | PUBLICATIONS |
|---|---|---|
| Osmium(II) complexes | 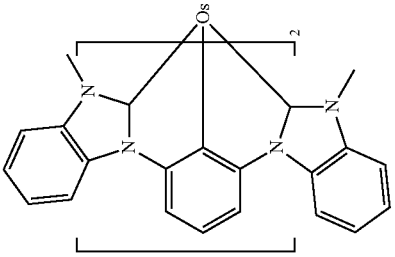 | U.S. Pat. No. 7,279,704 |
| | 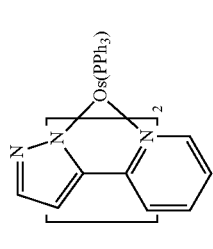 | Organometallics 23, 3745 (2004) |
| Gold complexes | 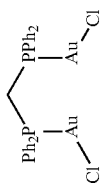 | Appl. Phys. Lett. 74, 1361 (1999) |
| Platinum(II) complexes | 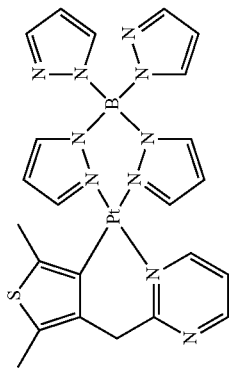 | WO2006098120, WO2006103874 |

TABLE A-continued

| MATERIAL | EXAMPLES OF MATERIAL | PUBLICATIONS |
|---|---|---|
| Pt tetradentate complexes with at least one metal-carbene bond | | U.S. Pat. No. 7,655,323 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |

TABLE A-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 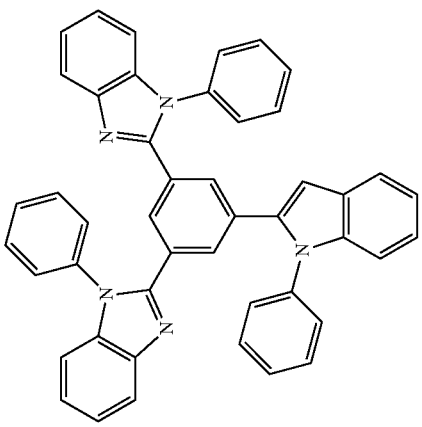 | Appl. Phys. Lett. 81, 162 (2002) |
| Triphenylene compounds | 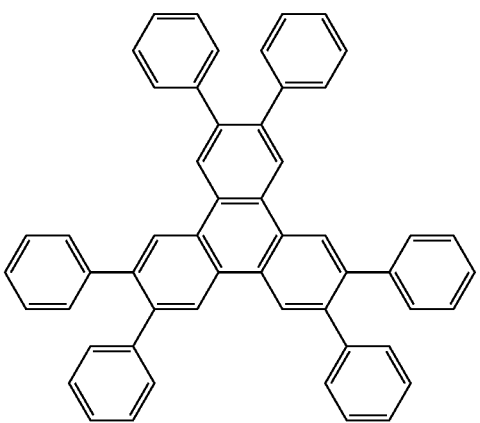 | US20050025993 |

TABLE A-continued
| MATERIAL | EXAMPLES OF MATERIAL | PUBLICATIONS |
|---|---|---|
| Fluorinated aromatic compounds | 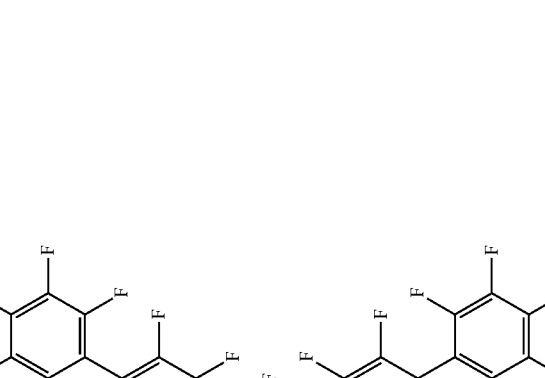 | Appl. Phys. Lett. 79, 156 (2001) |
| Phenothiazine-S-oxide |  | WO2008013208S |

TABLE A-continued
| MATERIAL | EXAMPLES OF MATERIAL | PUBLICATIONS |
|---|---|---|
| Silylated five-membered nitrogen, oxygen, sulfur or phosphorus dibenzoheterocycles | 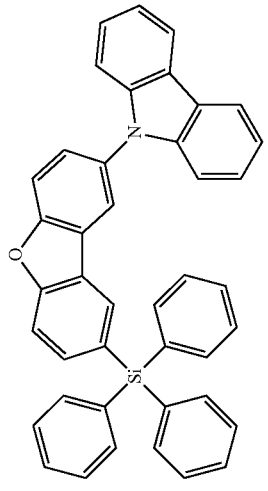 | WO2010079051 |
| Aza-carbazoles | 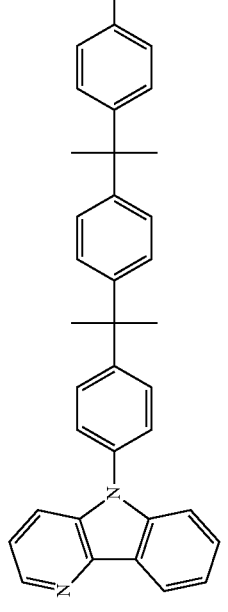 | US20060121308 |
| Electron transporting materials | | |
| Anthracene-benzoimidazole compounds | 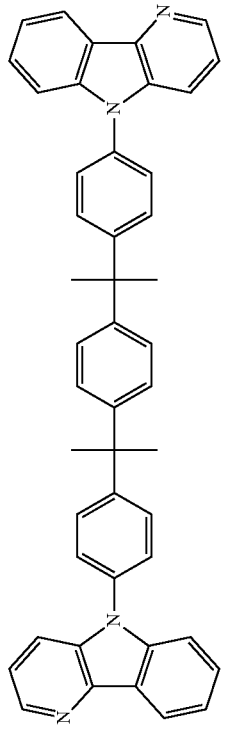 | WO2003060956 |

TABLE A-continued
| MATERIAL | EXAMPLES OF MATERIAL | PUBLICATIONS |
|---|---|---|
| | 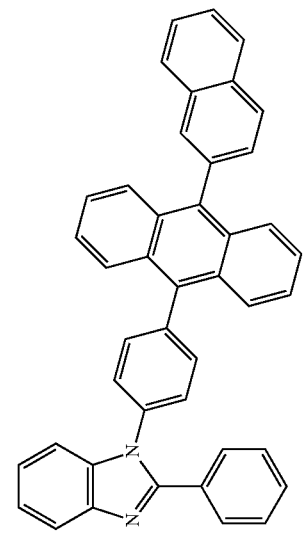 | US20090179554 |
| Aza triphenylene derivatives | 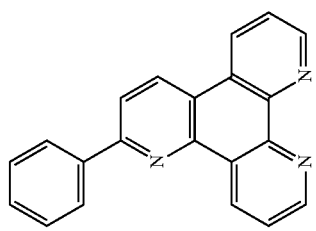 | US20090115316 |
| Anthracene-benzothiazole compounds | 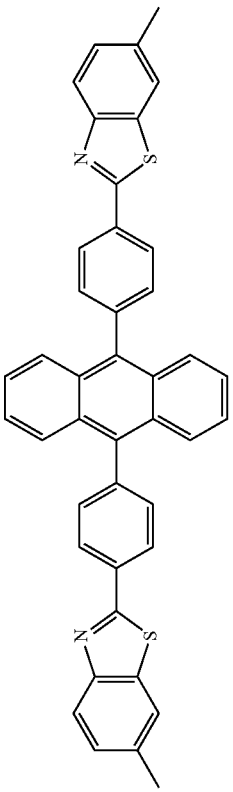 | Appl. Phys. Lett. 89, 063504 (2006) |

TABLE A-continued
| MATERIAL | EXAMPLES OF MATERIAL | PUBLICATIONS |
|---|---|---|
| Metal 8-hydroxyquinolates (e.g., Alq$_3$, Zrq$_4$) | 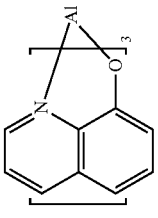 | Appl. Phys. Lett. 51, 913 (1987) U.S. Pat. No. 7,230,107 |
| Metal hydroxybenoquinolates | 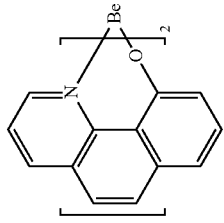 | Chem. Lett. 5, 905 (1993) |
| Bathocuprine compounds such as BCP, BPhen, etc | 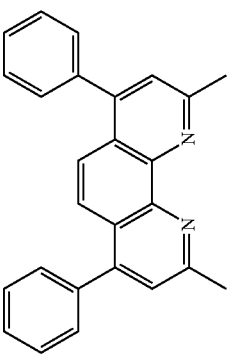 | Appl. Phys. Lett. 91, 263503 (2007) |
| | 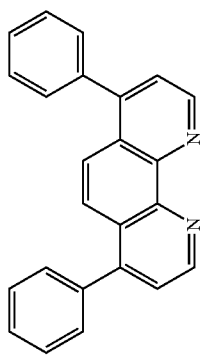 | Appl. Phys. Lett. 79, 449 (2001) |

TABLE A-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 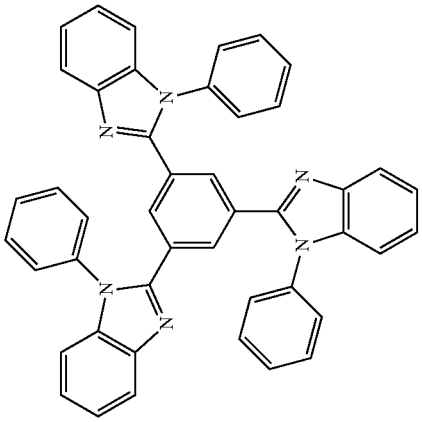 | Appl. Phys. Lett. 74, 865 (1999) |
| | 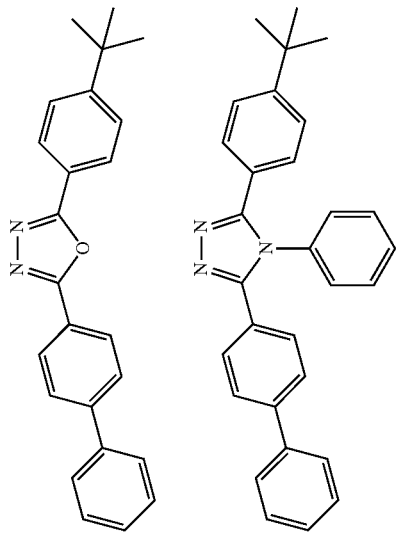 | Appl. Phys. Lett. 55, 1489 (1989)<br><br>Jpn. J. Apply. Phys. 32, L917 (1993) |

TABLE A-continued

| MATERIAL | EXAMPLES OF MATERIAL | PUBLICATIONS |
|---|---|---|
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |

TABLE A-continued
| MATERIAL | EXAMPLES OF MATERIAL | PUBLICATIONS |
|---|---|---|
| Triazine complexes | 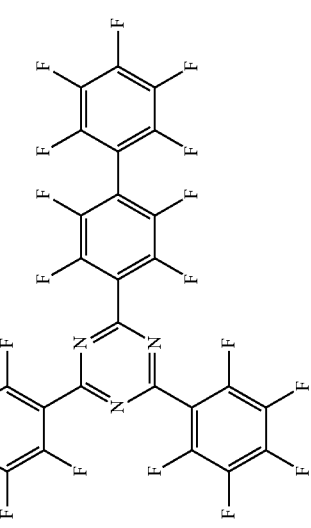 | US2004036077 |
| Zn (N^N) complexes | 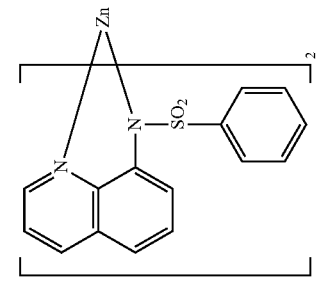 | U.S. Pat. No. 6,528,187 |

EXPERIMENTAL

Synthesis

Compound 5

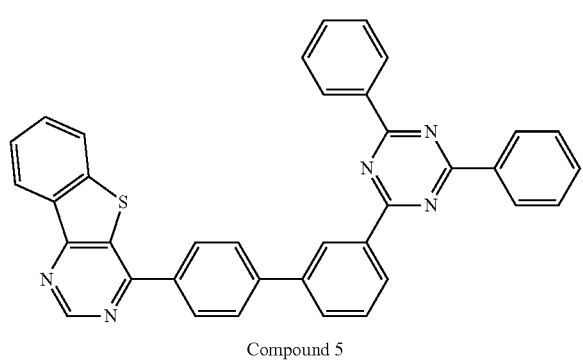
Compound 5

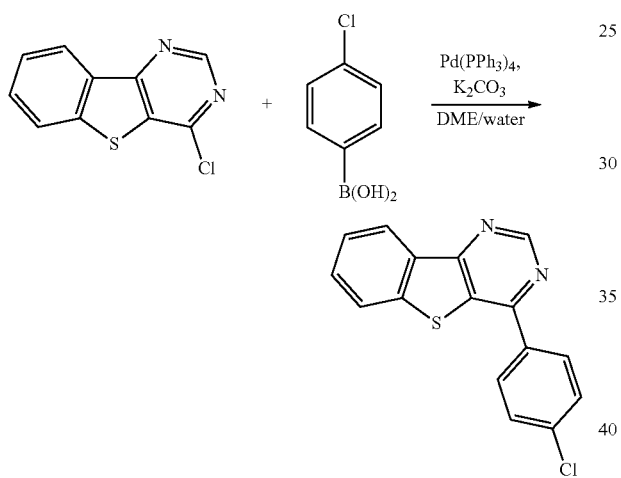

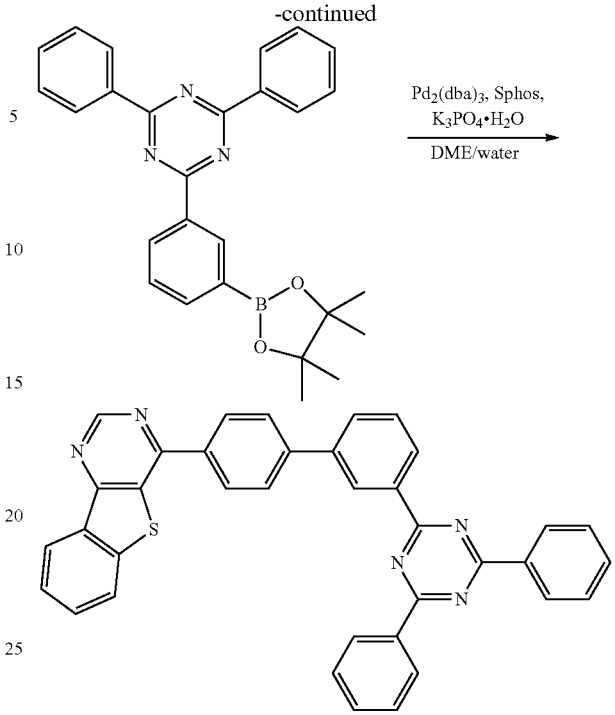

A solution of 4-(4-chlorophenyl)benzo[4,5]thieno[3,2-d]pyrimidine (2.86 g, 9.65 mmol), 2,4-diphenyl-6-(3-(4,4,5,5-tetramethyl-1,3,2-dioxaborolan-2-yl)phenyl)-1,3,5-triazine (4.2 g, 9.65 mmol), $Pd_2(dba)_3$ (0.177 g, 0.193 mmol) and Sphos (0.158 g, 0.386 mmol) $K_3PO_4 \cdot H_2O$ (6.67 g, 28.9 mmol) in DME (200 ml) and water (5 ml) was refluxed under nitrogen overnight. After cooling to room temperature, the solid was collected by filtration, washed successively with water, ethanol, and heptane to yield Compound 5 (4.1 g, 75%) as a white solid.

Compound 158

A solution of 4-chlorobenzo[4,5]thieno[3,2-d]pyrimidine (5 g, 22.66 mmol), (4-chlorophenyl) boronic acid (3.54 g, 22.66 mmol), $Pd(PPh_3)_4$ (0.524 g, 0.453 mmol) and $K_2CO_3$ (6.26 g, 45.3 mmol) in DME (150 ml) and water (20 ml) was refluxed under nitrogen overnight. After cooling to room temperature, a solid precipitate was collected by filtration, washed successively with water, ethanol, and heptane to yield 4-(4-chlorophenyl)benzo[4,5]thieno[3,2-d]pyrimidine (4.0 g, 75%) as a white solid.

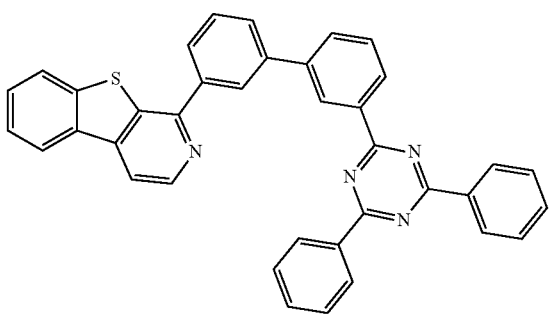
Compound 158

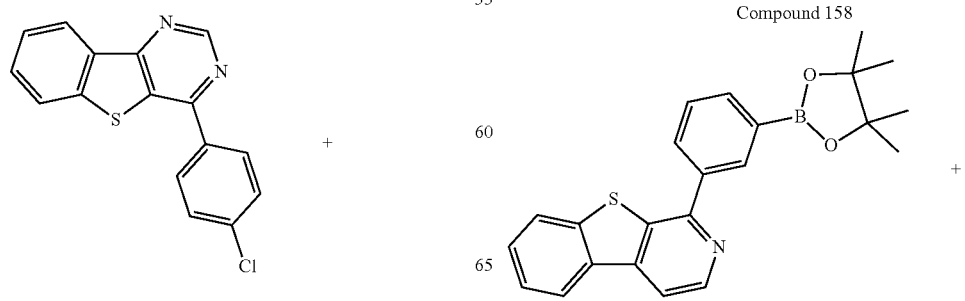

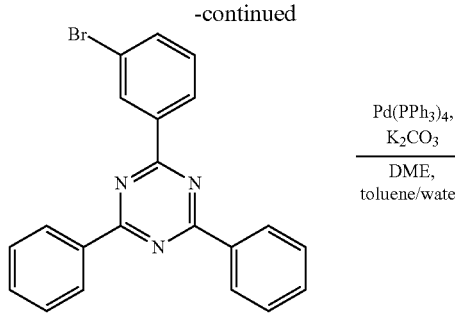

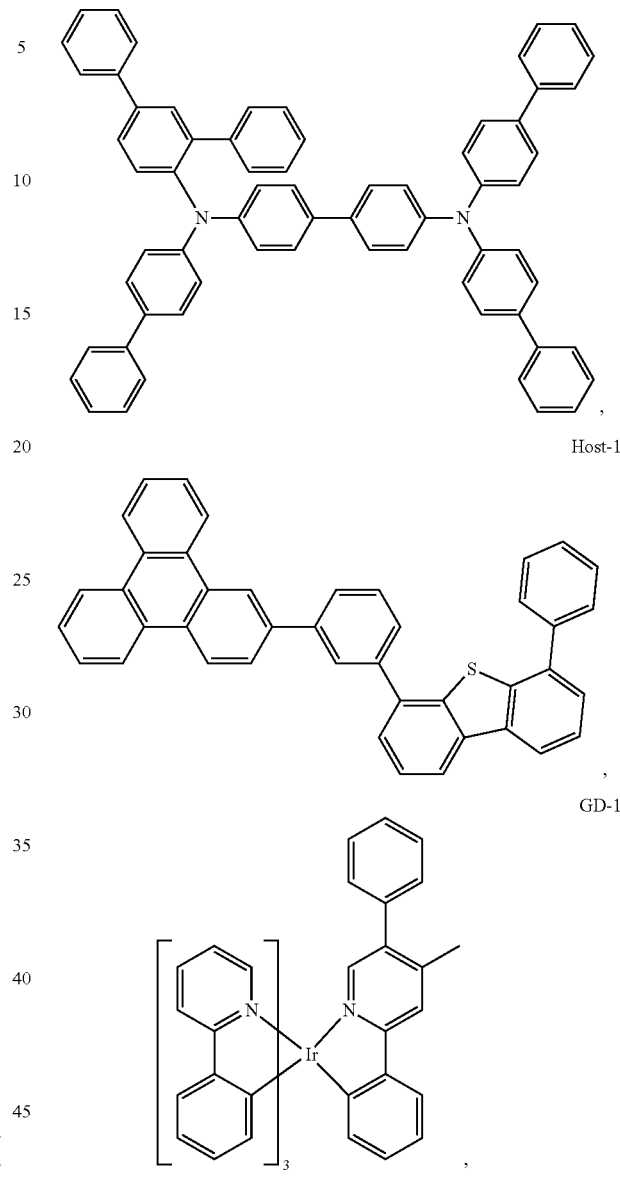

A suspension of 1-(3-(4,4,5,5-tetramethyl-1,3,2-dioxaborolan-2-yl)phenyl)benzo[4,5]thieno[2,3-c]pyridine (3.0 g, 7.75 mmol), 2-(3-bromophenyl)-4,6-diphenyl-1,3,5-triazine (3.61 g, 9.30 mmol), Pd(PPh$_3$)$_4$ (0.179 g, 0.155 mmol) and K$_2$CO$_3$ (3.21 g, 23.24 mmol) in DME (140 ml) and water (20 ml) was refluxed under nitrogen overnight. After cooling to room temperature, the solid was collected by filtration, washed with methanol, re-dissolved in hot toluene and filtered through a short plug of silica gel. Upon evaporation of the solvent, the crude product was recrystallized from toluene to yield Compound 158 (3.2 g, 5.63 mmol, 72.6% yield) as a white solid.

Application in Electroluminescent Devices

All devices were fabricated by high vacuum (~$10^{-7}$ Torr) thermal evaporation. The anode electrode was 80 nm of indium tin oxide (ITO). The cathode electrode consisted of 1 nm of LiF followed by 100 nm of Al. All devices were encapsulated with a glass lid sealed with an epoxy resin in a nitrogen glove box (<1 ppm of H$_2$O and O$_2$) immediately after fabrication, and a moisture getter was incorporated inside the package.

DEVICE EXAMPLE

The OLED devices have organic stacks consisting of, sequentially deposited, from the ITO surface, 10 nm of LG101 (from LG Chem) as the hole injection layer (HIL), 45 nm of HTM-1 as the hole-transport layer (HTL), and 30 nm of Host-1 doped with 12 wt % of GD-1 as the emissive layer (EML). 5 nm of Host-1 was deposited on top of the EML as the hole blocking layer (HBL), followed by 40 nm of Compound 5 or comparative compounds (CC-1, CC-2 and CC-3) as the electron-transport layer (ETL). The structures of the compounds used are shown below:

Comparative Compounds

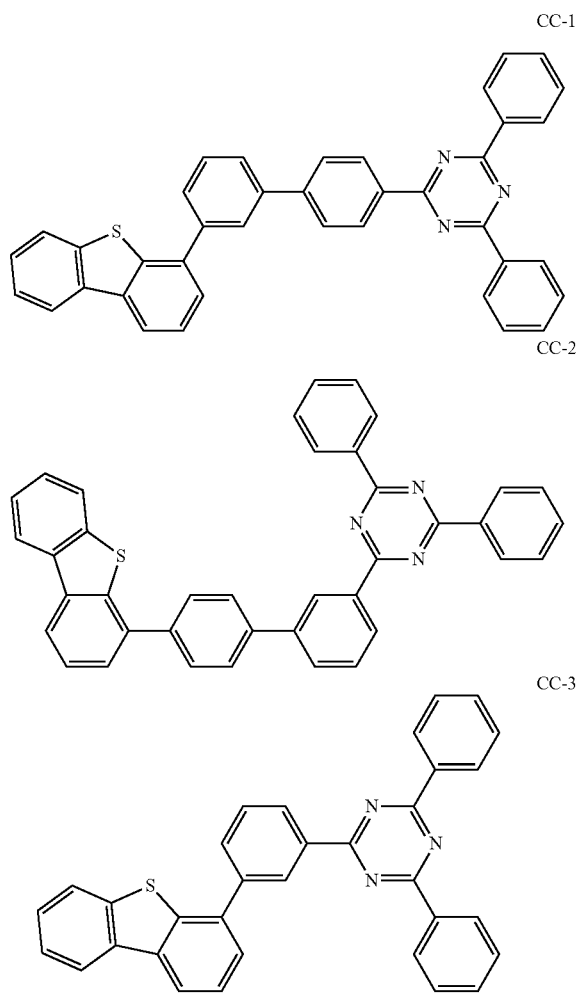

Table 1 below is a summary of the device data, where emission color, voltage (V) and power efficiency (PE) were recorded at a current density of 10 mA/cm², while the lifetime (LT90) defined as the time required for the device to decay to 90% of its initial luminance was recorded at a constant current density of 40 mA/cm². The lifetime data were normalized to that of Device 1.

| Device ID | ETL | Color | V [V] | PE [lm/W] | Relative LT90 |
|---|---|---|---|---|---|
| Device 1 | Compound 5 | Green | 7.1 | 16.0 | 1.00 |
| Device C-1 | CC-1 | Green | 10.2 | 12.5 | 0.49 |
| Device C-2 | CC-2 | Green | 10.6 | 13.8 | 0.76 |
| Device C-3 | CC-3 | Green | 10.5 | 13.2 | 0.18 |

The device data presented in Table 1 show that the device using the inventive Compound 5 as the ETL has a lower voltage, higher efficiency (PE) and longer lifetime (LT90) than the devices using comparative compounds CC-1, CC-2 or CC-3 as the ETL. Since both the inventive compounds and comparative compounds contain an electron-deficient triazine moiety, it is surprising that introducing one additional electron-deficient moiety, i.e., diaza-dibenzothiophene, in the inventive compounds significantly improves their performance as ETL.

The novel compounds described in this disclosure are useful as electron-transporting hosts in the emissive layer of an OLED. The molecules of the invented compounds have two electron-transporting parts: one electron-deficient part (benzothienopyrimidines and benzofuropyrimidines, or benzothienopyrazines and benzofuropyrazines) and another electron-deficient part that may consist of a variety of N-containing heterocycles. These parts may be connected directly to each other, or separated by a spacer. Such structure provides strong electron-conducting properties and allows these compounds to be used as electron-conducting hosts in red, green, yellow, and white OLED devices.

Aza-dibenzothiophenes and aza-dibenzofurans have been used as host materials in phosphorescent OLED devices, however, analogs with two N atom in one cycle is not known. Synthetic approaches to such compounds were widely studied in organic chemistry for preparation of drugs and pesticides. Thus, one can get a variety of benzothienopyrimidines and benzofuropyrimidine with different substituents. Such substituents allow tuning materials' electrochemical and photophysical properties, such as HOMO, LUMO, triplet energy etc., and their thermal properties, such as glass transition temperature, melting point, evaporation temperature and decomposition temperature, etc.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having the formula $G^1$-L-$G^2$, Formula I; wherein $G^1$ has the structure:

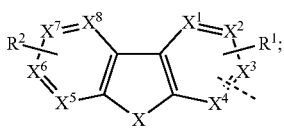

wherein X is selected from the group consisting of O, S, and Se;
wherein each of $X^1$, $X^2$, $X^3$, $X^4$, $X^5$, $X^6$, $X^7$, and $X^8$ is carbon or nitrogen;
wherein at least one of $X^1$, $X^2$, $X^3$, $X^4$, $X^5$, $X^6$, $X^7$, and $X^8$ is nitrogen;
wherein at least one of $X^1$, $X^2$, $X^3$, and $X^4$ is a carbon and bonded to L;
wherein $R^1$, $R^2$, $R^3$, and $R^4$ independently represent mono substitution up to the maximum possible substitutions or no substitution;
wherein $R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R^1$ and $R^2$ substitutions are optionally joined to form a fused ring;

wherein G² is selected from the group consisting of

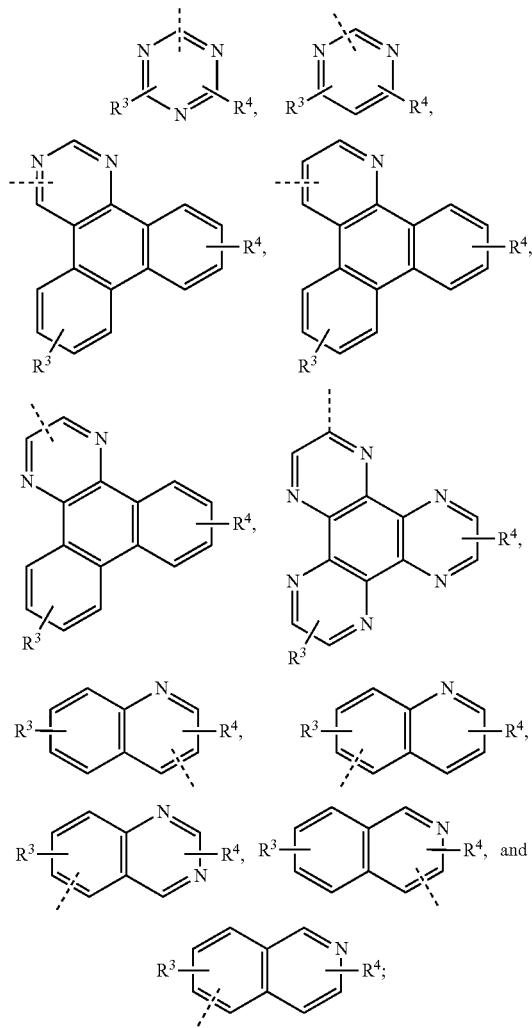

wherein when G² is

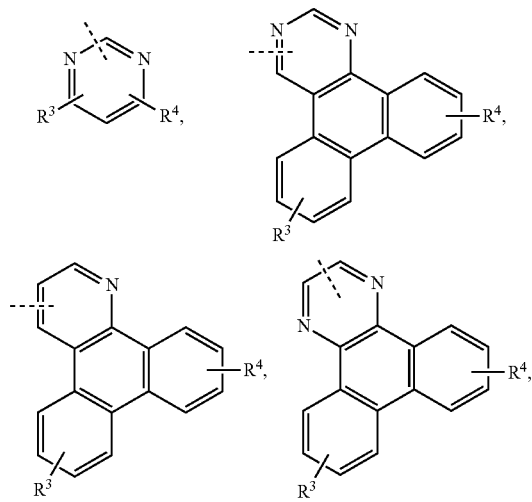

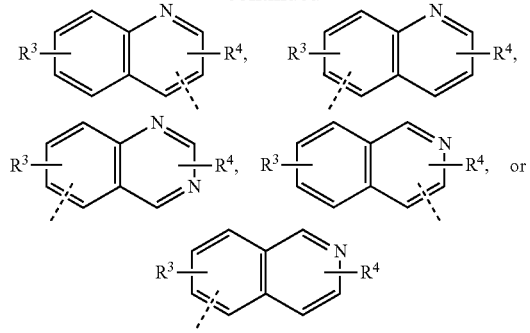

R³ and R⁴ substitutions are optionally joined to form a fused ring;
wherein G² bonds to L at a carbon atom of G²; and
wherein L is selected from the group consisting of benzene, biphenyl, terphenyl, naphthalene, triphenylene, dibenzofuran, dibenzothiophene, dibenzoselenophene, fluorene, pyridine, pyrimidine, pyridazine, pyrazine, quinoline, quinoxaline, naphthyridine, and combinations thereof; wherein L is optionally further unfused substituted with one or more groups selected from hydrogen, deuterium, alkyl, cycloalkyl, aralkyl, alkoxy, aryloxy, amino, silyl, aryl, heteroaryl, and combinations thereof.

2. The compound of claim 1, wherein X is O or S.

3. The compound of claim 1, wherein only one of $X^1$, $X^2$, $X^3$, $X^4$, $X^5$, $X^6$, $X^7$, and $X^8$ is nitrogen.

4. The compound of claim 1, wherein only two of $X^1$, $X^2$, $X^3$, $X^4$, $X^5$, $X^6$, $X^7$, and $X^8$ are nitrogen.

5. The compound of claim 1, wherein only two of $X^1$, $X^2$, $X^3$, $X^4$, $X^5$, $X^6$, $X^7$, and $X^8$ are nitrogen and the two nitrogen atoms are on the same ring.

6. The compound of claim 1, wherein only two of $X^1$, $X^2$, $X^3$, and $X^4$ are nitrogen and $X^5$, $X^6$, $X^7$, and $X^8$ are carbon items.

7. The compound of claim 1, wherein G¹ is selected from the group consisting of:

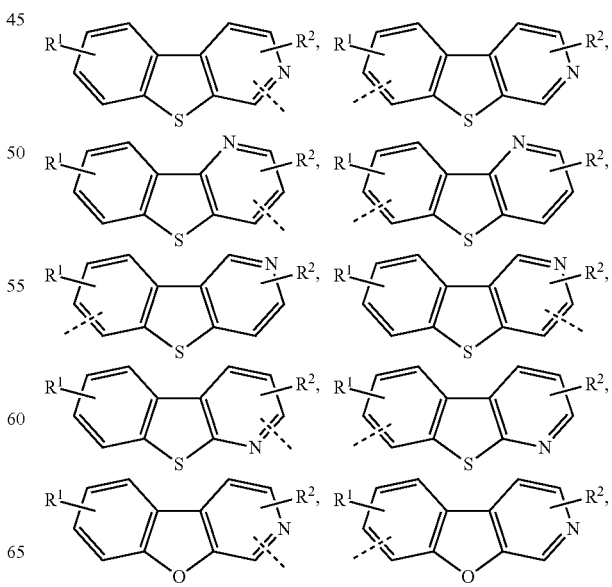

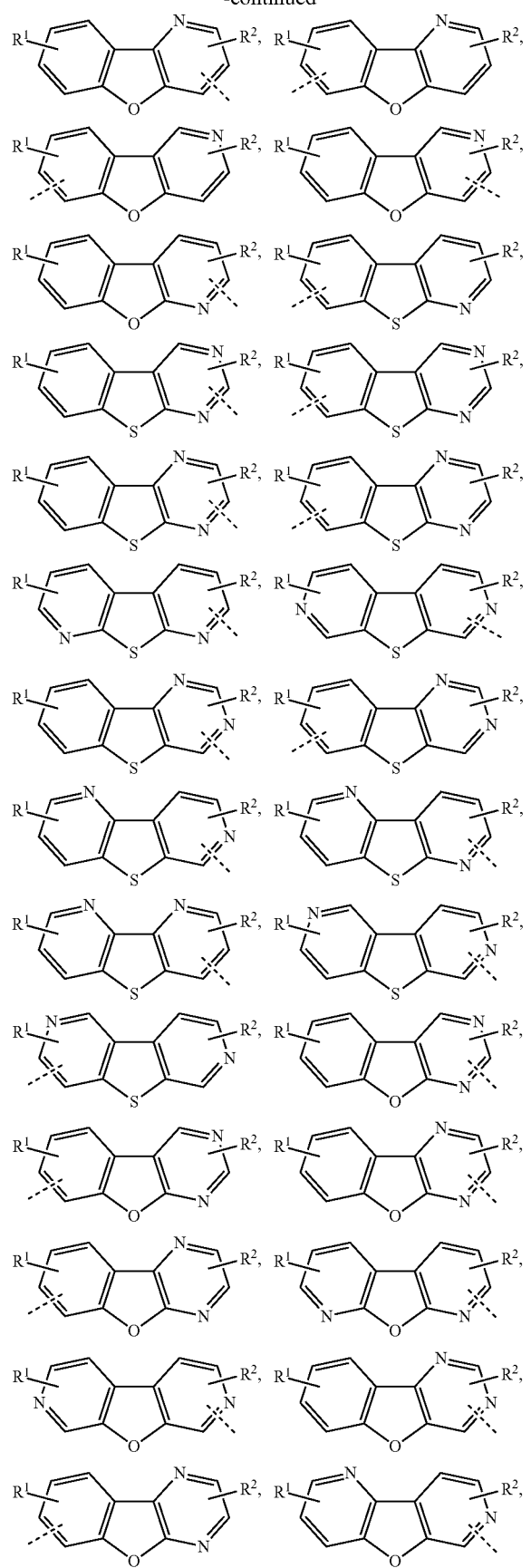
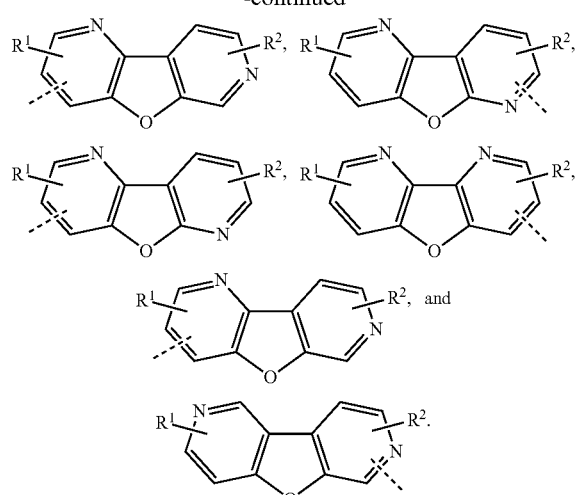
8. The compound of claim 1, wherein L is selected from the group consisting of:
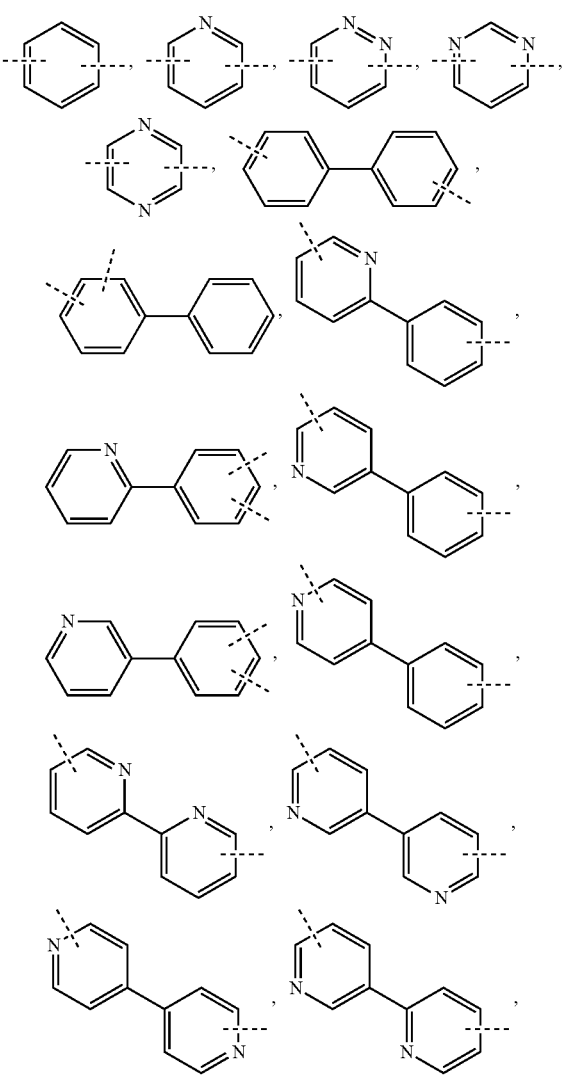

221
-continued
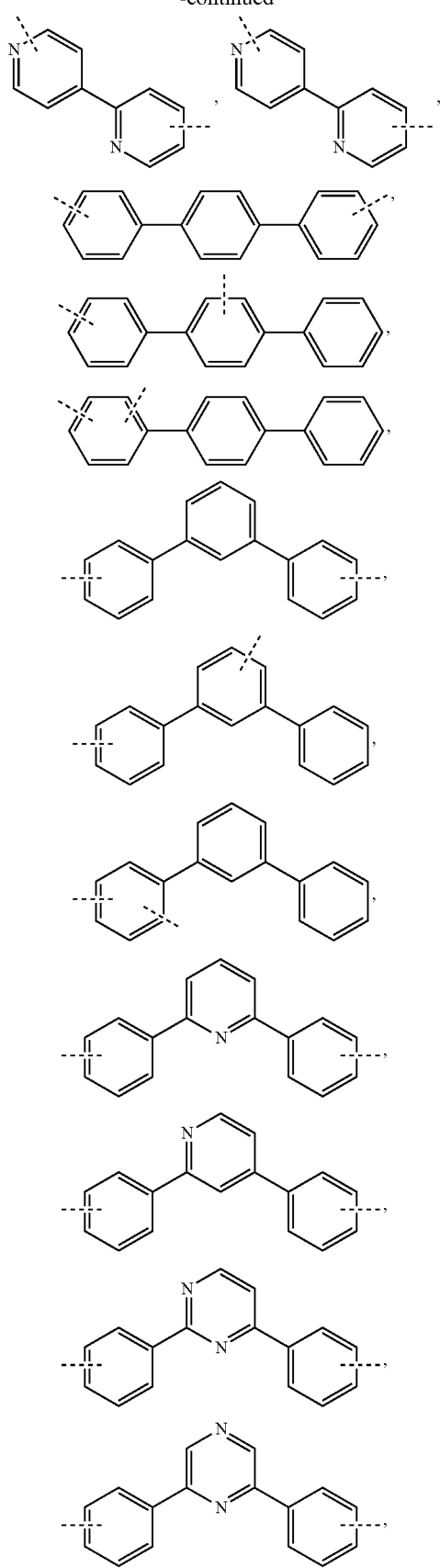
222
-continued
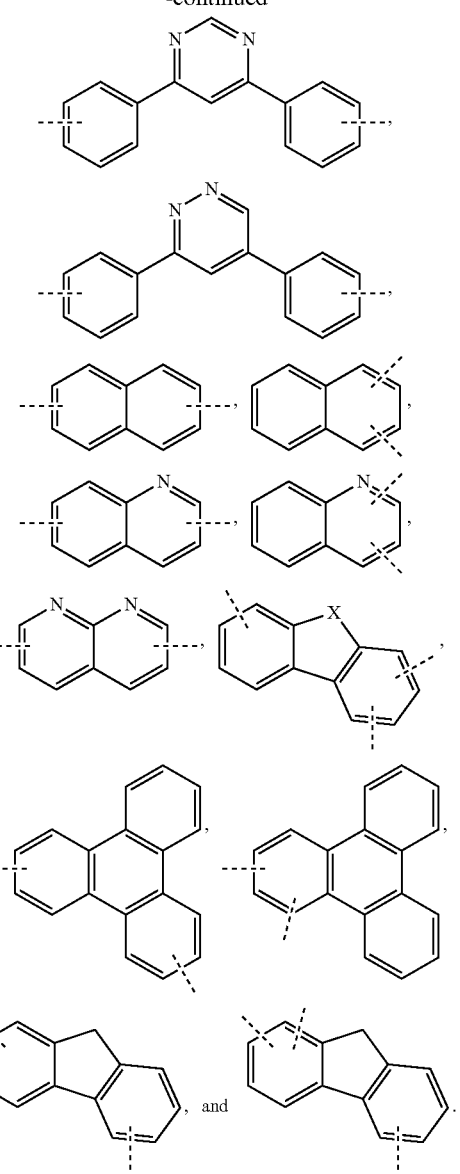
9. The compound of claim 1, wherein $G^1$ is selected from the group consisting of:
D1
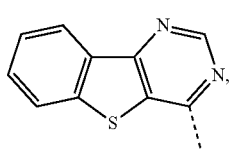
D2
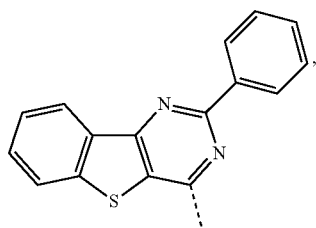

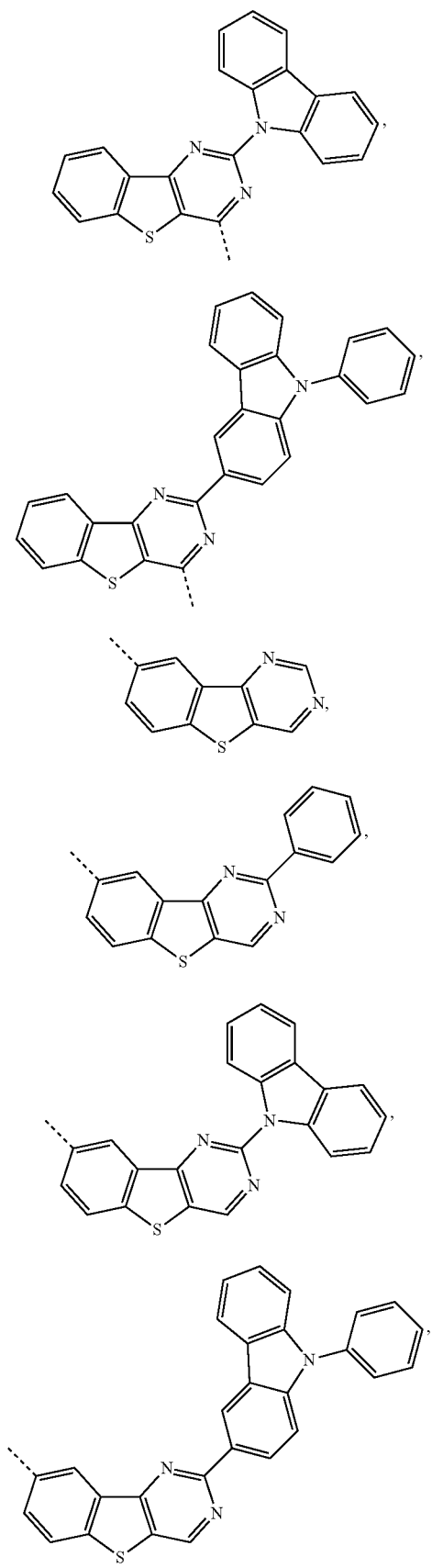

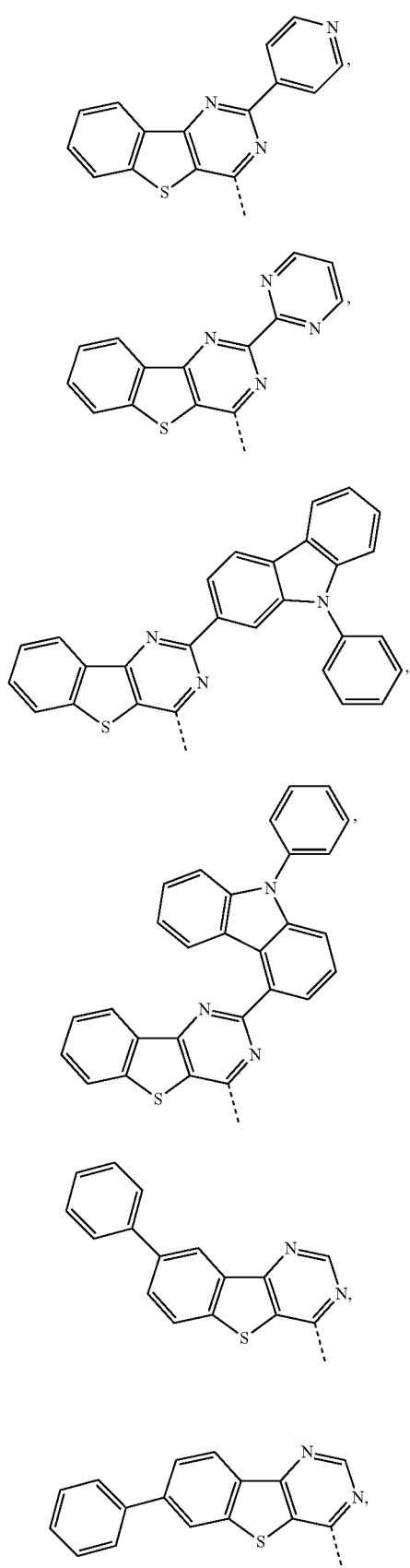
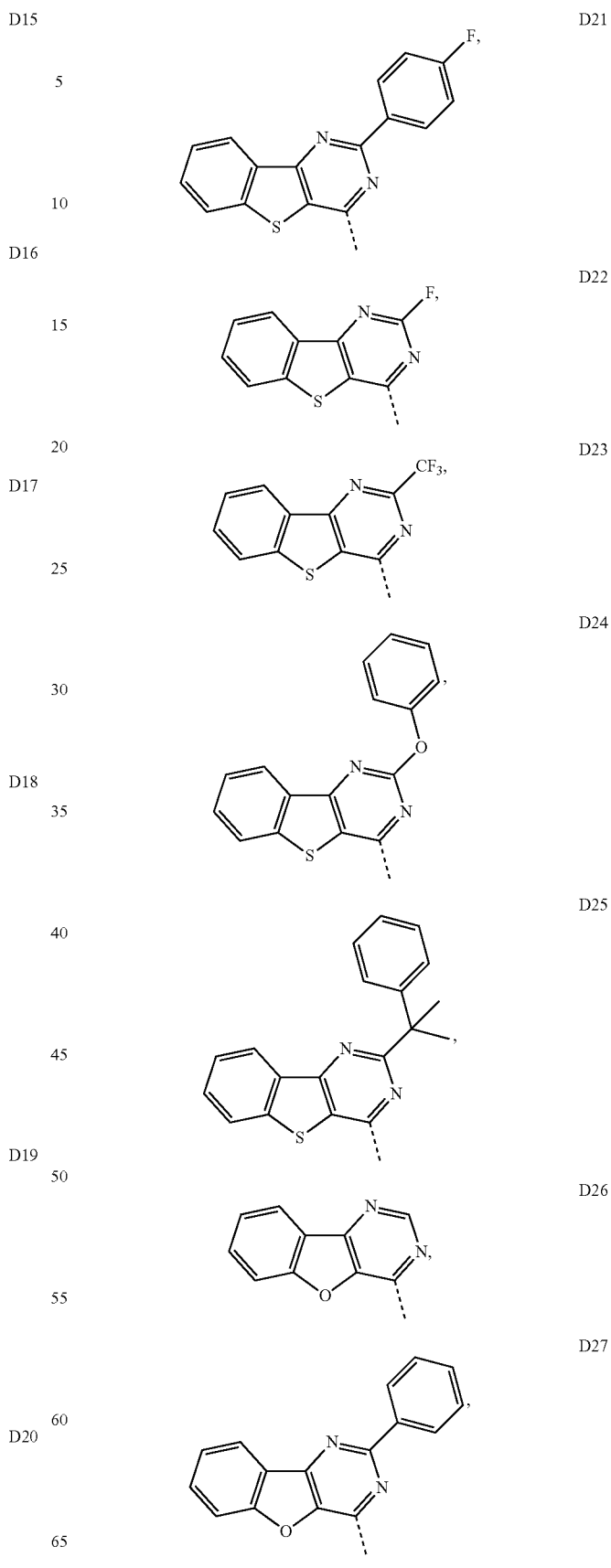

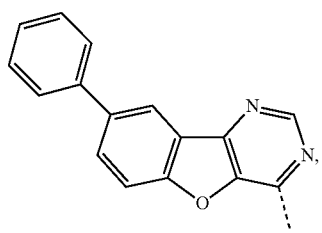
D28
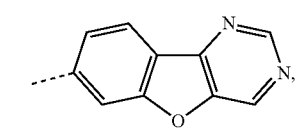
D29
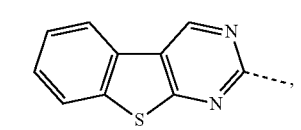
D30
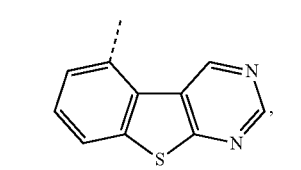
D31
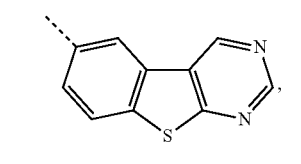
D32
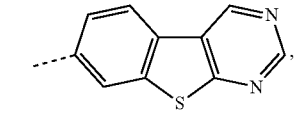
D33
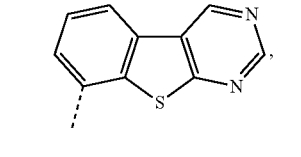
D34
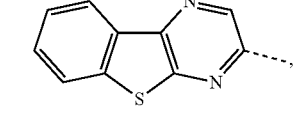
D35
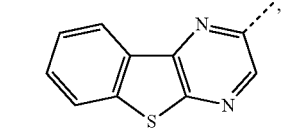
D36
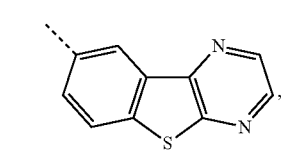
D37
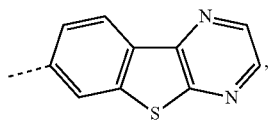
D38
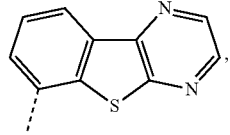
D39
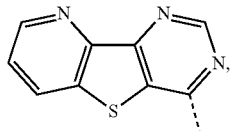
D40
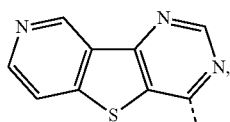
D41
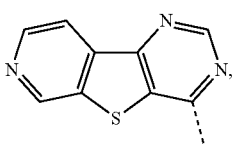
D42
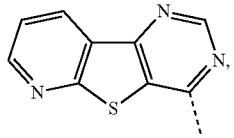
D43
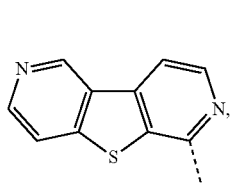
D44
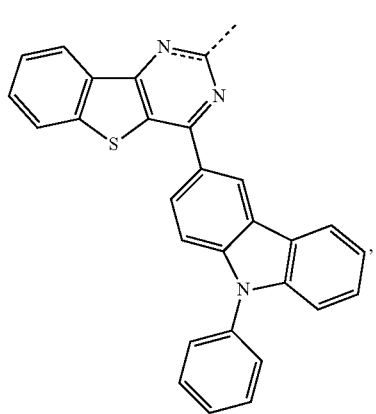
D45

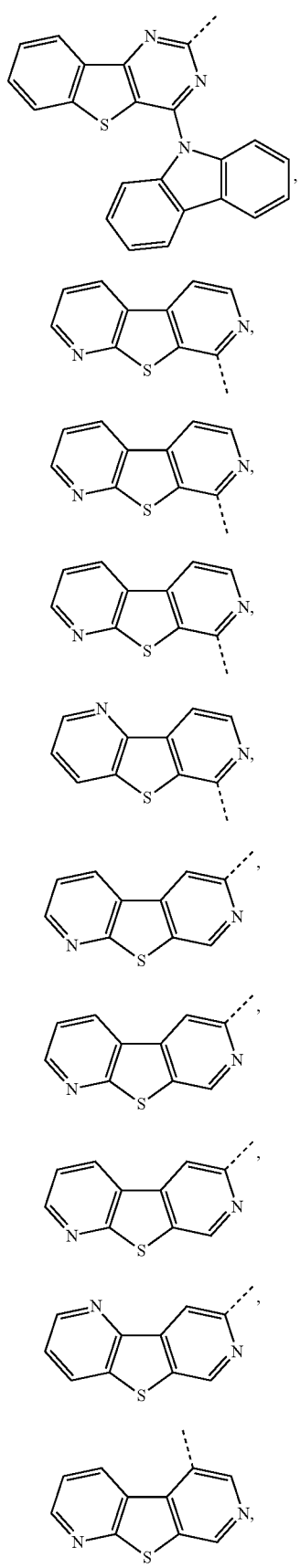
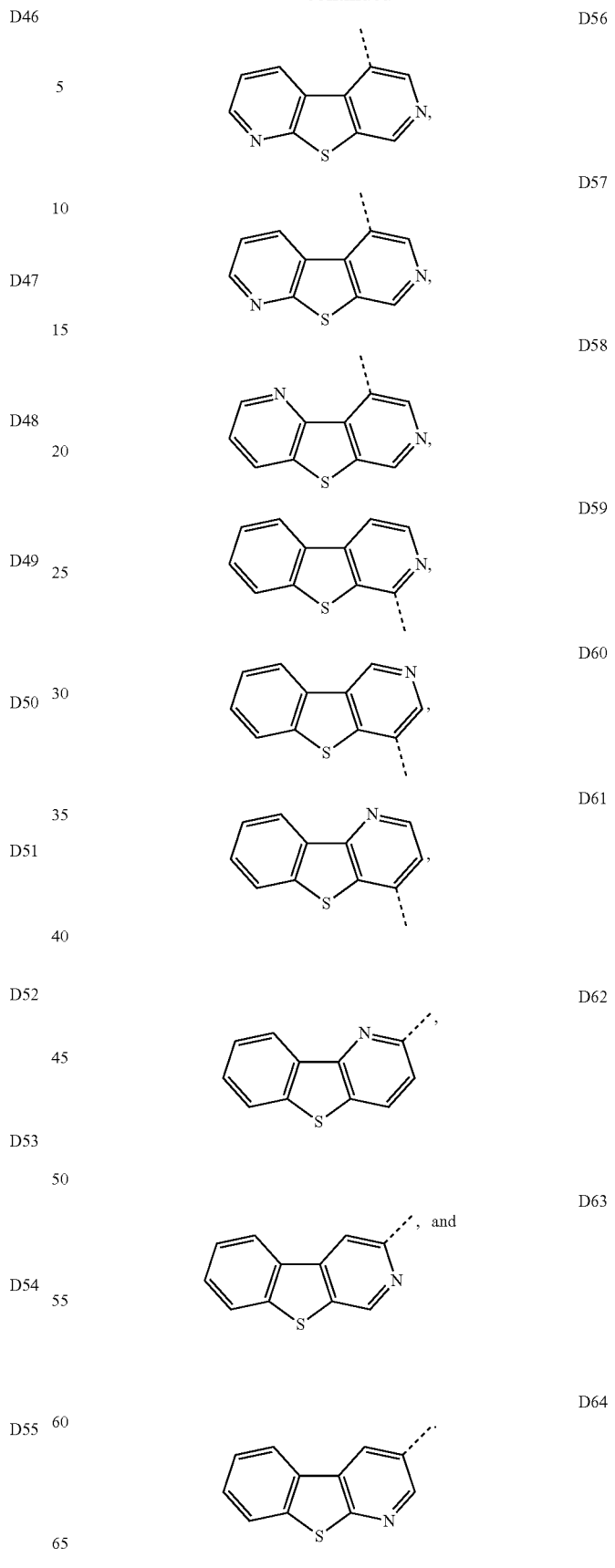

10. The compound of claim 1, wherein L is selected from the group consisting of:
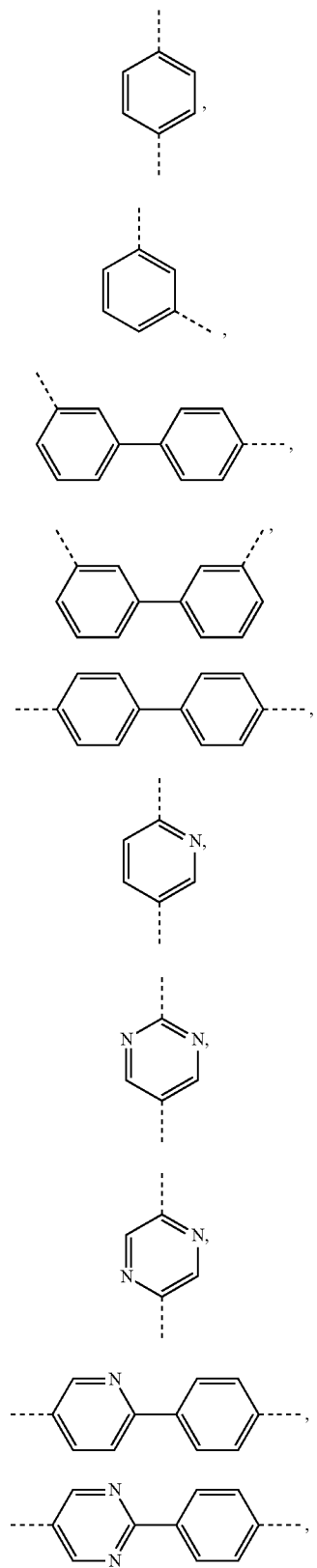
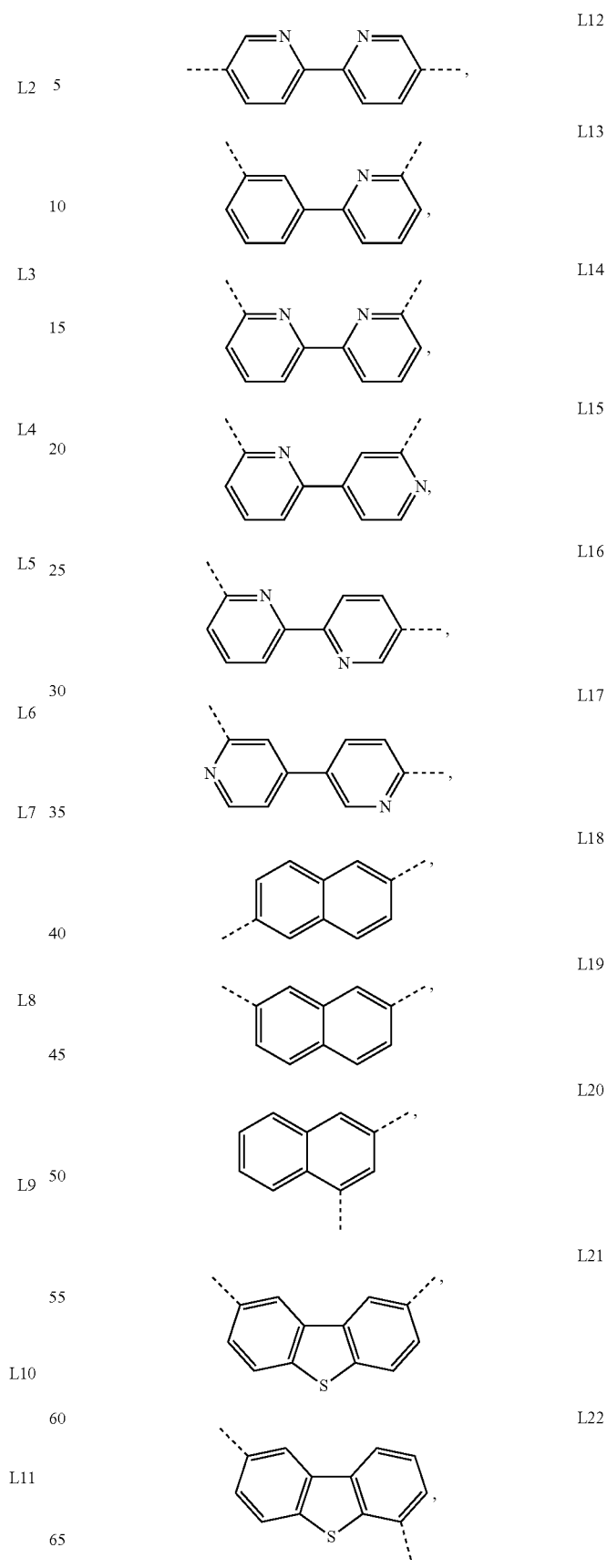

-continued

L23: [dibenzothiophene, 4,6-linked]

L24: [dibenzothiophene, 2,8-linked]

L25: [dibenzofuran, 2,8-linked]

L26: [dibenzofuran, 4,6-linked]

L27: [dibenzofuran, 3,7-linked]

L28: [m-terphenyl, 3,3''-linked]

L29: [m-terphenyl variant]

L30: [p-terphenyl]

L31: [3,5-biphenyl]

L32: [terphenyl variant]

L33: [9,9-dimethylfluorene, 2,7-linked]

L34: [triphenylene], and

L35: [triphenylene]

11. A device comprising one or more organic light emitting devices, wherein at least one of the one or more organic light emitting devices comprising:
  an anode;
  a cathode; and
  an organic layer, disposed between the anode and the cathode, comprising a compound having the formula $G^1$-L-$G^2$, Formula I,
  wherein $G^1$ has the structure:

$$R^2\text{-}X^6=X^7=X^8\text{-}X^1=X^2\text{-}R^1$$
[core structure with $X^5$–X–$X^4$ ring]

wherein X is selected from the group consisting of O, S, and Se;
wherein each of $X^1$, $X^2$, $X^3$, $X^4$, $X^5$, $X^6$, $X^7$, $X^8$, is carbon or nitrogen;
wherein at least two of $X^1$, $X^2$, $X^3$, $X^4$, $X^5$, $X^6$, $X^7$, and $X^8$ are nitrogen;
wherein at least one of $X^1$, $X^2$, $X^3$, and $X^4$ is a carbon and bonded to L;

wherein R¹, R², R³, and R⁴ independently represent mono substitution up to the maximum possible substitutions or no substitution;

wherein R¹, R², R³, and R⁴ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein R¹ and R² substitutions are optionally joined to form a fused ring;

wherein G² is selected from the group consisting of

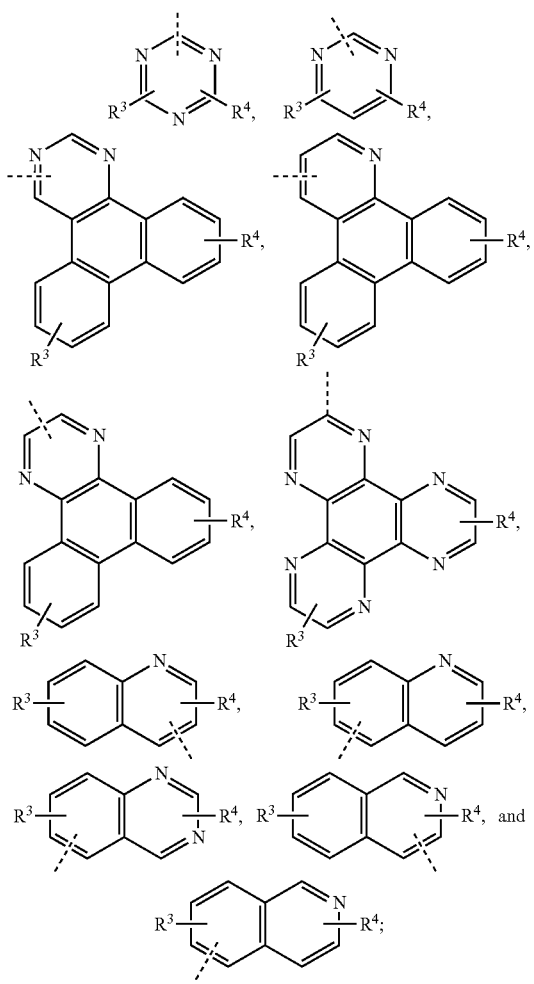

wherein when G² is

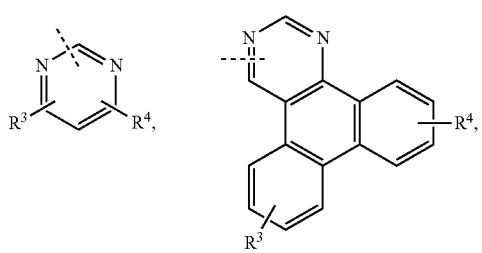

-continued

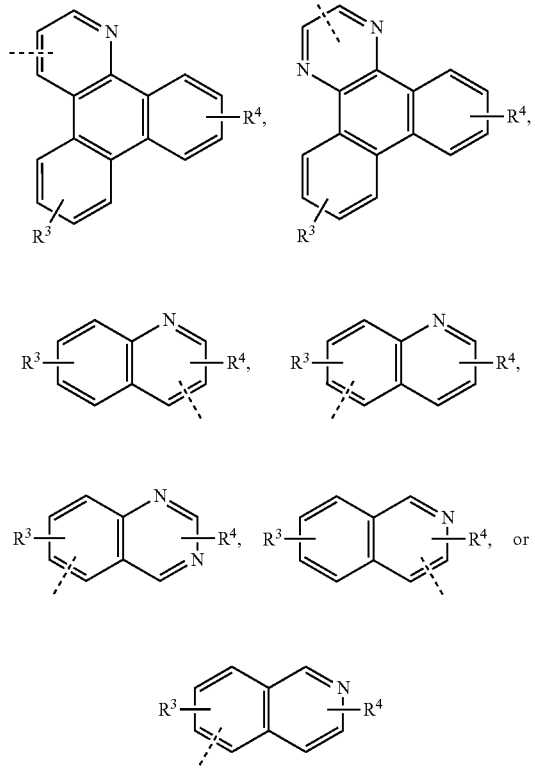

$R^3$ and $R^4$ substitutions are optionally joined to form a fused ring;

wherein G² bonds to L at a carbon atom of G²; and wherein L is selected from the group consisting of benzene, biphenyl, terphenyl, naphthalene, triphenylene, dibenzofuran, dibenzothiophene, dibenzoselenophene, fluorene, pyridine, pyrimidine, pyridazine, pyrazine, quinoline, quinoxaline, naphthyridine, and combinations thereof; wherein L is optionally further unfused substituted with one or more groups selected from hydrogen, deuterium, alkyl, cycloalkyl, aralkyl, alkoxy, aryloxy, amino, silyl, aryl, heteroaryl, and combinations thereof.

12. The device of claim 11, wherein the organic layer is an emissive layer and the compound of Formula I is a host.

13. The device of claim 11, wherein the organic layer further comprises a phosphorescent emissive dopant that is a transition metal complex having at least one ligand or part of the ligand if the ligand is more than bidentate selected from the group consisting of:

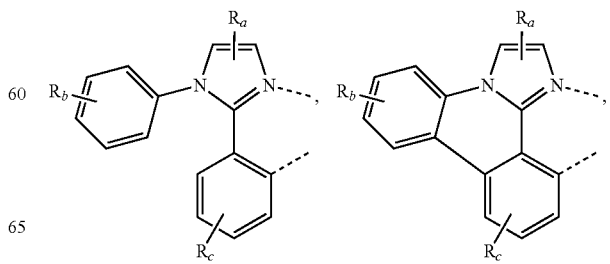

237
-continued
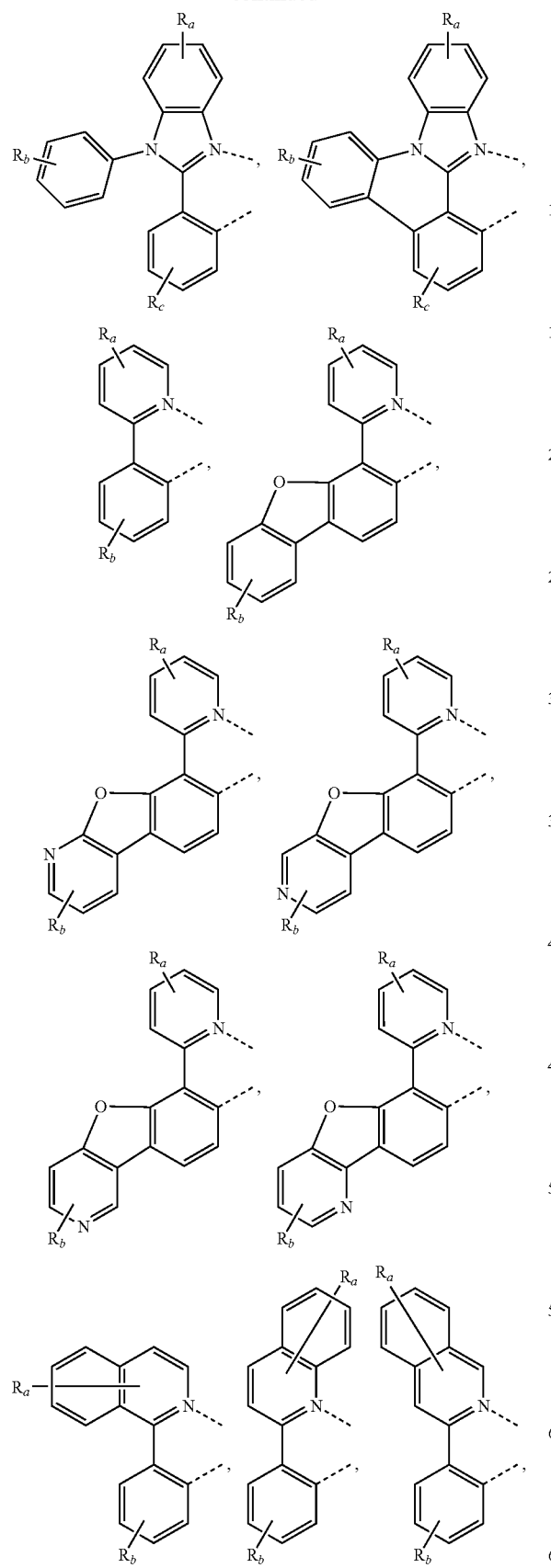
238
-continued
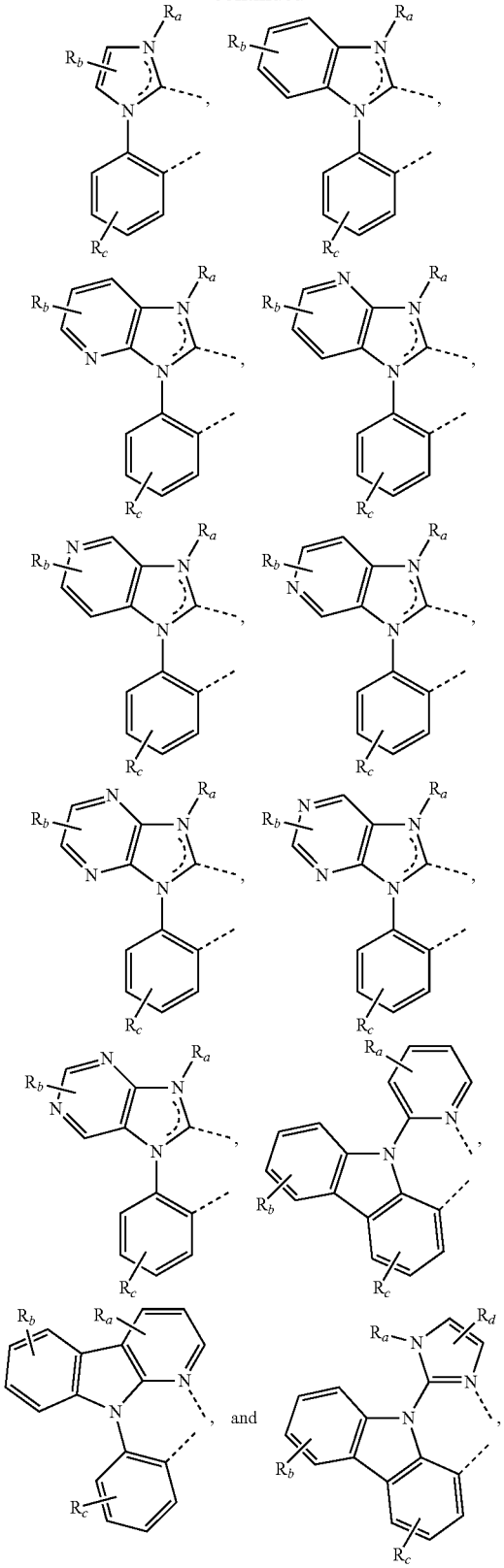
wherein $R_a$, $R_b$, $R_c$, and $R_d$ may represent mono, di, tri, or tetra substitution, or no substitution;
wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

14. The device of claim 11, wherein the device is selected from the group consisting of a consumer product, an electronic component module, an organic light-emitting device, and a lighting panel.

15. The device of claim 11, wherein the organic layer is a blocking layer and the compound is a blocking material in the organic layer.

16. The device of claim 11, wherein the organic layer is an electron transport layer and the compound is an electron transporting material in the organic layer.

17. A formulation comprising a compound having the formula, $G^1$-L-$G^2$, Formula I;
wherein $G^1$ has the structure:

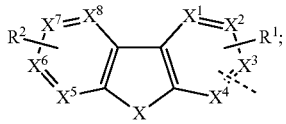

wherein X is selected from the group consisting of O, S, and Se;
wherein each of $X^1$, $X^2$, $X^3$, $X^4$, $X^5$, $X^6$, $X^7$, $X^8$, is carbon or nitrogen;
wherein at least one of $X^1$, $X^2$, $X^3$, $X^4$, $X^5$, $X^6$, $X^7$, and $X^8$ is nitrogen;
wherein at least one of $X^1$, $X^2$, $X^3$, and $X^4$ is a carbon and bonded to L;
wherein $R^1$, $R^2$, $R^3$, and $R^4$ independently represent mono substitution up to the maximum possible substitutions or no substitution;
wherein $R^1$, $R^2$, $R^3$, and $R^4$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R^1$ and $R^2$ substitutions are optionally joined to form a fused ring;
wherein $G^2$ is selected from the group consisting of

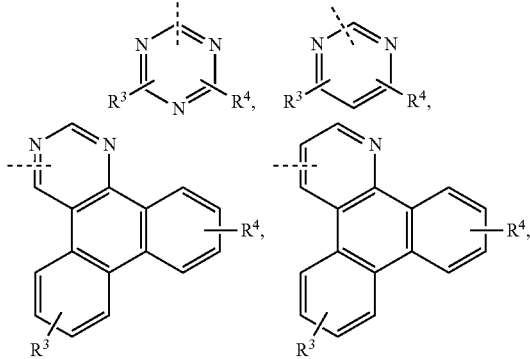

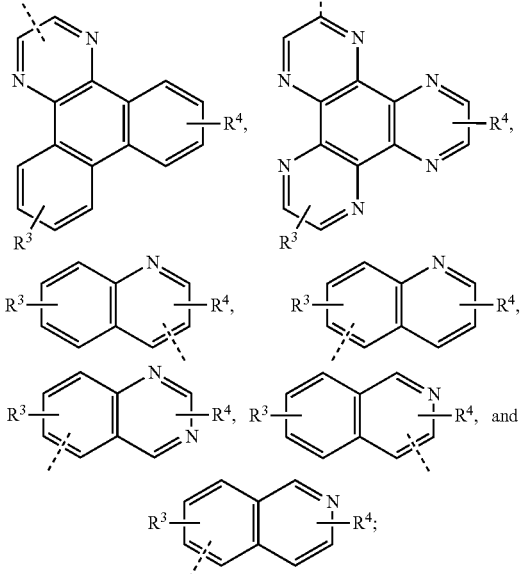

wherein when $G^2$ is

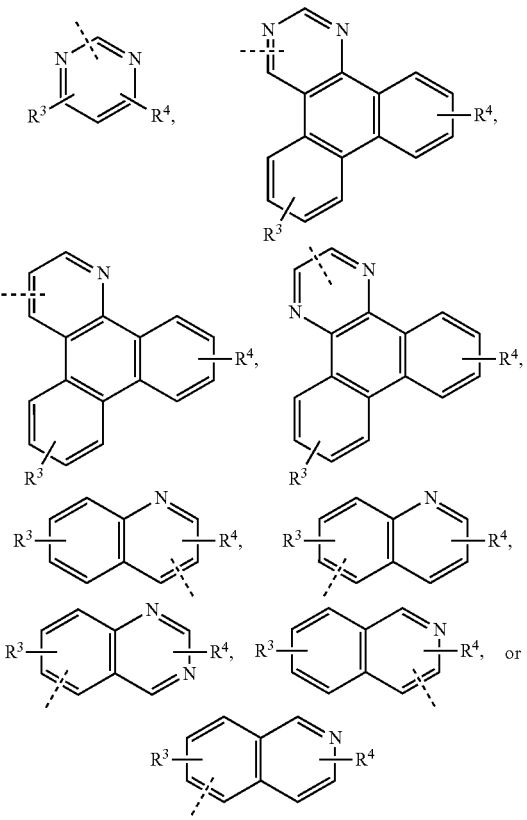

$R^3$ and $R^4$ substitutions are optionally joined to form a fused ring;
wherein $G^2$ bonds to L at a carbon atom of $G^2$; and
wherein L is selected from the group consisting of benzene, biphenyl, terphenyl, naphthalene, triphenylene, dibenzofuran, dibenzothiophene, dibenzoselenophene, fluorene, pyridine, pyrimidine, pyridazine, pyrazine, quinoline, quinoxaline, naphthyridine, and combinations thereof; wherein L is optionally further unfused substituted with one or more groups selected from hydrogen, deuterium, alkyl, cycloalkyl, aralkyl, alkoxy, aryloxy, amino, silyl, aryl, heteroaryl, and combinations thereof.

18. The compound of the claim 1, wherein G² is selected from the group consisting of:

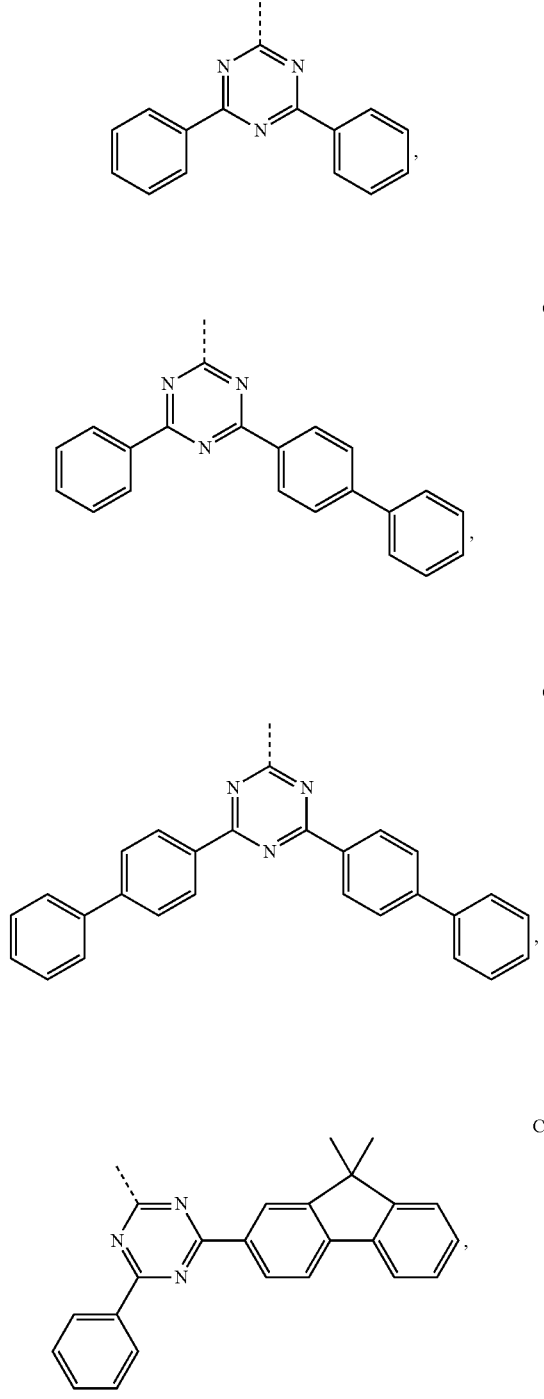

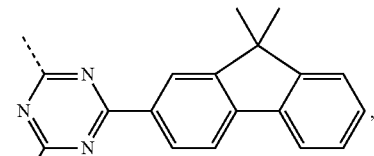

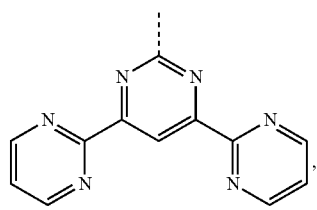

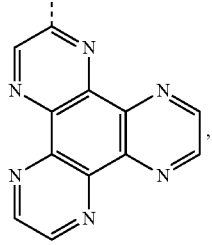

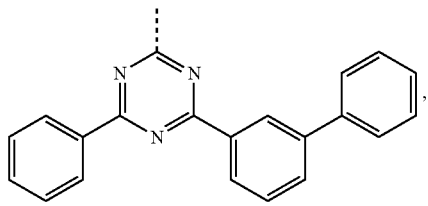

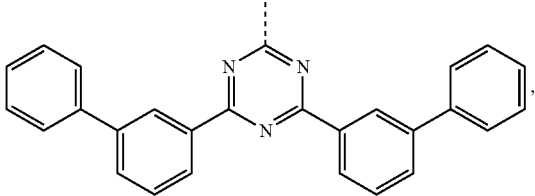

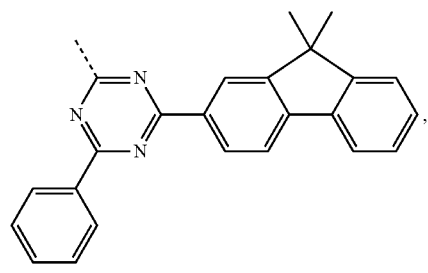

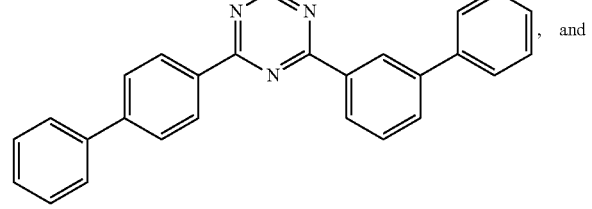

-continued

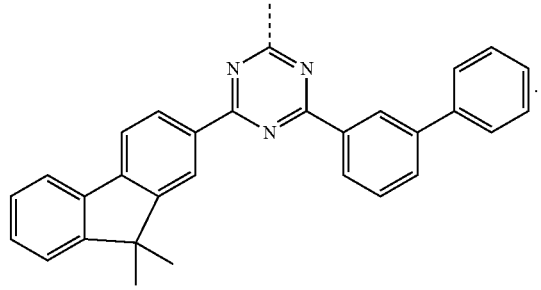
C20

19. A compound of claim 1, wherein the compound is selected from a group consisting of:

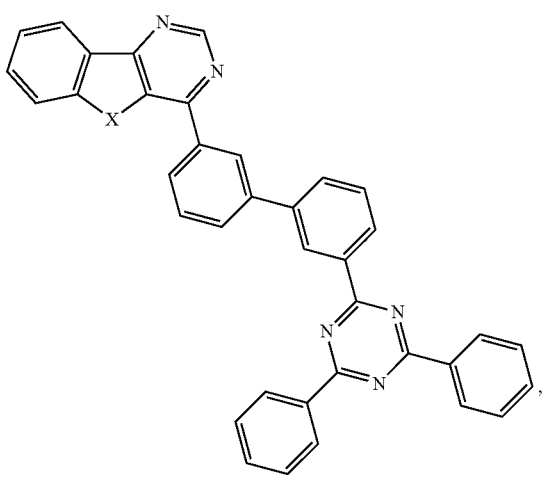

wherein Compound 1 is when X = O,
Compound 2 is when X = S, and
Compound 3 is when X = Se

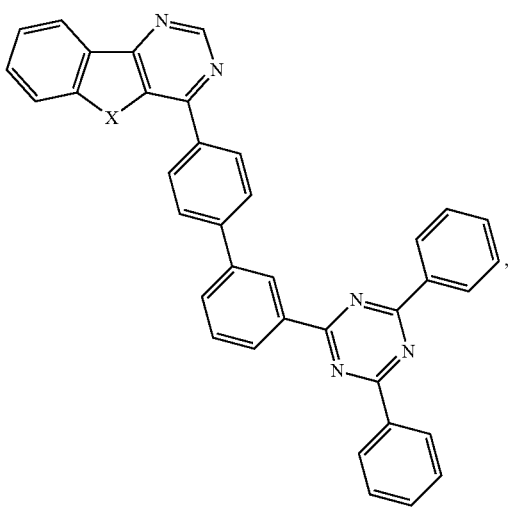

wherein Compound 4 is when X = O,
Compound 5 is when X = S, and
Compound 6 is when X = Se -continued

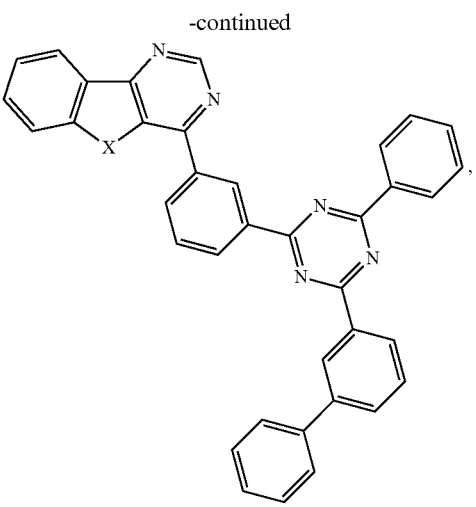

wherein Compound 7 is when X = O,
Compound 8 is when X = S, and
Compound 9 is when X = Se

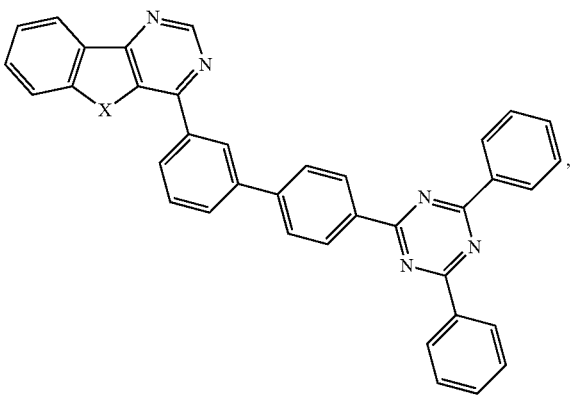

wherein Compound 10 is when X = O,
Compound 11 is when X = S, and
Compound 12 is when X = Se

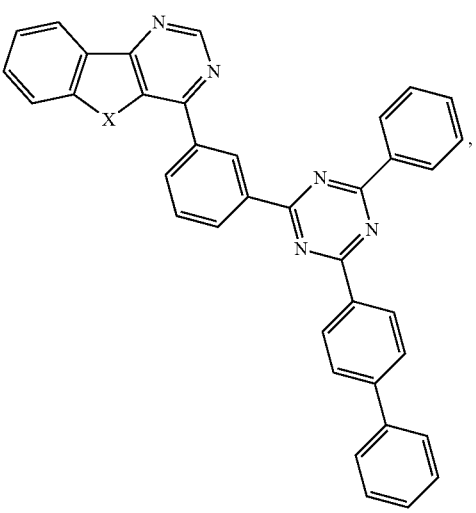

wherein Compound 13 is when X = O,
Compound 14 is when X = S, and
Compound 15 is when X = Se

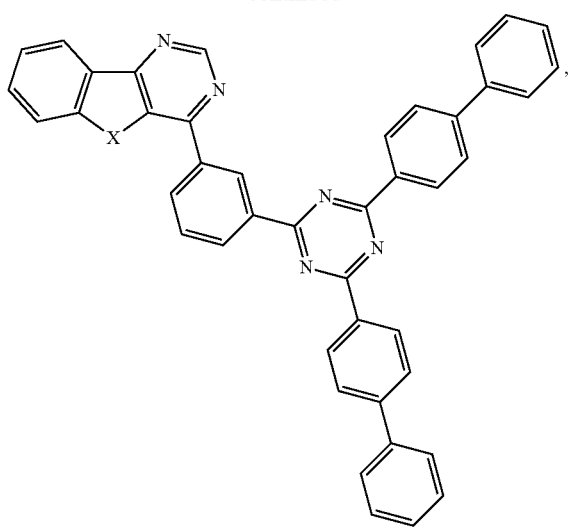

wherein Compound 16 is when X = O,
Compound 17 is when X = S, and
Compound 18 is when X = Se

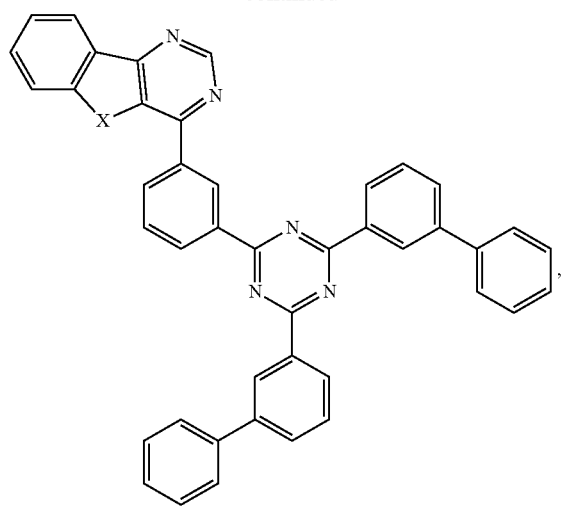

wherein Compound 22 is when X = O,
Compound 23 is when X = S, and
Compound 24 is when X = Se

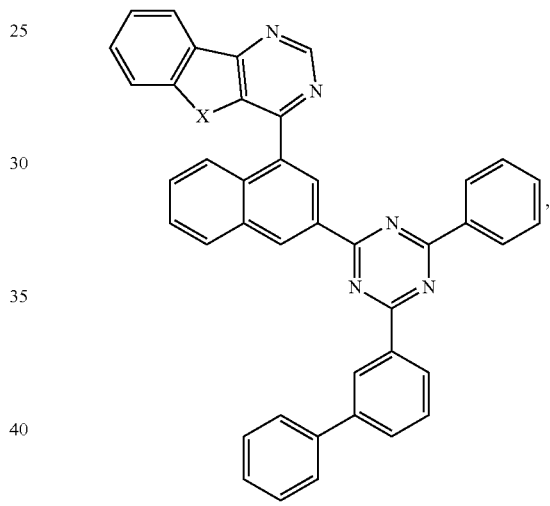

wherein Compound 25 is when X = O,
Compound 26 is when X = S, and
Compound 27 is when X = Se

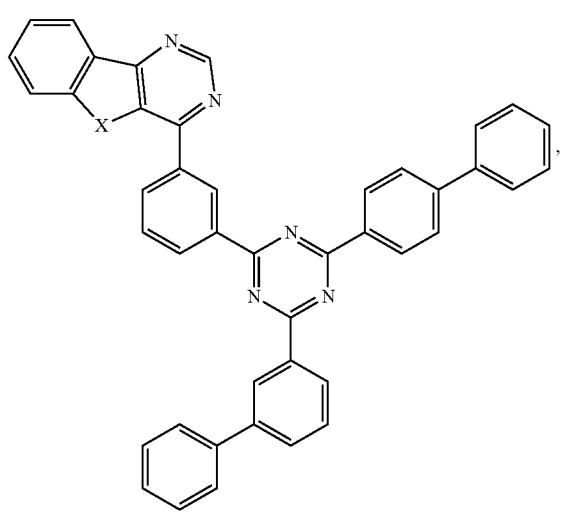

wherein Compound 19 is when X = O,
Compound 20 is when X = S, and
Compound 21 is when X = Se

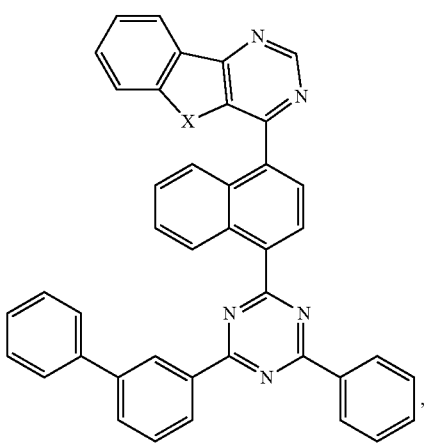

wherein Compound 28 is when X = O,
Compound 29 is when X = S, and
Compound 30 is when X = Se -continued

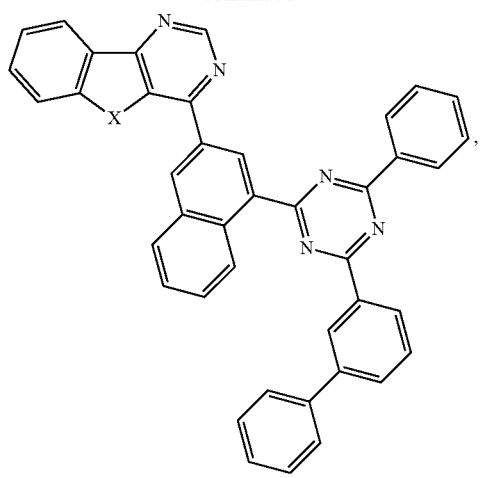

wherein Compound 31 is when X = O,
Compound 32 is when X = S, and
Compound 33 is when X = Se

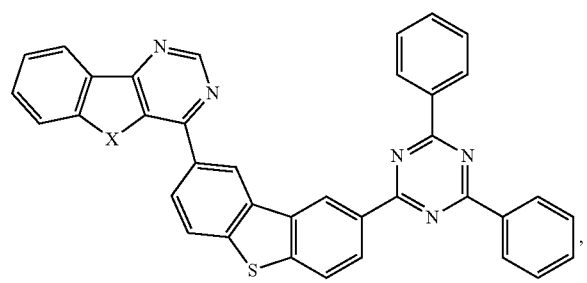

wherein Compound 34 is when X = O,
Compound 35 is when X = S, and
Compound 36 is when X = Se

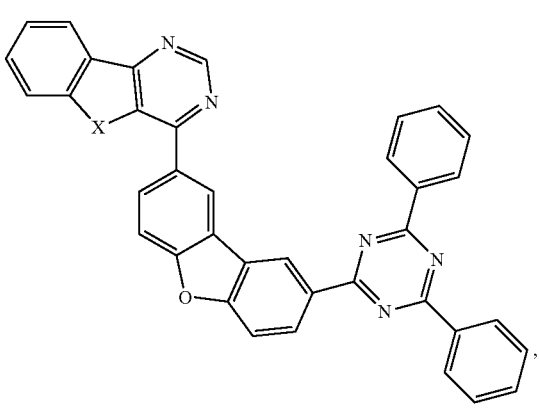

wherein Compound 37 is when X = O,
Compound 38 is when X = S, and
Compound 39 is when X = Se -continued

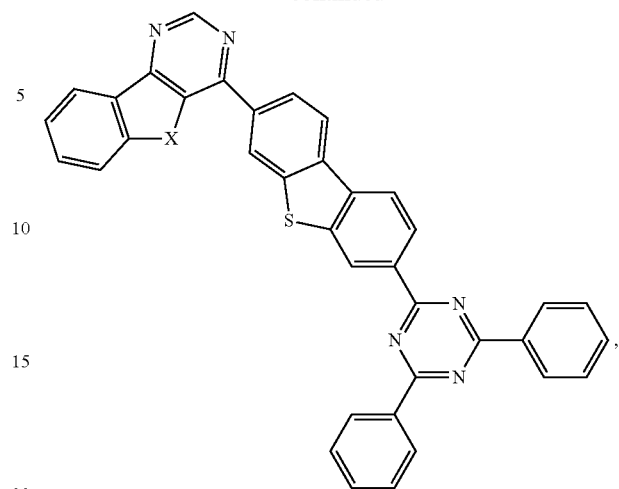

wherein Compound 40 is when X = O,
Compound 41 is when X = S, and
Compound 42 is when X = Se

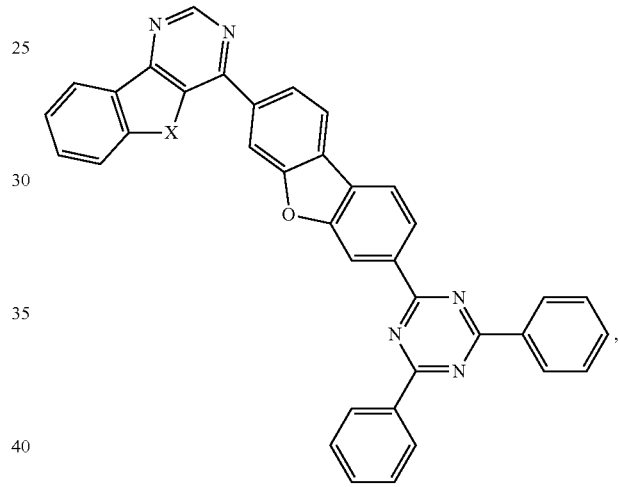

wherein Compound 43 is when X = O,
Compound 44 is when X = S, and
Compound 45 is when X = Se

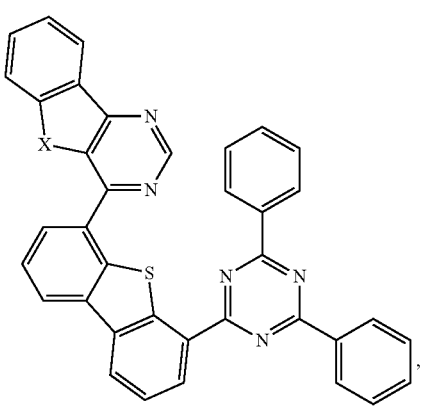

wherein Compound 46 is when X = O,
Compound 47 is when X = S, and
Compound 48 is when X = Se -continued

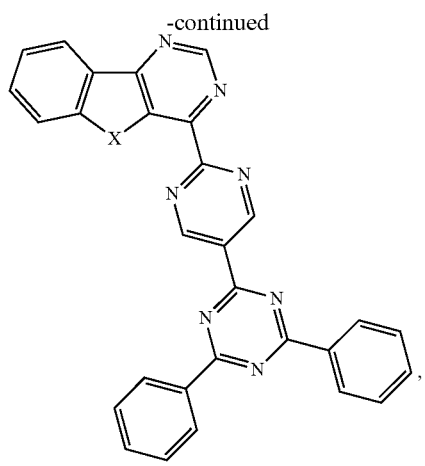

wherein Compound 49 is when X = O,
Compound 50 is when X = S, and
Compound 51 is when X = Se

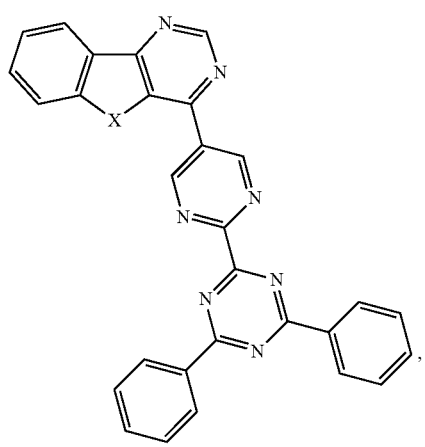

wherein Compound 52 is when X = O,
Compound 53 is when X = S, and
Compound 54 is when X = Se

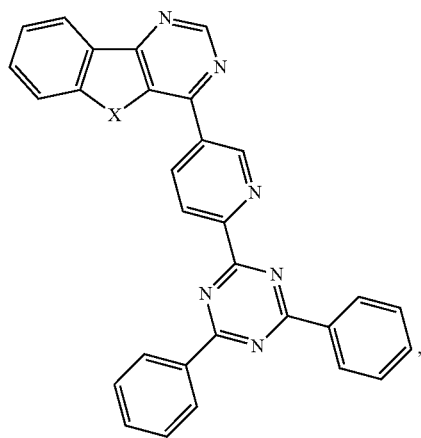

wherein Compound 55 is when X = O,
Compound 56 is when X = S, and
Compound 57 is when X = Se -continued

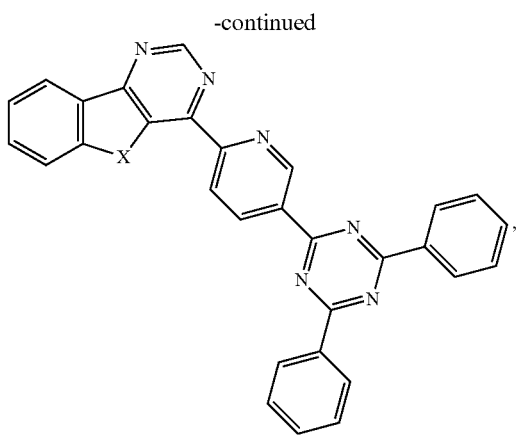

wherein Compound 58 is when X = O,
Compound 59 is when X = S, and
Compound 60 is when X = Se

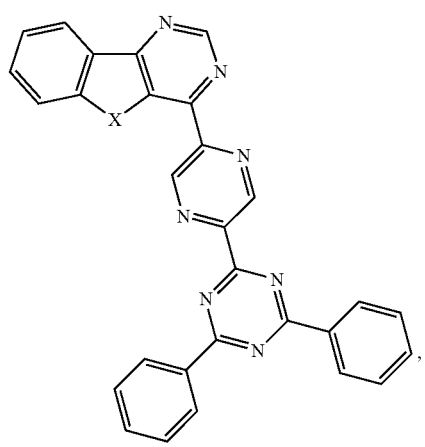

wherein Compound 61 is when X = O,
Compound 62 is when X = S, and
Compound 63 is when X = Se

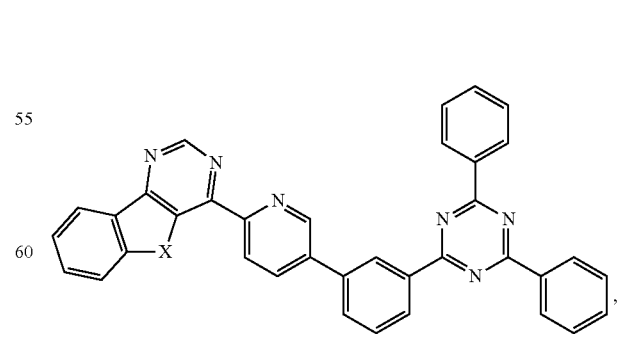

wherein Compound 64 is when X = O,
Compound 65 is when X = S, and
Compound 66 is when X = Se

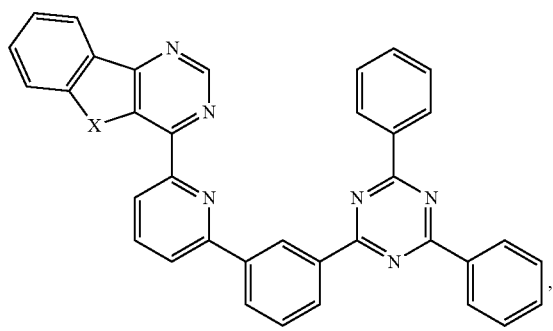

wherein Compound 67 is when X = O,
Compound 68 is when X = S, and
Compound 69 is when X = Se

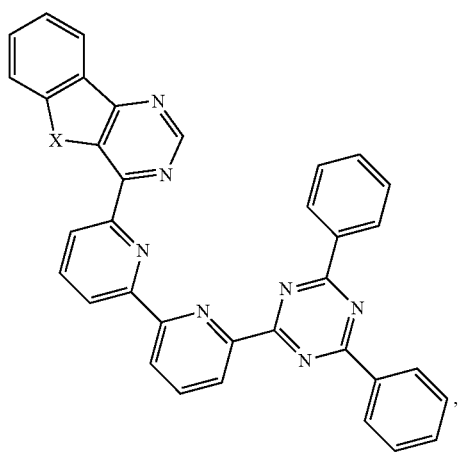

wherein Compound 70 is when X = O,
Compound 71 is when X = S, and
Compound 72 is when X = Se

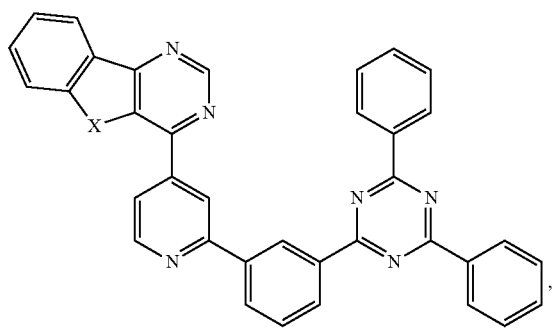

wherein Compound 73 is when X = O,
Compound 74 is when X = S, and
Compound 75 is when X = Se

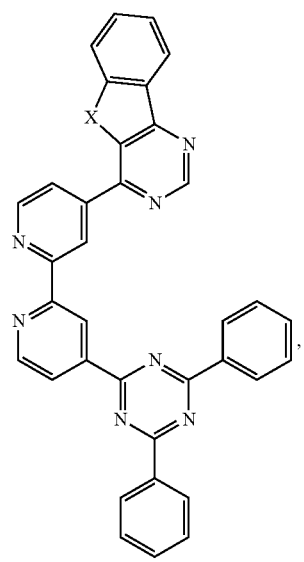

wherein Compound 76 is when X = O,
Compound 77 is when X = S, and
Compound 78 is when X = Se

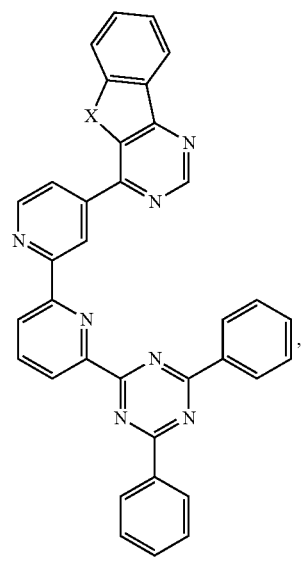

wherein Compound 79 is when X = O,
Compound 80 is when X = S, and
Compound 81 is when X = Se 253
-continued

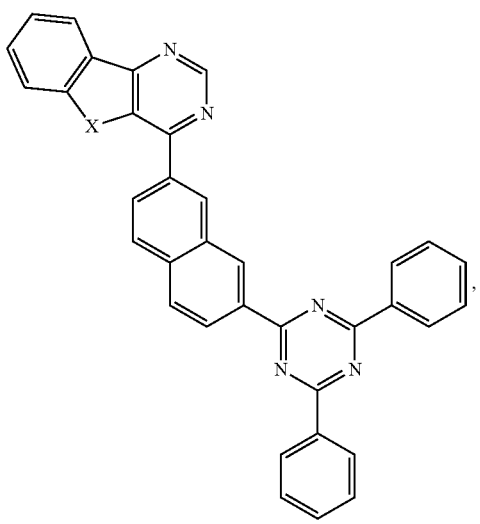

wherein Compound 82 is when X = O,
Compound 83 is when X = S, and
Compound 84 is when X = Se

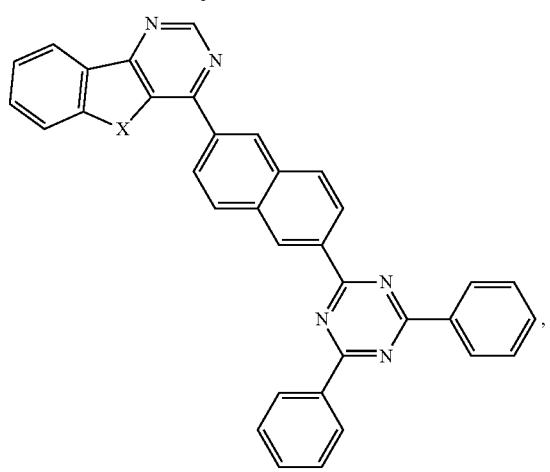

wherein Compound 85 is when X = O,
Compound 86 is when X = S, and
Compound 87 is when X = Se

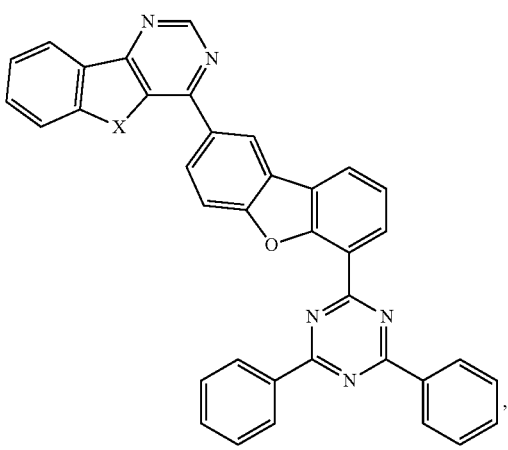

wherein Compound 88 is when X = O,
Compound 89 is when X = S, and
Compound 90 is when X = Se 254
-continued

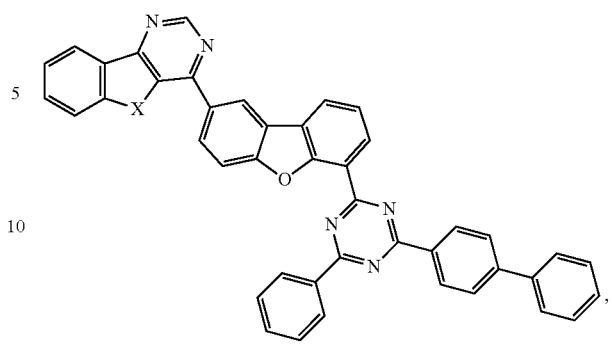

wherein Compound 91 is when X = O,
Compound 92 is when X = S, and
Compound 93 is when X = Se

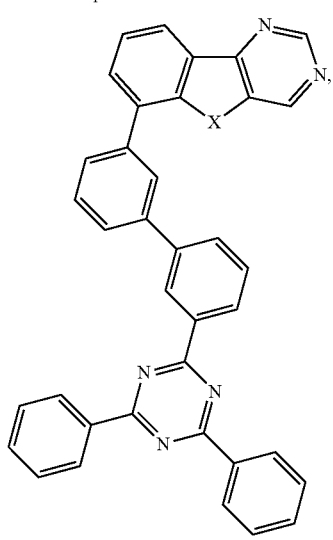

wherein Compound 94 is when X = O,
Compound 95 is when X = S, and
Compound 96 is when X = Se

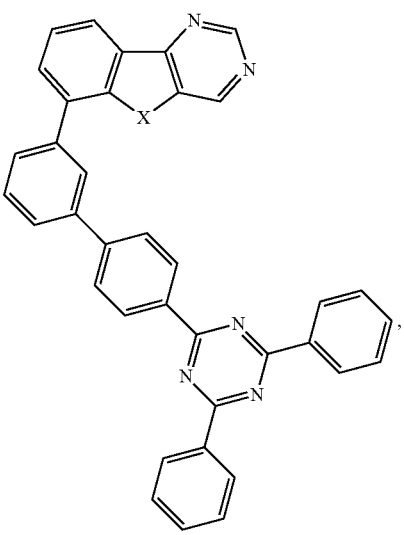

wherein Compound 97 is when X = O,
Compound 98 is when X = S, and
Compound 99 is when X = Se -continued

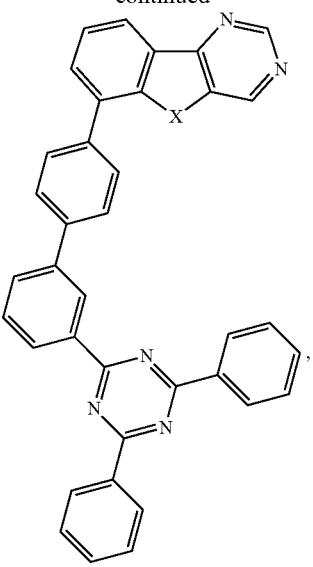

wherein Compound 100 is when X = O,
Compound 101 is when X = S, and
Compound 102 is when X = Se

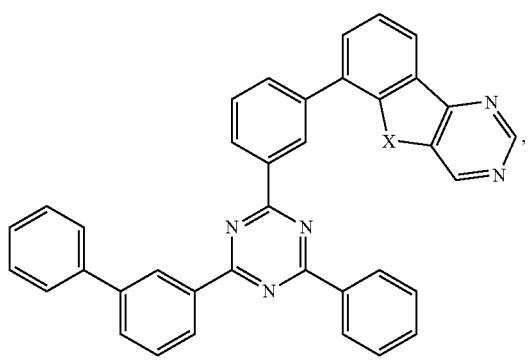

wherein Compound 103 is when X = O,
Compound 104 is when X = S, and
Compound 105 is when X = Se

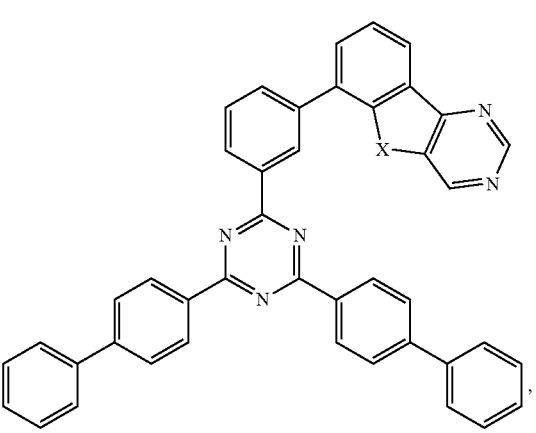

wherein Compound 106 is when X = O,
Compound 107 is when X = S, and
Compound 108 is when X = Se -continued

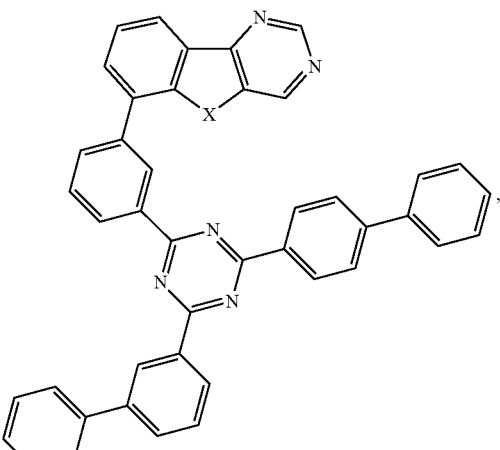

wherein Compound 109 is when X = O,
Compound 110 is when X = S, and
Compound 111 is when X = Se

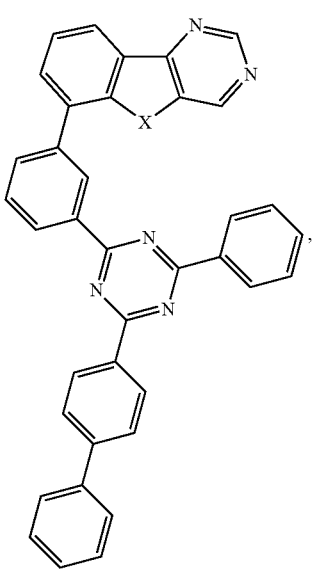

wherein Compound 112 is when X = O,
Compound 113 is when X = S, and
Compound 114 is when X = Se -continued

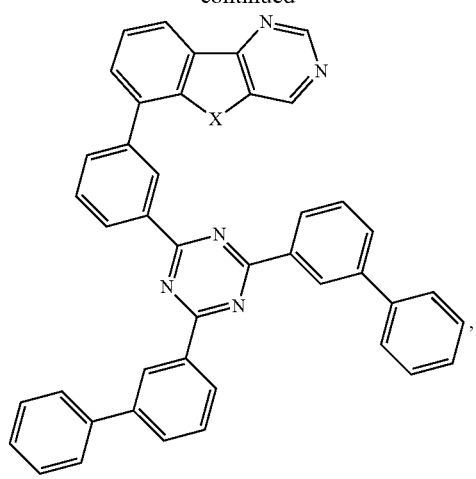

wherein Compound 115 is when X = O,
Compound 116 is when X = S, and
Compound 117 is when X = Se

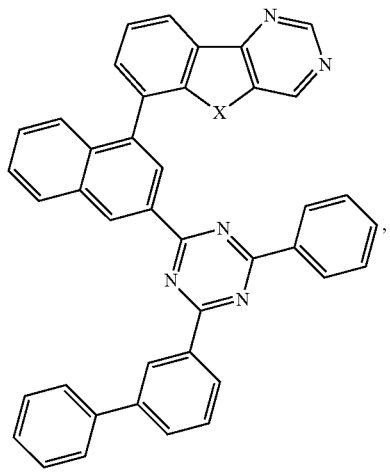

wherein Compound 118 is when X = O,
Compound 119 is when X = S, and
Compound 120 is when X = Se

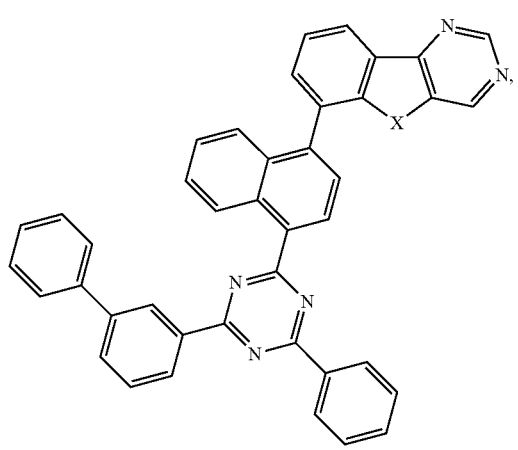

wherein Compound 121 is when X = O,
Compound 122 is when X = S, and
Compound 123 is when X = Se -continued

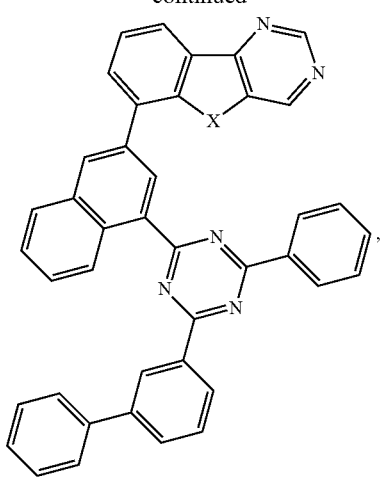

wherein Compound 124 is when X = O,
Compound 125 is when X = S, and
Compound 126 is when X = Se

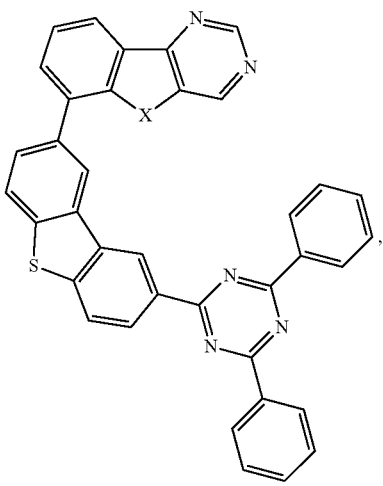

wherein Compound 127 is when X = O,
Compound 128 is when X = S, and
Compound 129 is when X = Se

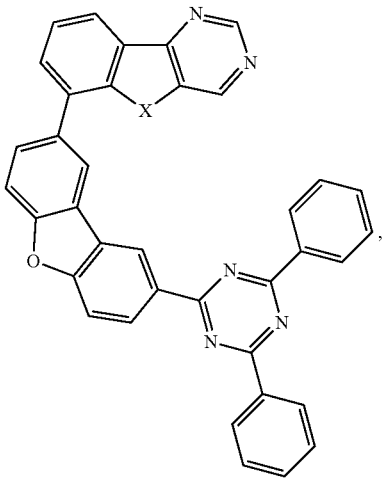

wherein Compound 130 is when X = O,
Compound 131 is when X = S, and
Compound 132 is when X = Se

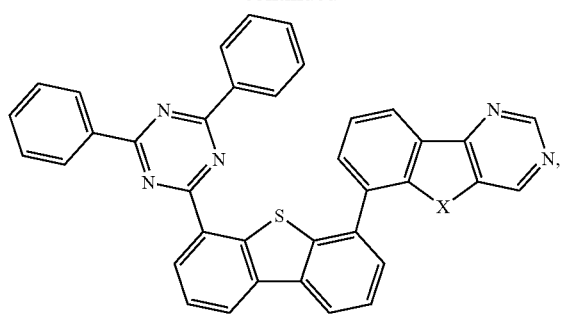

wherein Compound 133 is when X = O,
Compound 134 is when X = S, and
Compound 135 is when X = Se

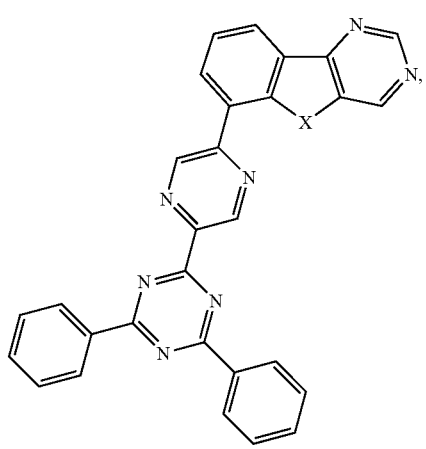

wherein Compound 136 is when X = O,
Compound 137 is when X = S, and
Compound 138 is when X = Se

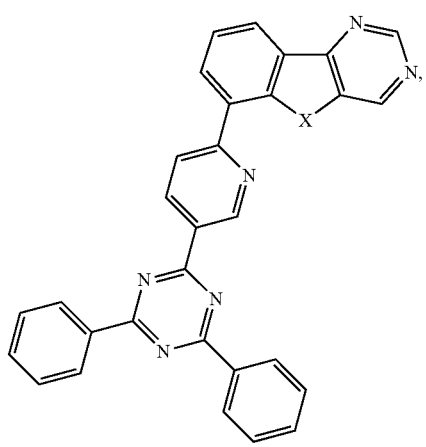

wherein Compound 139 is when X = O,
Compound 140 is when X = S, and
Compound 141 is when X = Se

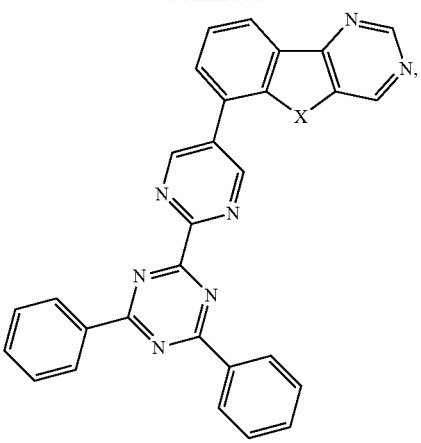

wherein Compound 142 is when X = O,
Compound 143 is when X = S, and
Compound 144 is when X = Se

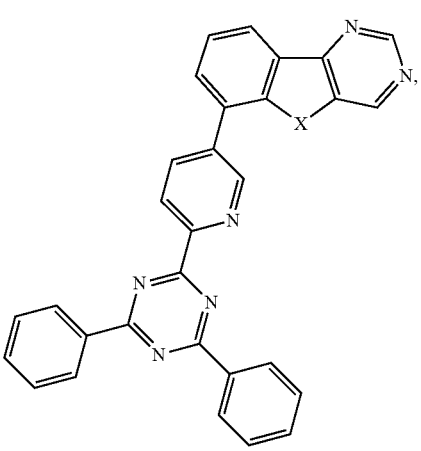

wherein Compound 145 is when X = O,
Compound 146 is when X = S, and
Compound 147 is when X = Se

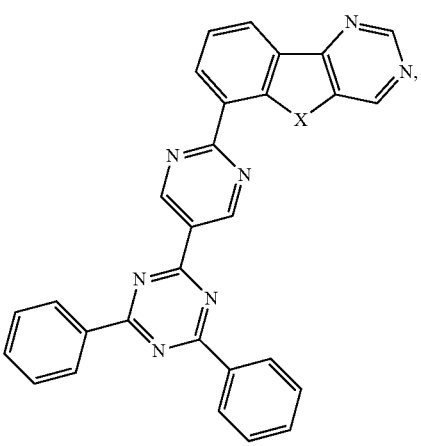

wherein Compound 148 is when X = O,
Compound 149 is when X = S, and
Compound 150 is when X = Se -continued

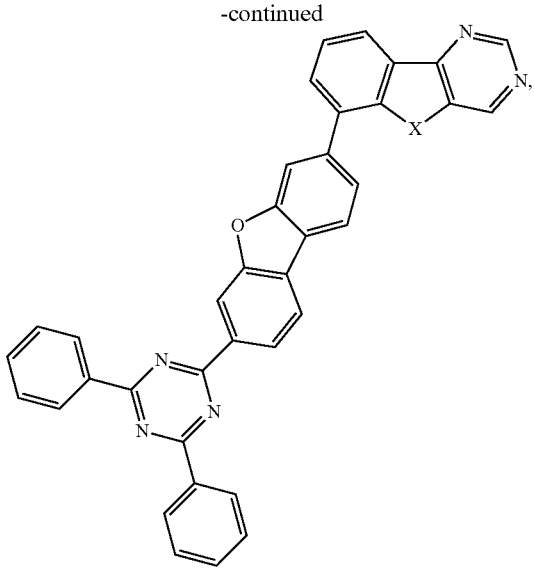

wherein Compound 151 is when X = O,
Compound 152 is when X = S, and
Compound 153 is when X = Se

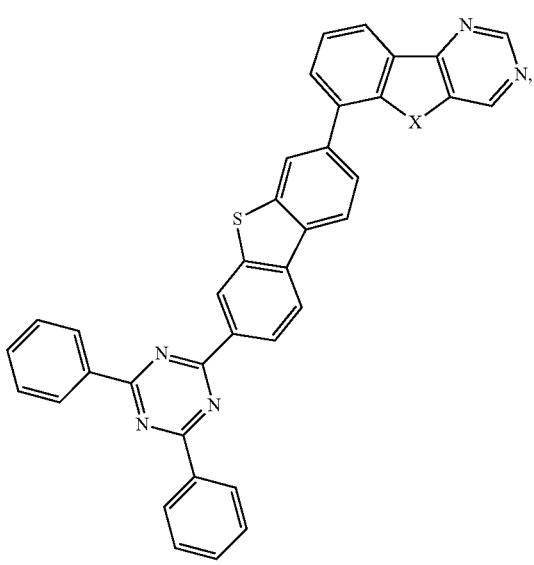

wherein Compound 154 is when X = O,
Compound 155 is when X = S, and
Compound 156 is when X = Se -continued

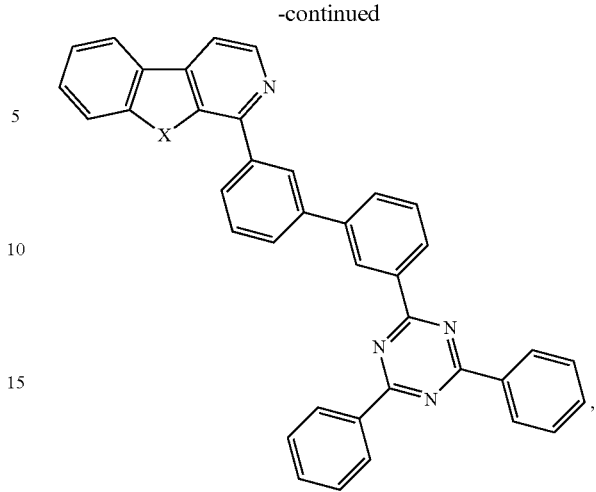

wherein Compound 157 is when X = O,
Compound 158 is when X = S, and
Compound 159 is when X = Se

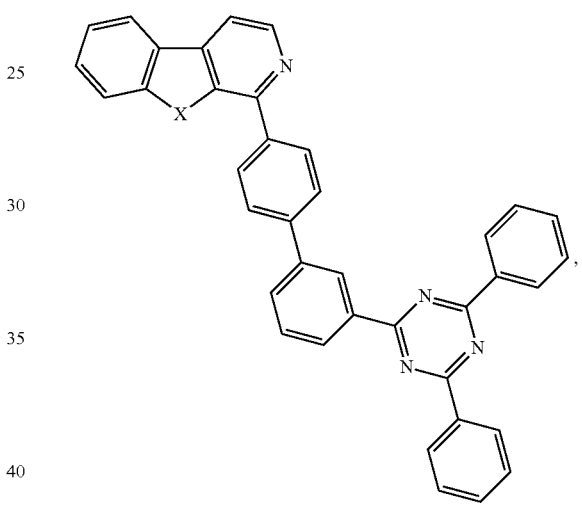

wherein Compound 160 is when X = O,
Compound 161 is when X = S, and
Compound 162 is when X = Se

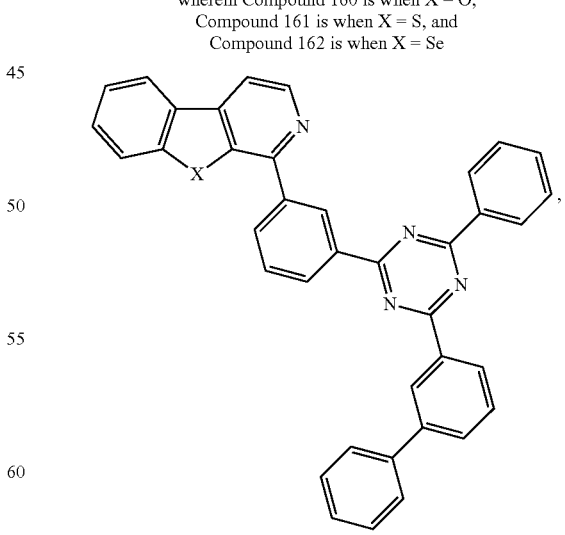

wherein Compound 163 is when X = O,
Compound 164 is when X = S, and
Compound 165 is when X = Se -continued

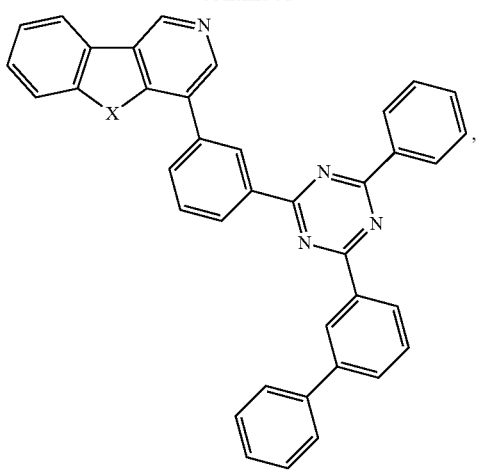

wherein Compound 166 is when X = O,
Compound 167 is when X = S, and
Compound 168 is when X = Se

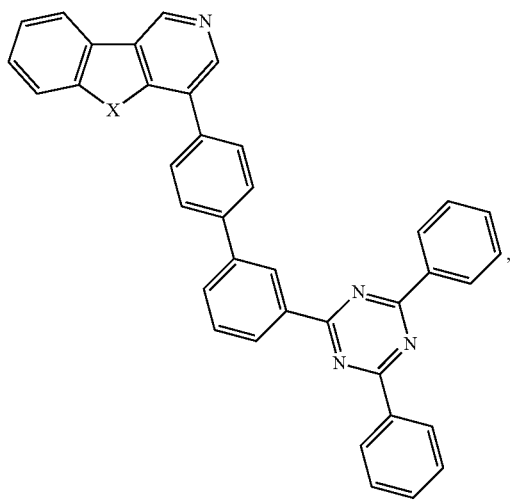

wherein Compound 169 is when X = O,
Compound 170 is when X = S, and
Compound 171 is when X = Se

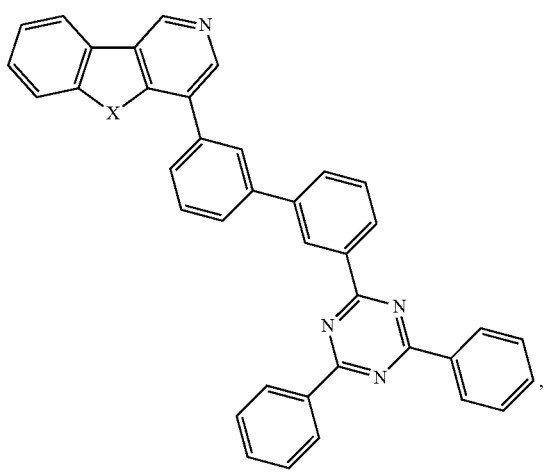

wherein Compound 172 is when X = O,
Compound 173 is when X = S, and
Compound 174 is when X = Se -continued

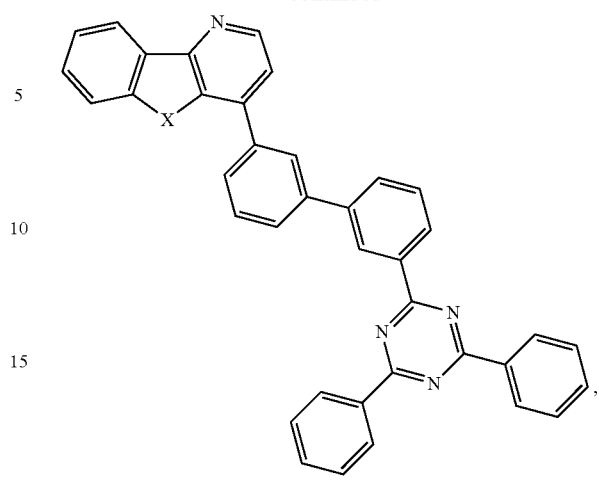

wherein Compound 175 is when X = O,
Compound 176 is when X = S, and
Compound 177 is when X = Se

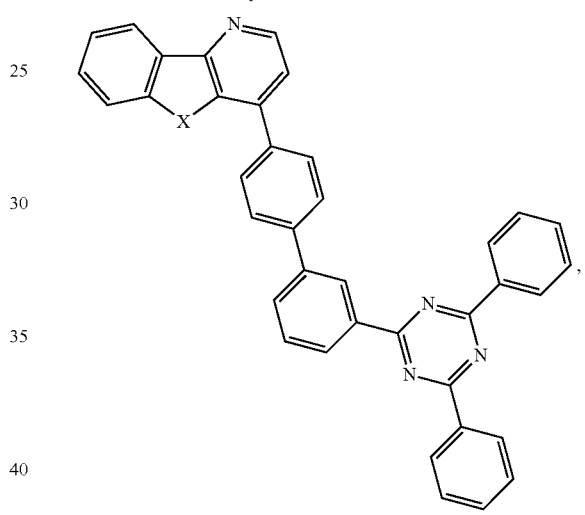

wherein Compound 178 is when X = O,
Compound 179 is when X = S, and
Compound 180 is when X = Se

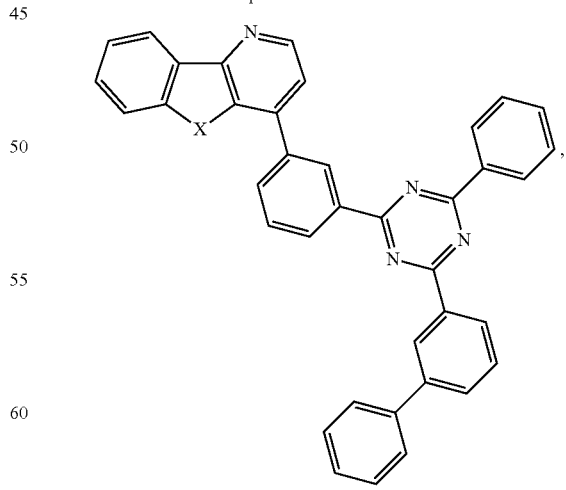

wherein Compound 181 is when X = O,
Compound 182 is when X = S, and
Compound 183 is when X = Se

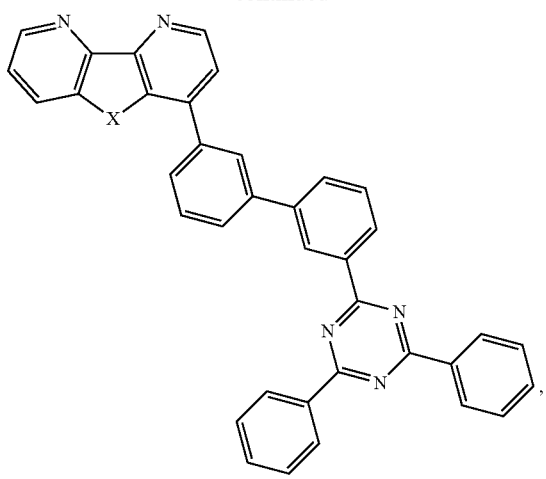

wherein Compound 184 is when X = O,
Compound 185 is when X = S, and
Compound 186 is when X = Se

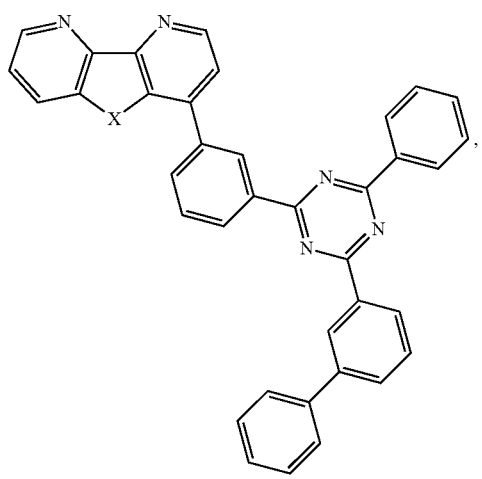

wherein Compound 187 is when X = O,
Compound 188 is when X = S, and
Compound 189 is when X = Se

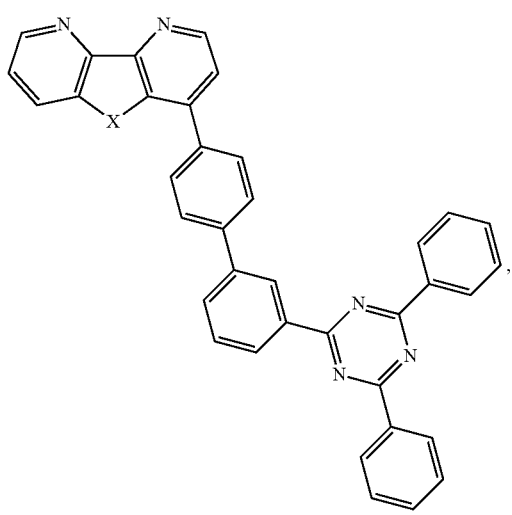

wherein Compound 190 is when X = O,
Compound 191 is when X = S, and
Compound 192 is when X = Se

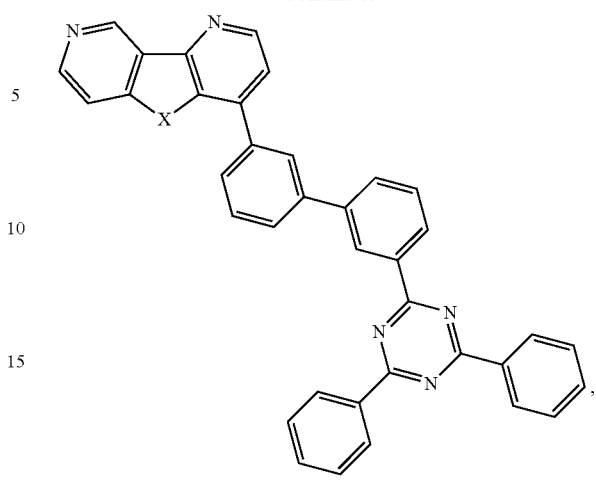

wherein Compound 193 is when X = O,
Compound 194 is when X = S, and
Compound 195 is when X = Se

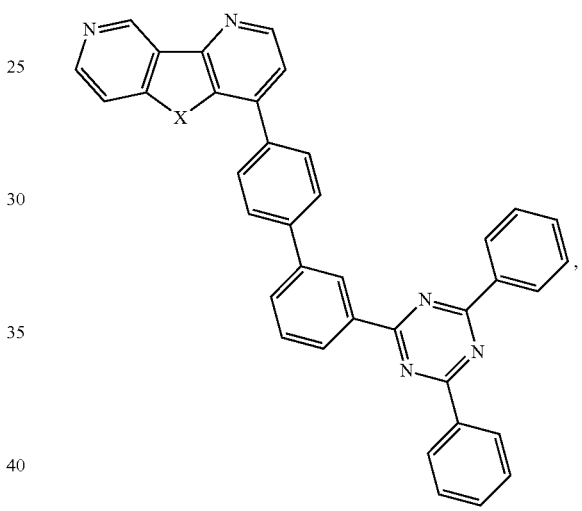

wherein Compound 196 is when X = O,
Compound 197 is when X = S, and
Compound 198 is when X = Se

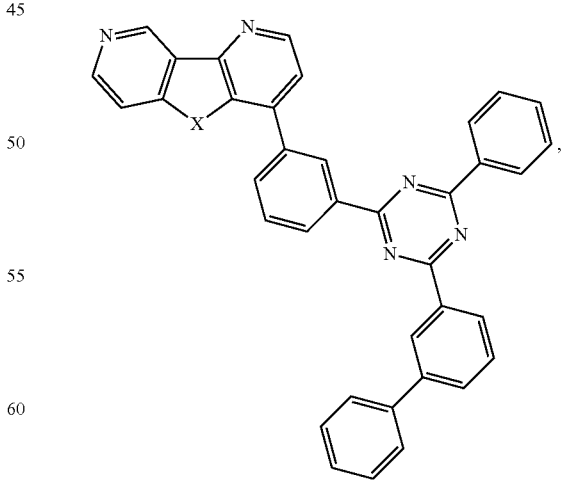

wherein Compound 199 is when X = O,
Compound 200 is when X = S, and
Compound 201 is when X = Se -continued

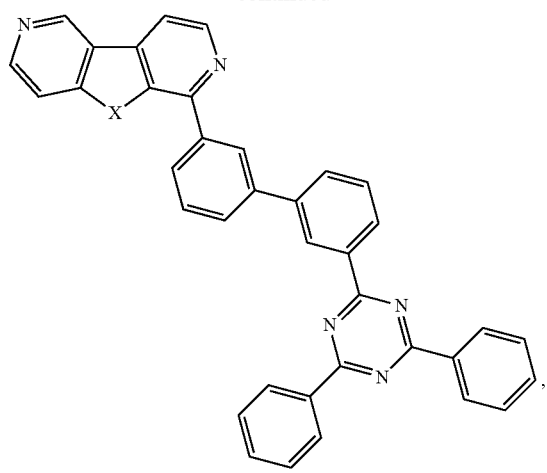

wherein Compound 202 is when X = O,
Compound 203 is when X = S, and
Compound 204 is when X = Se

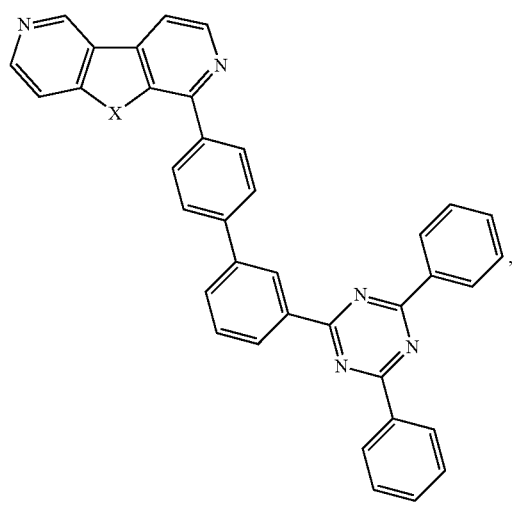

wherein Compound 205 is when X = O,
Compound 206 is when X = S, and
Compound 207 is when X = Se

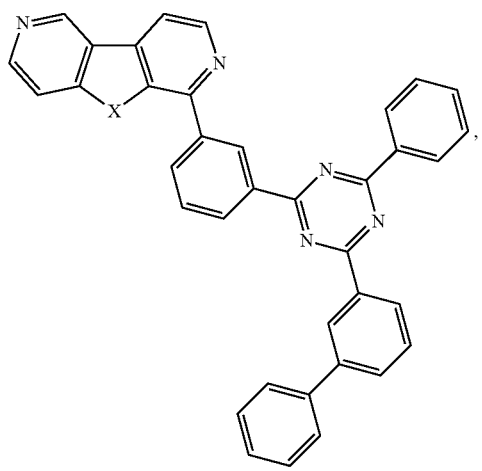

wherein Compound 208 is when X = O,
Compound 209 is when X = S, and
Compound 210 is when X = Se -continued

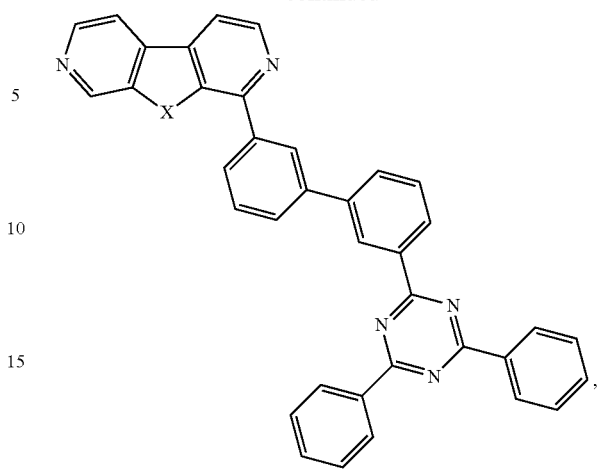

wherein Compound 211 is when X = O,
Compound 212 is when X = S, and
Compound 213 is when X = Se

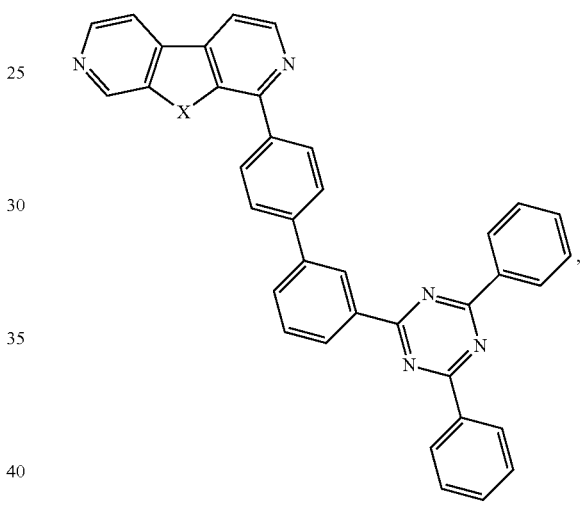

wherein Compound 214 is when X = O,
Compound 215 is when X = S, and
Compound 216 is when X = Se

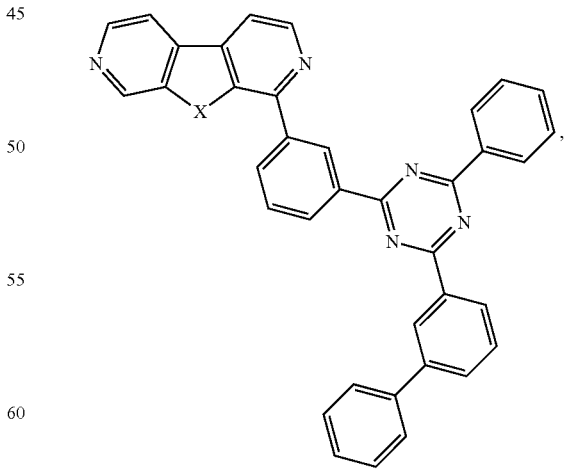

wherein Compound 217 is when X = O,
Compound 218 is when X = S, and
Compound 219 is when X = Se -continued

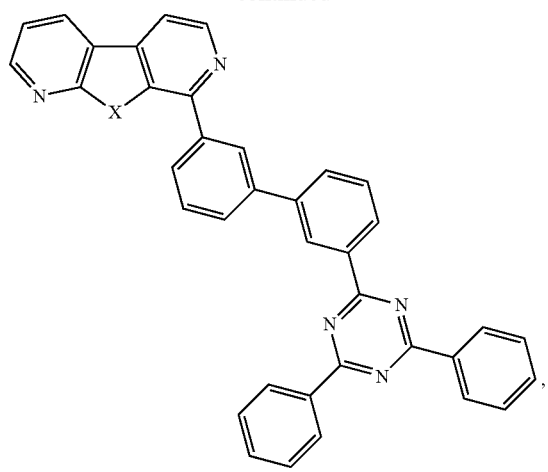

wherein Compound 220 is when X = O,
Compound 221 is when X = S, and
Compound 222 is when X = Se

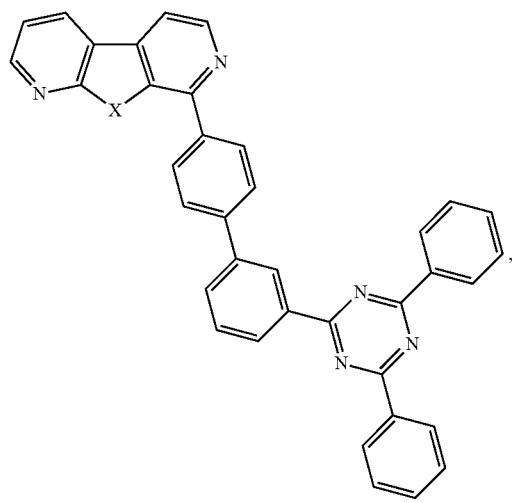

wherein Compound 223 is when X = O,
Compound 224 is when X = S, and
Compound 225 is when X = Se

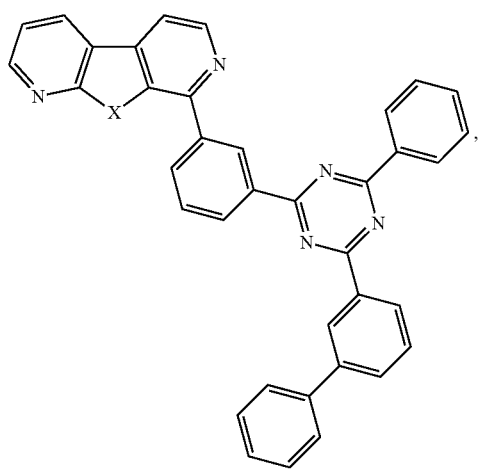

wherein Compound 226 is when X = O,
Compound 227 is when X = S, and
Compound 228 is when X = Se -continued

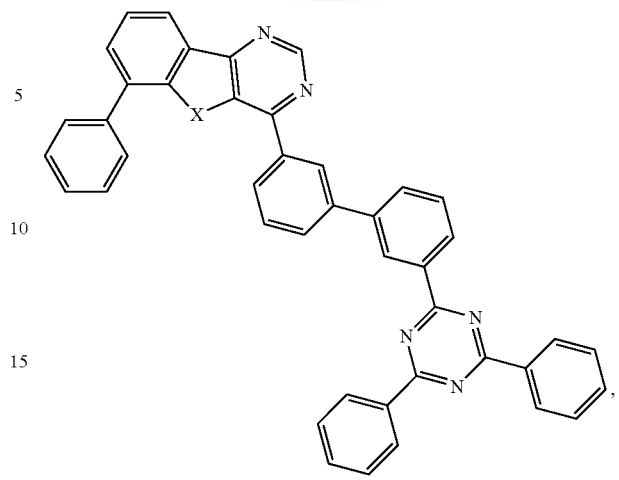

wherein Compound 289 is when X = O,
Compound 290 is when X = S, and
Compound 291 is when X = Se

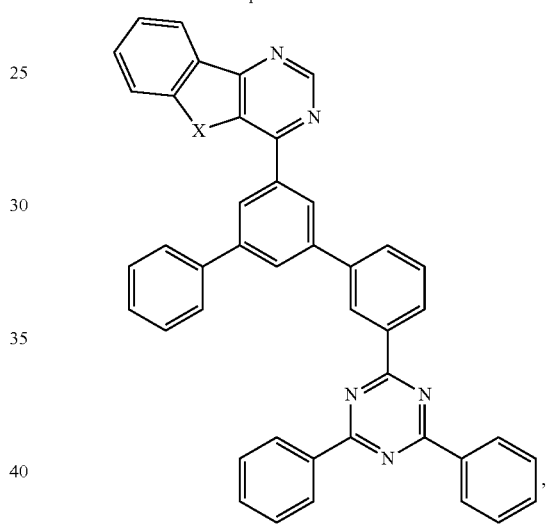

wherein Compound 292 is when X = O,
Compound 293 is when X = S, and
Compound 294 is when X = Se

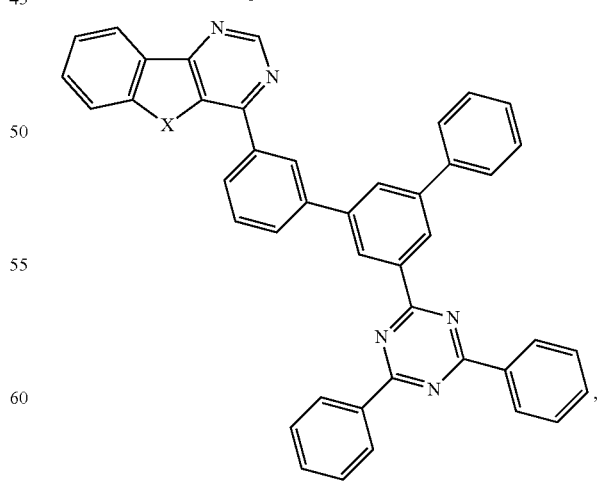

wherein Compound 295 is when X = O,
Compound 296 is when X = S, and
Compound 297 is when X = Se -continued

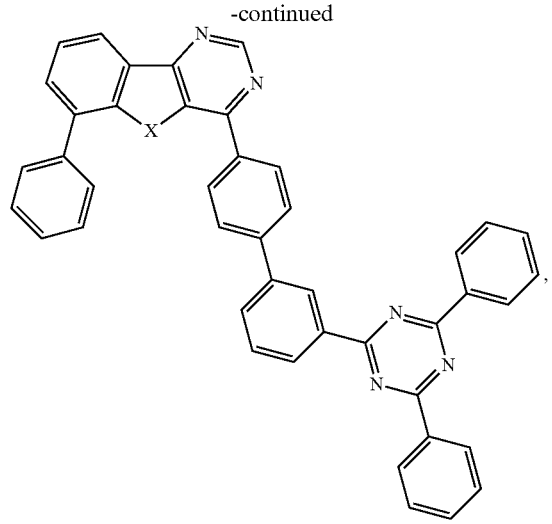

wherein Compound 298 is when X = O,
Compound 299 is when X = S, and
Compound 300 is when X = Se

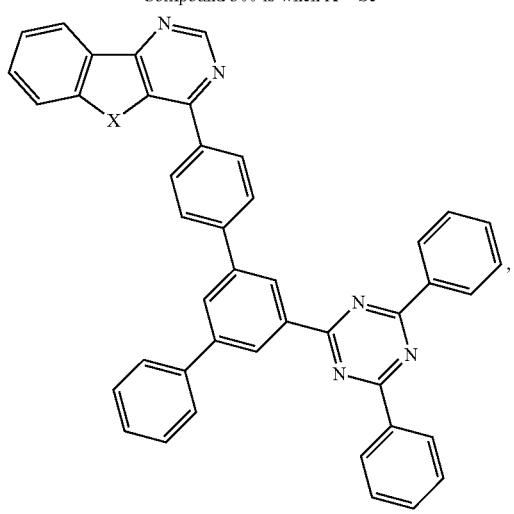

wherein Compound 301 is when X = O,
Compound 302 is when X = S, and
Compound 303 is when X = Se

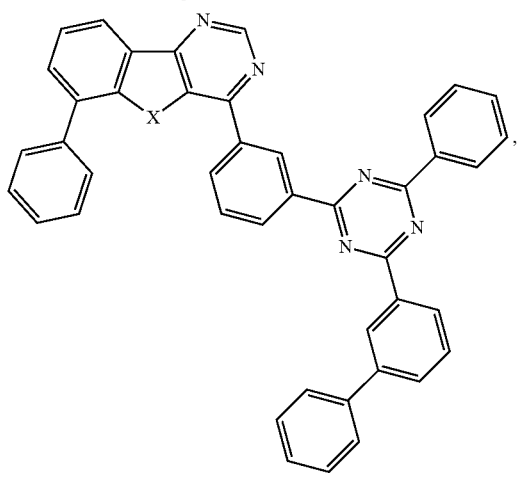

wherein Compound 304 is when X = O,
Compound 305 is when X = S, and
Compound 306 is when X = Se -continued

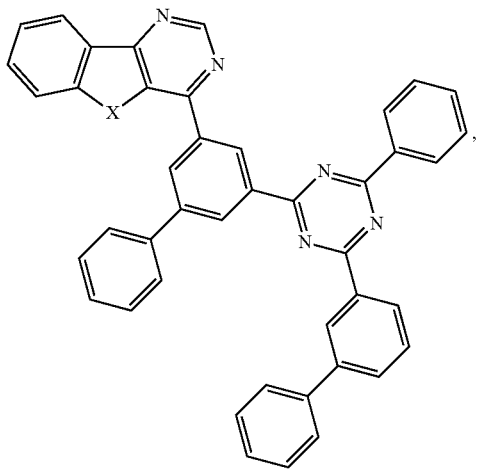

wherein Compound 307 is when X = O,
Compound 308 is when X = S, and
Compound 309 is when X = Se

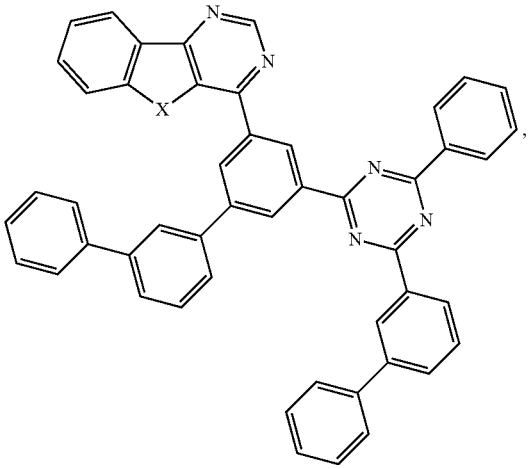

wherein Compound 310 is when X = O,
Compound 311 is when X = S, and
Compound 312 is when X = Se

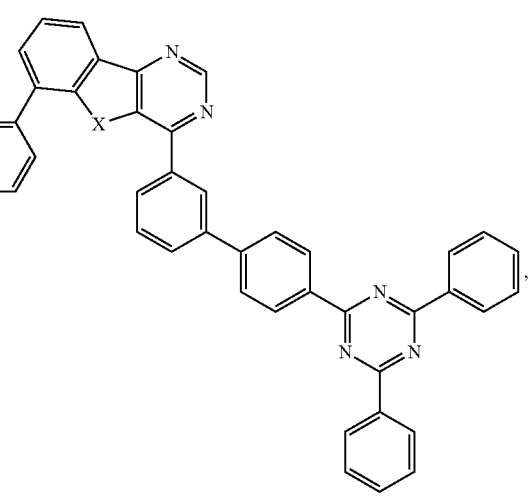

wherein Compound 313 is when X = O,
Compound 314 is when X = S, and
Compound 315 is when X = Se 273
-continued
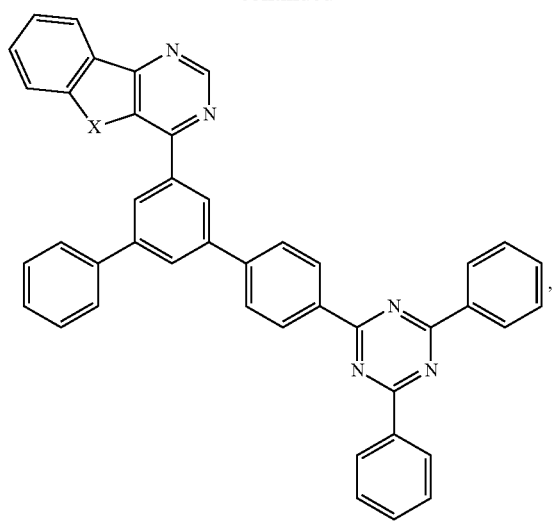
wherein Compound 316 is when X = O,
Compound 317 is when X = S, and
Compound 318 is when X = Se
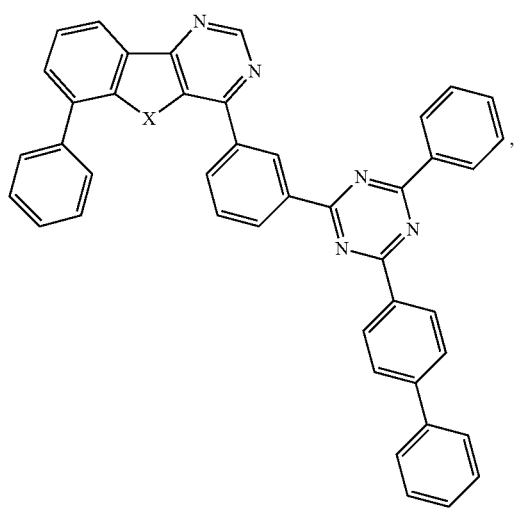
wherein Compound 319 is when X = O,
Compound 320 is when X = S, and
Compound 321 is when X = Se
274
-continued
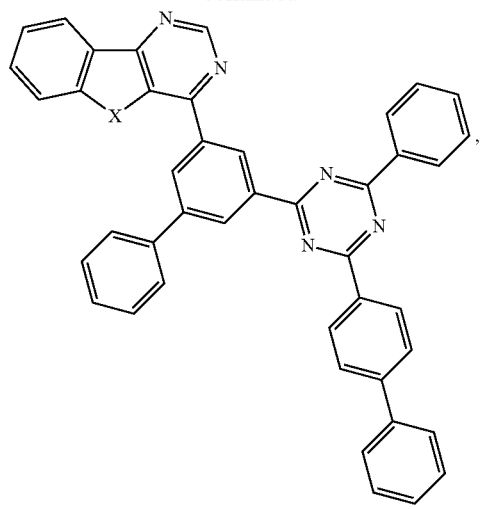
wherein Compound 322 is when X = O,
Compound 323 is when X = S, and
Compound 324 is when X = Se
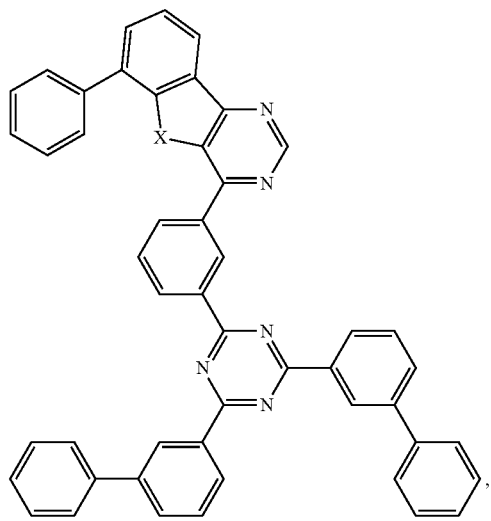
wherein Compound 325 is when X = O,
Compound 326 is when X = S, and
Compound 327 is when X = Se -continued
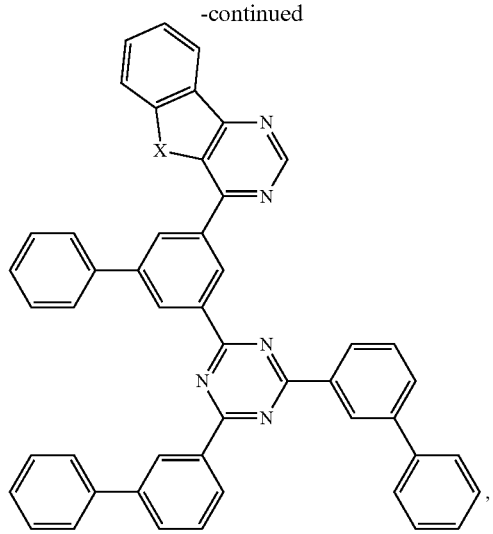
wherein Compound 328 is when X = O,
Compound 329 is when X = S, and
Compound 330 is when X = Se
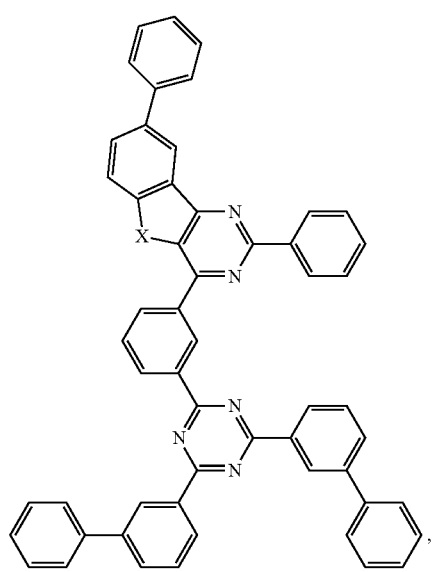
wherein Compound 331 is when X = O,
Compound 332 is when X = S, and
Compound 333 is when X = Se
-continued
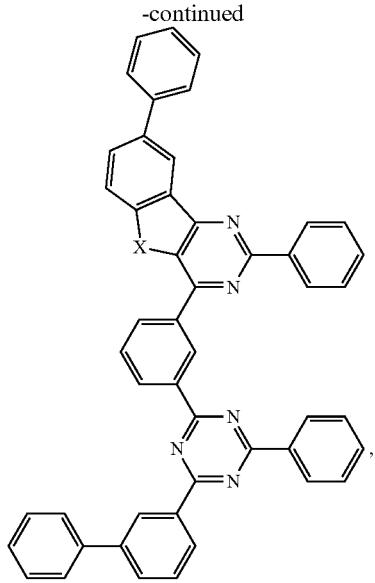
wherein Compound 334 is when X = O,
Compound 335 is when X = S, and
Compound 336 is when X = Se
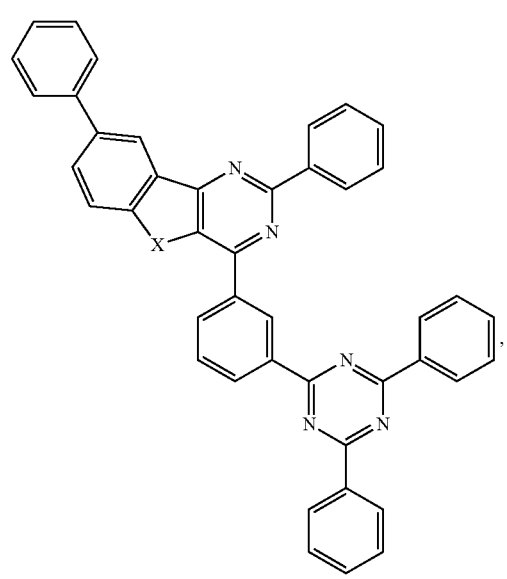
wherein Compound 337 is when X = O,
Compound 338 is when X = S, and
Compound 339 is when X = Se -continued

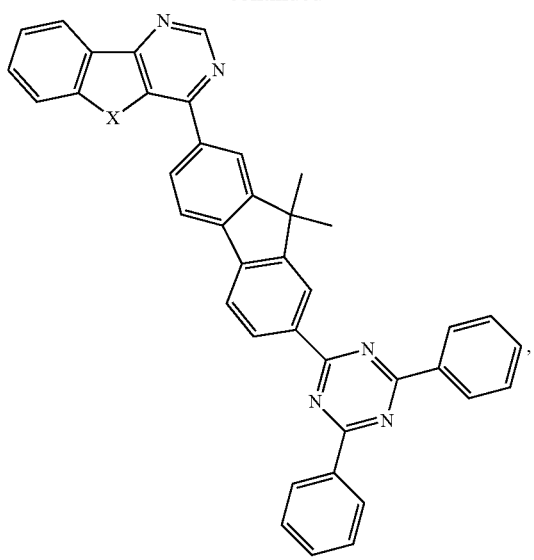

wherein Compound 340 is when X = O,
Compound 341 is when X = S, and
Compound 342 is when X = Se

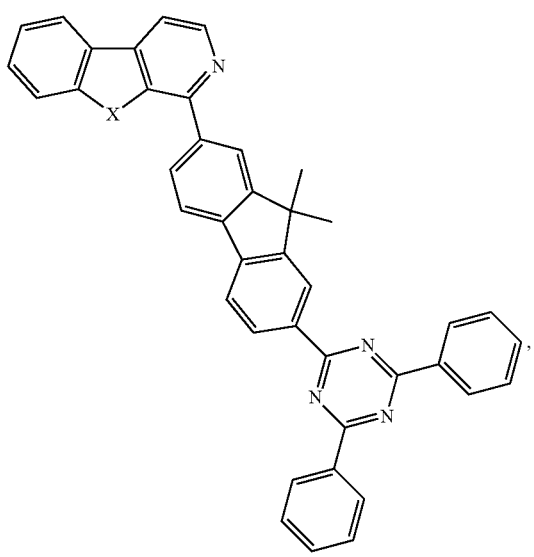

wherein Compound 343 is when X = O,
Compound 344 is when X = S, and
Compound 345 is when X = Se -continued

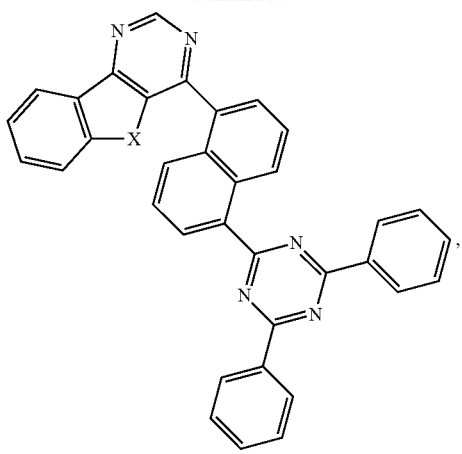

wherein Compound 346 is when X = O,
Compound 347 is when X = S, and
Compound 348 is when X = Se

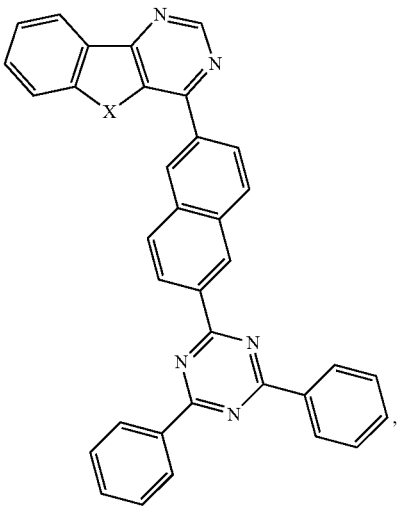

wherein Compound 349 is when X = O,
Compound 350 is when X = S, and
Compound 351 is when X = Se

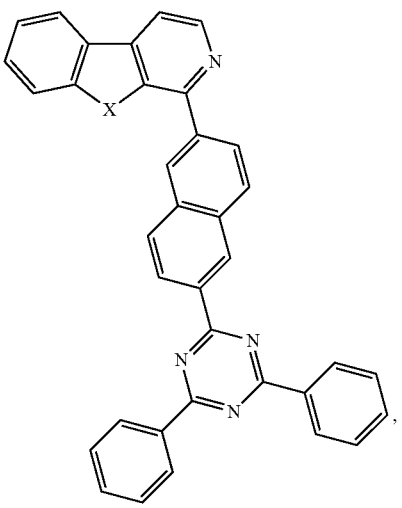

wherein Compound 352 is when X = O,
Compound 353 is when X = S, and
Compound 354 is when X = Se 279
-continued
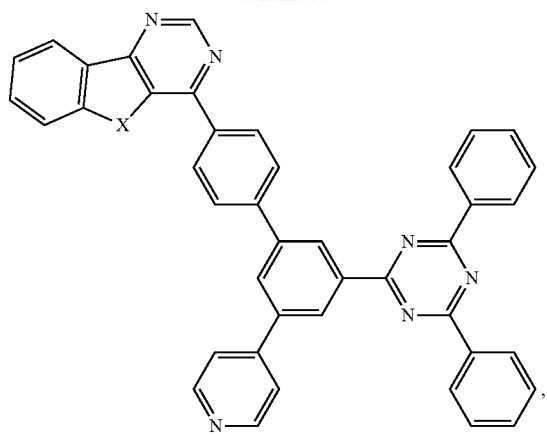
wherein Compound 355 is when X = O,
Compound 356 is when X = S, and
Compound 357 is when X = Se
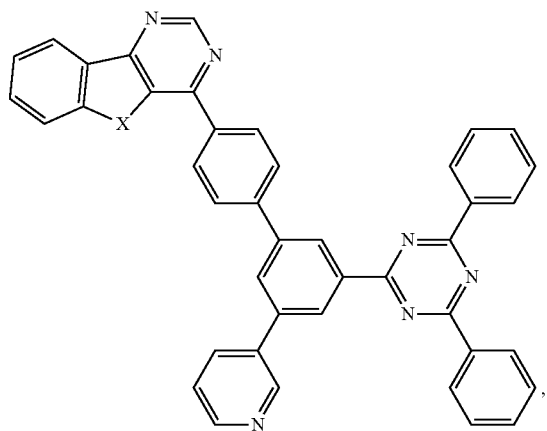
wherein Compound 358 is when X = O,
Compound 359 is when X = S, and
Compound 360 is when X = Se
280
-continued
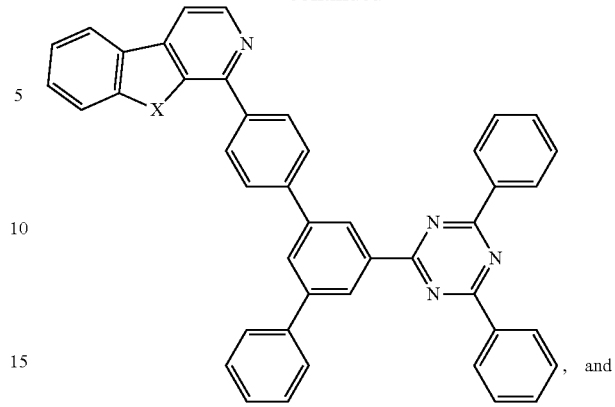
, and
wherein Compound 361 is when X = O,
Compound 362 is when X = S, and
Compound 363 is when X = Se
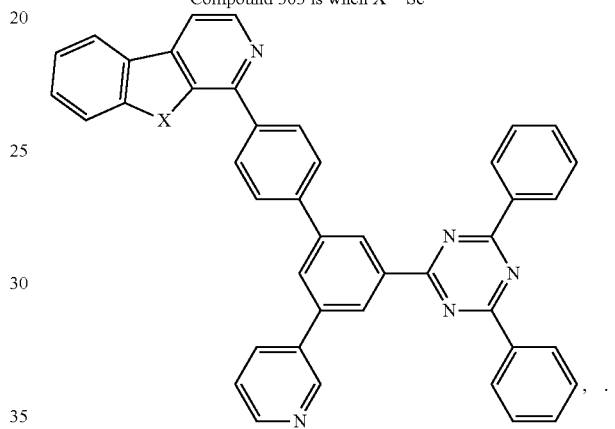
.
wherein Compound 364 is when X = O,
Compound 365 is when X = S, and
Compound 366 is when X = Se
* * * * *